US007078188B2

(12) United States Patent
Batra et al.

(10) Patent No.: US 7,078,188 B2
(45) Date of Patent: Jul. 18, 2006

(54) MUC17 ENCODING NUCLEIC ACID SEQUENCES, POLYPEPTIDES, ANTIBODIES AND METHODS OF USE THEREOF

(75) Inventors: Surinder Batra, Omaha, NE (US); Nicolas Moniaux, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 139 days.

(21) Appl. No.: 10/704,781

(22) Filed: Nov. 10, 2003

(65) Prior Publication Data
US 2005/0100925 A1 May 12, 2005

(51) Int. Cl.
C12P 21/06 (2006.01)
C07H 17/00 (2006.01)

(52) U.S. Cl. .................. 435/69.1; 435/252.3; 435/325; 435/320.1; 536/23.1

(58) Field of Classification Search ................ 536/23.1; 435/320.1, 325, 252.3, 69.1
See application file for complete search history.

(56) References Cited

OTHER PUBLICATIONS

Andrianifahanana, M., Moniaux, N., Schmied, B. M., Ringel, J., Friess, H., Hollingsworth, M. A., Buchler, M. W., Aubert, J. P., and Batra, S. K., "Mucin (MUC) gene expression in human pancreatic adenocarcinoma and chronic pancreatitis: a potential role of MUC4 as a tumor marker of diagnostic significance", (2001) Clin Cancer Res 7, 4033-4040.

Balague, C., Gambus, G., Carrato, C., Porchet, N., Aubert, J. P., Kim, Y. S., and Real, F. X., "Altered expression of MUC2, MUC4, and MUC5 mucin genes in pancreas tissues and cancer cell lines", (1994) Gastroenterology 106, 1054-1061.

Choudhury, A., Moniaux, N., Winpenny, J. P., Hollingsworth, M. A., Aubert, J. P., and Batra, S. K., "Human MUC4 mucin cDNA and its variants in pancreatic carcinoma", (2000) J Biochem (Tokyo) 128, 233-243.

Hollingsworth, M. A., Strawhecker, J. M., Caffrey, T. C., and Mack, D. R., "Expression of MUC1, MUC2, MUC3 and MUC4 mucin mRNAs in human pancreatic and intestinal tumor cell lines", (1994) Int J Cancer 57, 198-203.

Swartz, M. J., Batra, S. K., Varshney, G. C., Hollingsworth, M. A., Yeo, C. J., Cameron, J. L., Willentz, R. E., Hruban, R. H., and Argani, P., "MUC4 expression increases progressively in pancreatic intraepithelial neoplasia", (2002) Am J Clin Pathol 117, 791-796.

Jepson, S., Komatsu, M., Haq, B., Arango, M. E., Huang, D., Carraway, C. A., and Carraway, K. L., "Muc4/sialomucin complex, the intramembrane ErbB2 ligand, induces specific phosphorylation of ErbB2 and enhances expression of p27(kip), but does not activate mitogen-activated kinase or protein kinaseB/Akt pathways", (2002) Oncogene 21, 7524-7532.

Moniaux, N., Escande, F., Porchet, N., Aubert, J. P., and Batra, S. K., "Structural organization and classification of the human mucin genes", (2001) Front Biosci. 6, D1192-D1206.

Yin, B. W. and Lloyd, K. O., "Molecular Cloning of the CA125 Ovarian Cancer Antigen. Identification as a New Mucin, MUC16", (2001) J Biol.Chem. 276, 27371-27375.

O'Brien, T. J., Beard, J. B., Underwood, L. J., Dennis, R. A., Santin, A. D., and York, L., "The CA 125 gene: an extracellular superstructure dominated by repeat sequences", (2001) Tumour.Biol. 22, 348-366.

Chen, Y., Zhao, Y. H., Kalaslavadi, T. B., Harnati, E., Nehrke, K., Le, A. D., Ann, D. K., and Wu, R., "Genome-wide search and identification of a novel gel-forming mucin MUC19/Muc19 in glandular tissues", (2003) Am J Respir. Cell Mol.Biol.

(Continued)

Primary Examiner—Karen Cochrane Carlson
(74) Attorney, Agent, or Firm—Dann Dorfman Herrell and Skillman; Kathleen D. Rigaut

(57) ABSTRACT

Disclosed herein are human MUC17-encoding nucleotide sequences, proteins, antibodies, and methods for use thereof.

23 Claims, 23 Drawing Sheets

OTHER PUBLICATIONS

Gum, J. R., Jr., Crawley, S. C., Hicks, J. W., Szymkowski, D. E., and Kim, Y. S., "MUC17, a novel membrane-tethered mucin", (2002) Biochem Biophys.Res Commun. 291, 466-475.

Baruch, A., Hartmann, M., Yoeli, M., Adereth, Y., Greenstein, S., Stadler, Y., Skornik, Y., Zaretsky, J., Smorodinsky, N. I., Keydar, I., and Wreschner, D. H., "The breast cancer-associated MUC1 gene generates both a receptor and its cognate binding protein", (1999) Cancer Res 59, 1552-1561.

Choudhury, A., Moniaux, N., Ringel, J., King, J., Moore, E., Aubert, J. P., and, and Batra, S. K., "Alternate splicing at the 3'-end of the human pancreatic tumor-associated mucin MUC4 cDNA", (2001) Teratogenesis, Carcinogenesis, and Mutagenesis 21, 83-96.

Crawley, S. C., Gum, J. R. J., Hicks, J. W., Pratt, W. S., Aubert, J. P., Swallow, D. M., and Kim, Y. S., "Genomic organization and structure of the 3'region of human MUC3: alternative splicing predicts membrane-bound and soluble forms of the mucin", (1999) Biochem Biophys Res Commun 263, 728-736.

Moniaux, N., Escande, F., Batra, S. K., Porchet, N., Laine, A., and Aubert, J. P., "Alternative splicing generates a family of putative secreted and membrane-associated MUC4 mucins", (2000) Eur J Biochem 267, 4536-4544.

Obermair, A., Schmid, B. C., Stimpfl, M., Fasching, B., Preyer, O., Leodolter, S., Crandon, A. J., and Zeillinger, R., "Novel MUC1 splice variants are expressed in cervical carcinoma", (2001) Gynecol.Oncol. 83, 343-347.

Choudhury, A., Singh, R. K., Moniaux, N., El-Metwally, T. H., Aubert, J. P., and Batra, S. K, "Retinoic acid-dependent transforming growth factor-beta 2-mediated induction of MUC4 mucin expression in human pancreatic tumor cells follows retinoic acid receptor-alpha signaling pathway", (2000) J Biol Chem 275, 33929-33936.

Moniaux, N., Nollet, S., Porchet, N., Degand, P., Laine, A., and Aubert, J. P., "Complete sequence of the human mucin MUC4: a putative cell membrane-associated mucin", (1999) Biochem J 338, 325-333.

Reid, C. J., Gould, S., and Harris, A., "Developmental Expression of Mucin Genes in the Human Respiratory Tract", (1997) Am J Respir Cell Mol Biol 17, 592-598.

Van Seuningen, I, Pigny, P., Perrais, M., Porchet, N., and Aubert, J. P., "Transcriptional regulation of the 11p15 mucin genes. Towards new biological tools in human therapy, in inflammatory diseases and cancer?", (2001) Front Biosci. 6:D1216-34.

Mitchell, M. S. (2002) Curr.Opin.Investig.Drugs 3, 150-158.

Balague, C., Audie, J. P., Porchet, N., and Real, F. X., "In situ hybridization shows distinct patterns of mucin gene expression in normal, benign, and malignant pancreas tissues", (1995) Gastroenterology 109, 953-964.

Williams, S. J., McGuckin, M. A., Gotley, D. C., Eyre, H. J., Sutherland, G. R., and Antalis, T. M., "Two novel mucin genes down-regulated in colorectal cancer identified by differential display", (1999) Cancer Res 59, 4083-4089.

Corrales, et al., "Normal human conjunctival epithelium expresses MUC 13, MUC 15, MUC 16 and MUC 17 mucin genes", Arch. Soc. Esp. Oftalmol. (2003); 78(7): 375-381 [English Abstract].

Ho, et al., "N-glycosylation is required for the surface localization of MUC 17 mucin", Int. J. Oncol. (2003), 23(3) 585-592.

Nollet, S., Moniaux, N., Maury, J., Petitprez, D., Degand, P., Laine, A., Porchet, N., Aubert, J.P., "Human mucin gene MUC4: organization of its 5'-region and polymorphism of its central tandem repeat array", Biochem. J. 332:739-48, (1998).

Terris, B., Dubois, S., Buisine, M., Sauvanet, A., Ruszniewski, P., Aubert J., Porchet, N., Couvelard, A., Degott, C., Fléjou, J., "Mucin gene expression in intraductal papillary-mucinous pancreatic tumours and related lesions", Journal of Pathology (2002), 197: 632-637.

Figure 1
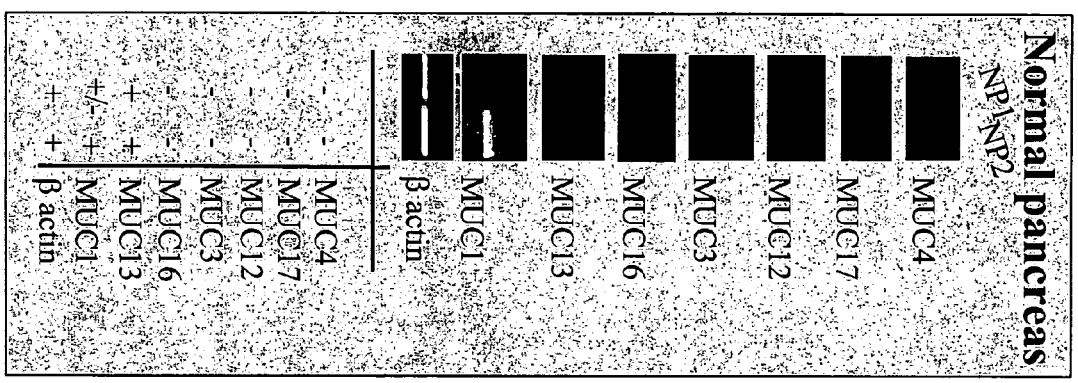
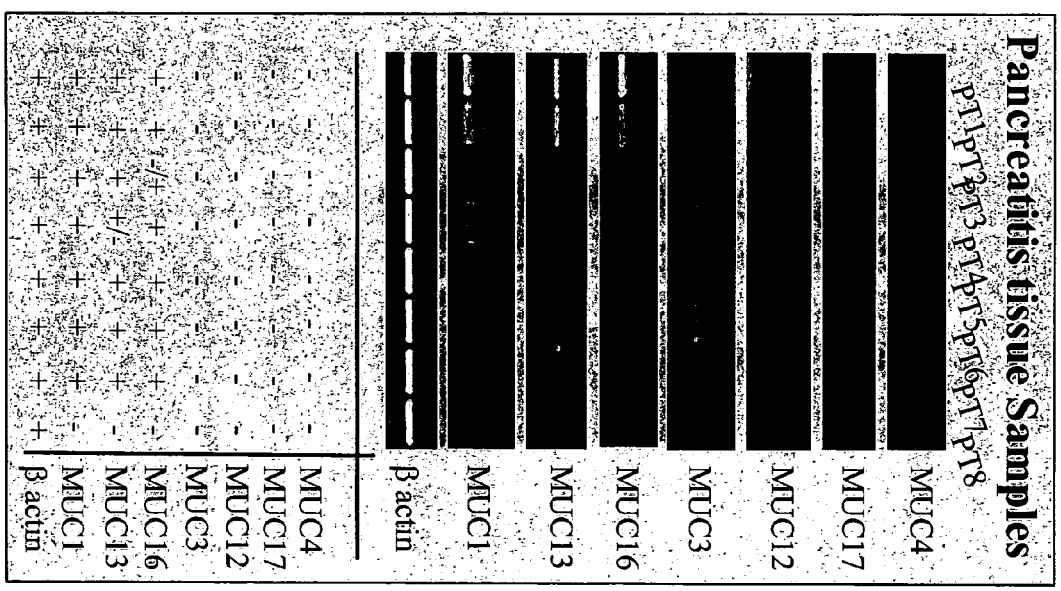

Full length MUC17 sequence, SEQ ID NO: 1

Final MUC17.seq  Length: 14246
```
   1 TTTCGCCAGC TCCTCTGGGG GTGACAGGCA AGTGAGACGT GCTCAGAGCT
  51 CCGATGCCAA GGCCAGGGAC CATGGCGCTG TGTCTGCTGA CCTTGGTCCT
 101 CTCGCTCTTG CCCCCACAAG CTGCTGCAGA ACAGGGCCTC AGTGTGAACA
 151 GGGCTGTGTG GGATGGAGGA GGGTGCATCT CCCAAGGGGA CGTCTTGAAC
 201 CGTCAGTGCC AGCAGCTGTC TCAGCACGTT AGGACAGGTT CTGCGACAAA
 251 CACCGCCACA GGTACAACAT CTACAAATGT CGTGGAGCCA AGAATGTATT
 301 TGAGTTGCAG CACCAACCCT GAGATGACCT CGATTGAGTC CAGtGTGACT
 351 TCAGACACTC CTGGTGTCTC CAGTACCAGG ATGACACCAA CAGAATCCAG
 401 AACAACTTCA GAATCTACCA GTGACAGCAC CACACTTTTC CCCAGTCCTA
 451 CTGAAGACAC TTCATCTCCT ACAACTCCTG AAGGCACCGA CGTGCCCATG
 501 TCAACACCAA GTGAAGAAAG CATTTCATCA ACAATGGCTT TTGTCAGCAC
 551 TGCACCTCTT CCCAGTTTTG AGGCCTACAC ATCTTTAACA TATAAGGTTG
 601 ATATGAGCAC ACCTCTGACC ACTTCTACTC AGGCAAGTTC ATCTCCTACT
 651 ACTCCTGAAA GCACCACCAT ACCCAAATCA ACTAACAGTG AAGGAAGCAC
 701 TCCATTAACA AGTATGCCTG CCAGCACCAT GAAGGTGGCC AGTTCAGAGG
 751 CTATCACCCT TTTGACAACT CCTGTTGAAA TCAGCACACC TGTGACCATT
 801 TCTGCTCAAG CCAGTTCATC TCCTACAACT GCTGAAGGTC CCAGCCTGTC
 851 AAACTCAGCT CCTAGTGGAG GAAGCACTCC ATTAACAAGA ATGCCTCTCA
 901 GCGTGATGCT GGTGGTCAGT TCTGAGGCTA GCACCCTTTC AACAACTCCT
 951 GCTGCCACCA ACATTCCTGT GATCACTTCT ACTGAAGCCA GTTCATCTCC
1001 TACAACGGCT GAAGGCACCA GCATACCAAC CTCAACTTAT ACTGAAGGAA
1051 GCACTCCATT AACAAGTACG CCTGCCAGCA CCATGCCGGT TGCCACTTCT
1101 GAAATGAGCA CACTTTCAAT AACTCCTGTT GACACCAGCA CACTTGTGAC
1151 CACTTCTACT GAACCCAGTT CACTTCCTAC AACTGCTGAA GCTACCAGCA
1201 TGCTAACCTC AACTCTTAGT GAAGGAAGCA CTCCATTAAC AAATATGCCT
1251 GTCAGCACCA TATTGGTGGC CAGTTCTGAG GCTAGCACCA CTTCAACAAT
1301 TCCTGTTGAC TCCAAAACTT TTGTGACCAC TGCTAGTGAA GCCAGCTCAT
1351 CTCCCACAAC TGCTGAAGAT ACCAGCATTG CAACCTCAAC TCCTAGTGAA
1401 GGAAGCACTC CATTAACAAG TATGCCTGTC AGCACCACTC CAGTGGCCAG
1451 TTCTGAGGCT AGCAACCTTT CAACAACTCC TGTTGACTCC AAAACTCAGG
1501 TGACCACTTC TACTGAAGCC AGTTCATCTC CTCCAACTGC TGAAGTTAAC
1551 AGCATGCCAA CCTCAACTCC TAGTGAAGGA AGCACTCCAT TAACAAGTAT
1601 GTCTGTCAGC ACCATGCCGG TGGCCAGTTC TGAGGCTAGC ACCCTTTCAA
1651 CAACTCCTGT TGACACCAGC ACACCTGTGA CCACTTCTAG TGAAGCCAGT
1701 TCATCTTCTA CAACTCCTGA AGGTACCAGC ATACCAACCT CAACTCCTAG
1751 TGAAGGAAGC ACTCCATTAA CAAACATGCC TGTCAGCACC AGGCTGGTGG
1801 TCAGTTCTGA GGCTAGCACC ACTTCAACAA CTCCTGCTGA CTCCAACACT
1851 TTTGTGACCA CTTCTAGTGA AGCTAGTTCA TCTTCTACAA CTGCTGAAGG
1901 TACCAGCATG CCAACCTCAA CTTACAGTGA AAGAGGCACT ACAATAACAA
1951 GTATGTCTGT CAGCACCACA CTGGTGGCCA GTTCTGAGGC TAGCACCCTT
```

Figure 6A

```
2001  TCAACAACTC CTGTTGACTC CAACACTCCT GTGACCACTT CAACTGAAGC
2051  CACTTCATCT TCTACAACTG CGGAAGGTAC CAGCATGCCA ACCTCAACTT
2101  ATACTGAAGG AAGCACTCCA TTAACAAGTA TGCCTGTCAA CACCACACTG
2151  GTGGCCAGTT CTGAGGCTAG CACCCTTTCA ACAACTCCTG TTGACACCAG
2201  CACACCTGTG ACCACTTCAA CTGAAGCCAG TTCCTCTCCT ACAACTGCTG
2251  ATGGTGCCAG TATGCCAACC TCAACTCCTA GTGAAGGAAG CACTCCATTA
2301  ACAAGTATGC CTGTCAGCAA AACGCTGTTG ACCAGTTCTG AGGCTAGCAC
2351  CCTTTCAACA ACTCCTCTTG ACAAGCAC ACATATCACC ACTTCTACTG
2401  AAGCCAGTTG CTCTCCTACA ACCACTGAAG GTACCAGCAT GCCAATCTCA
2451  ACTCCTAGTG AAGGAAGTCC TTTATTAACA AGTATACCTG TCAGCATCAC
2501  ACCGGTGACC AGTCCTGAGG CTAGCACCCT TTCAACAACT CCTGTTGACT
2551  CCAACAGTCC TGTGACCACT TCTACTGAAG TCAGTTCATC TCCTACACCT
2601  GCTGAAGGTA CCAGCATGCC AACCTCAACT TATAGTGAAG GAAGAACTCC
2651  TTTAACAAGT ATGCCTGTCA GCACCACACT GGTGGCCACT TCTGCAATCA
2701  GCACCCTTTC AACAACTCCT GTTGACACCA GCACACCTGT GACCAATTCT
2751  ACTGAAGCCC GTTCGTCTCC TACAACTTCT GAAGGTACCA GCATGCCAAC
2801  CTCAACTCCT GGGGAAGGAA GCACTCCATT AACAAGTATG CCTGACAGCA
2851  CCACGCCGGT AGTCAGTTCT GAGGCTAGAA CACTTTCAGC AACTCCTGTT
2901  GACACCAGCA CACCTGTGAC CACTTCTACT GAAGCCACTT CATCTCCTAC
2951  AACTGCTGAA GGTACCAGCA TACCAACCTC GACTCCTAGT GAAGGAACGA
3001  CTCCATTAAC AAGCACACCT GTCAGCCACA CGCTGGTGGC CAATTCTGAG
3051  GCTAGCACCC TTTCAACAAC TCCTGTTGAC TCCAACACTC CTTTGACCAC
3101  TTCTACTGAA GCCAGTTCAC CTCCTCCCAC TGCTGAAGGT ACCAGCATGC
3151  CAACCTCAAC TCCTAGTGAA GGAAGCACTC CATTAACACG TATGCCTGTC
3201  AGCACCACAA TGGTGGCCAG TTCTGAAACG AGCACACTTT CAACAACTCC
3251  TGCTGACACC AGCACACCTG TGACCACTTA TTCTCAAGCC AGTTCATCTT
3301  CTACAACTGC TGACGGTACC AGCATGCCAA CCTCAACTTA TAGTGAAGGA
3351  AGCACTCCAC TAACAAGTGT GCCTGTCAGC ACCAGGCTGG TGGTCAGTTC
3401  TGAGGCTAGC ACCCTTTCCA CAACTCCTGT CGACACCAGC ATACCTGTCA
3451  CCACTTCTAC TGAAGCCAGT TCATCTCCTA CAACTGCTGA AGGTACCAGC
3501  ATACCAACCT CACCTCCCAG TGAAGGAACC ACTCCGTTAG CAAGTATGCC
3551  TGTCAGCACC ACGCTGGTGG TCAGTTCTGA GGCTAACACC CTTTCAACAA
3601  CTCCTGTGGA CTCCAAAACT CAGGTGGCCA CTTCTACTGA AGCCAGTTCA
3651  CCTCCTCCAA CTGCTGAAGT TACCAGCATG CCAACCTCAA CTCCTGGAGA
3701  AGAAGCACT CCATTAACAA GTATGCCTGT CAGACACACG CCAGTGGCCA
3751  GTTCTGAGGC TAGCACCCTT TCAACATCTC CGTTGACAC CAGCACACCT
3801  GTGACCACTT CTGCTGAAAC CAGTTCCTCT CCTACAACCG CTGAAGGTAC
3851  CAGCTTGCCA ACCTCAACTA CTAGTGAAGG AAGTACTCTA TTAACAAGTA
3901  TACCTGTCAG CACCACGCTG GTGACCAGTC CTGAGGCTAG CACCCTTTTA
3951  ACAACTCCTG TTGACACTAA AGGTCCTGTG GTCACTTCTA ATGAAGTCAG
4001  TTCATCTCCT ACACCTGCTG AAGGTACCAG CATGCCAACC TCAACTTATA
4051  GTGAAGGAAG AACTCCTTTA ACAAGTATAC CTGTCAACAC CACACTGGTG
4101  GCCAGTTCTG CAATCAGCAT CCTTTCAACA ACTCCTGTTG ACAACAGCAC
4151  ACCTGTGACC ACTTCTACTG AAGCCTGTTC ATCTCCTACA ACTTCTGAAG
```

Figure 6B

```
4201  GTACCAGCAT GCCAAACTCA AATCCTAGTG AAGGAACCAC TCCGTTAACA
4251  AGTATACCTG TCAGCACCAC GCCGGTAGTC AGTTCTGAGG CTAGCACCCT
4301  TTCAGCAACT CCTGTTGACA CCAGCACCCC TGGGACCACT TCTGCTGAAG
4351  CCACTTCATC TCCTACAACT GCTGAAGGTA TCAGCATACC AACCTCAACT
4401  CCTAGTGAAG GAAAGACTCC ATTAAAAAGT ATACCTGTCA GCAACACGCC
4451  GGTGGCCAAT TCTGAGGCTA GCACCCTTTC AACAACTCCT GTTGACTCTA
4501  ACAGTCCTGT GGTCACTTCT ACAGCAGTCA GTTCATCTCC TACACCTGCT
4551  GAAGGTACCA GCATAGCAAT CTCAACGCCT AGTGAAGGAA GCACTGCATT
4601  AACAAGTATA CCTGTCAGCA CCACAACAGT GGCCAGTTCT GAAATCAACA
4651  GCCTTTCAAC AACTCCTGCT GTCACCAGCA CACCTGTGAC CACTTATTCT
4701  CAAGCCAGTT CATCTCCTAC AACTGCTGAC GGTACCAGCA TGCAAACCTC
4751  AACTTATAGT GAAGGAAGCA CTCCACTAAC AAGTTTGCCT GTCAGCACCA
4801  TGCTGGTGGT CAGTTCTGAG GCTAACACCC TTTAACAAC CCCTATTGAC
4851  TCCAAAACTC AGGTGACCGC TTCTACTGAA GCCAGTTCAT CTACAACGC
4901  TGAAGGTAGC AGCATGACAA TCTCAACTCC TAGTGAAGGA AGTCCTCTAT
4951  TAACAAGTAT ACCTGTCAGC ACCACGCCGG TGGCCAGTCC TGAGGCTAGC
5001  ACCCTTTCAA CAACTCCTGT TGACTCCAAC AGTCCTGTGA TCACTTCTAC
5051  TGAAGTCAGT TCATCTCCTA CACCTGCTGA AGGTACCAGC ATGCCAACCT
5101  CAACTTATAC TGAAGGAAGA ACTCCTTTAA CAAGTATAAC TGTCAGAACA
5151  ACACCGGTGG CCAGCTCTGC AATCAGCACC CTTTCAACAA CTCCCGTTGA
5201  CAACAGCACA CCTGTGACCA CTTCTACTGA AGCCCGTTCA TCTCCTACAA
5251  CTTCTGAAGG TACCAGCATG CCAAACTCAA CTCCTAGTGA AGGAACCACT
5301  CCATTAACAA GTATACCTGT CAGCACCACG CCGGTACTCA GTTCTGAGGC
5351  TAGCACCCTT TCAGCAACTC CTATTGACAC CAGCACCCCT GTGACCACTT
5401  CTACTGAAGC CACTTCGTCT CCTACAACTG CTGAAGGTAC CAGCATACCA
5451  ACCTCGACTC TTAGTGAAGG AATGACTCCA TTAACAAGCA CACCTGTCAG
5501  CCACACGCTG GTGGCCAATT CTGAGGCTAG CACCCTTTCA CAACTCCTG
5551  TTGACTCTAA CAGTCCTGTG GTCACTTCTA CAGCAGTCAG TTCATCTCCT
5601  ACACCTGCTG AAGGTACCAG CATAGCAACC TCAACGCCTA GTGAAGGAAG
5651  CACTGCATTA ACAAGTATAC CTGTCAGCAC CACAACAGTG GCCAGTTCTG
5701  AAACCAACAC CCTTTCAACA ACTCCCGCTG TCACCAGCAC ACCTGTGACC
5751  ACTTATGCTC AAGTCAGTTC ATCTCCTACA ACTGCTGACG GTAGCAGCAT
5801  GCCAACCTCA ACTCCTAGGG AAGGAAGGCC TCCATTAACA AGTATACCTG
5851  TCAGCACCAC AACAGTGGCC AGTTCTGAAA TCAACACCCT TTCAACAACT
5901  CTTGCTGACA CCAGGACACC TGTGACCACT TATTCTCAAG CCAGTTCATC
5951  TCCTACAACT GCTGATGGTA CCAGCATGCC AACCCCAGCT TATAGTGAAG
6001  GAAGCACTCC ACTAACAAGT ATGCCTCTCA GCACCACGCT GGTGGTCAGT
6051  TCTGAGGCTA GCACTCTTTC CACAACTCCT GTTGACACCA GCACTCCTGC
6101  CACCACTTCT ACTGAAGGCA GTTCATCTCC TACAACTGCA GGAGGTACCA
6151  GCATACAAAC CTCAACTCCT AGTGAACGGA CCACTCCATT AGCAGGTATG
6201  CCTGTCAGCA CTACGCTTGT GGTCAGTTCT GAGGGTAACA CCCTTTCAAC
6251  AACTCCTGTT GACTCCAAAA CTCAGGTGAC CAATTCTACT GAAGCCAGTT
6301  CATCTGCAAC CGCTGAAGGT AGCAGCATGA CAATCTCAGC TCCTAGTGAA
6351  GGAAGTCCTC TACTAACAAG TATACCTCTC AGCACCACGC CGGTGGCCAG
```

Figure 6C

```
6401  TCCTGAGGCT AGCACCCTTT CAACAACTCC TGTTGACTCC AACAGTCCTG
6451  TGATCACTTC TACTGAAGTC AGTTCATCTC CTATACCTAC TGAAGGTACC
6501  AGCATGCAAA CCTCAACTTA TAGTGACAGA AGAACTCCTT TAACAAGTAT
6551  GCCTGTCAGC ACCACAGTGG TGGCCAGTTC TGCAATCAGC ACCCTTTCAA
6601  CAACTCCTGT TGACACCAGC ACACCTGTGA CCAATTCTAC TGAAGCCCGT
6651  TCATCTCCTA CAACTTCTGA AGGTACCAGC ATGCCAACCT CAACTCCTAG
6701  TGAAGGAAGC ACTCCATTCA CAAGTATGCC TGTCAGCACC ATGCCGGTAG
6751  TTACTTCTGA GGCTAGCACC CTTTCAGCAA CTCCTGTTGA CACCAGCACA
6801  CCTGTGACCA CTTCTACTGA AGCCACTTCA TCTCCTACAA CTGCTGAAGG
6851  TACCAGCATA CCAACTTCAA CTCTTAGTGA AGGAACGACT CCATTAACAA
6901  GTATACCTGT CAGCCACACG CTGGTGGCCA ATTCTGAGGT TAGCACCCTT
6951  TCAACAACTC CTGTTGACTC CAACACTCCT TTCACTACTT CTACTGAAGC
7001  CAGTTCACCT CCTCCCACTG CTGAAGGTAC CAGCATGCCA ACCTCAACTT
7051  CTAGTGAAGG AAACACTCCA TTAACACGTA TGCCTGTCAG CACCACAATG
7101  GTGGCCAGTT TTGAAACAAG CACACTTTCT ACAACTCCTG CTGACACCAG
7151  CACACCTGTG ACTACTTATT CTCAAGCCGG TTCATCTCCT ACAACTGCTG
7201  ACGATACTAG CATGCCAACC TCAACTTATA GTGAAGGAAG CACTCCACTA
7251  ACAAGTGTGC CTGTCAGCAC CATGCCGGTG GTCAGTTCTG AGGCTAGCAC
7301  CCATTCCACA ACTCCTGTTG ACACCAGCAC ACCTGTCACC ACTTCTACTG
7351  AAGCCAGTTC ATCTCCTACA ACTGCTGAAG GTACCAGCAT ACCAACCTCA
7401  CCTCCTAGTG AAGGAACCAC TCCGTTAGCA AGTATGCCTG TCAGCACCAC
7451  GCCGGTGGTC AGTTCTGAGG CTGGCACCCT TTCCACAACT CCTGTTGACA
7501  CCAGCACACC TATGACCACT TCTACTGAAG CCAGTTCATC TCCTACAACT
7551  GCTGAAGATA TCGTCGTGCC AATCTCAACT GCTAGTGAAG GAAGTACTCT
7601  ATTAACAAGT ATACCTGTCA GCACCACGCC AGTGGCCAGT CCTGAGGCTA
7651  GCACCCTTTC AACAACTCCT GTTGACTCCA ACAGTCCTGT GGTCACTTCT
7701  ACTGAAATCA GTTCATCTGC TACATCCGCT GAAGGTACCA GCATGCCTAC
7751  CTCAACTTAT AGTGAAGGAA GCACTCCATT AAGAAGTATG CCTGTCAGCA
7801  CCAAGCCGTT GGCCAGTTCT GAGGCTAGCA CTCTTTCAAC AACTCCTGTT
7851  GACACCAGCA TACCTGTCAC CACTTCTACT GAAACCAGTT CATCTCCTAC
7901  AACTGCAAAA GATACCAGCA TGCCAATCTC AACTCCTAGT GAAGTAAGTA
7951  CTTCATTAAC AAGTATACTT GTCAGCACCA TGCCAGTGGC CAGTTCTGAG
8001  GCTAGCACCC TTTCAACAAC TCCTGTTGAC ACCAGGACAC TTGTGACCAC
8051  TTCCACTGGA ACCAGTTCAT CTCCTACAAC TGCTGAAGGT AGCAGCATGC
8101  CAACCTCAAC TCCTGGTGAA GAAGCACTC CATTAACAAA TATACTTGTC
8151  AGCACCACGC TGTTGGCCAA TTCTGAGGCT AGCACCCTTT CAACAACTCC
8201  TGTTGACACC AGCACACCTG TCACCACTTC TGCTGAAGCC AGTTCTTCTC
8251  CTACAACTGC TGAAGGTACC AGCATGCGAA TCTCAACTCC TAGTGATGGA
8301  AGTACTCCAT TAACAAGTAT ACTTGTCAGC ACCCTGCCAG TGGCCAGTTC
8351  TGAGGCTAGC ACCGTTTCAA CAACTGCTGT TGACACCAGC ATACCTGTCA
8401  CCACTTCTAC TGAAGCCAGT TCCTCTCCTA CAACTGCTGA AGTTACCAGC
8451  ATGCCAACCT CAACTCCTAG TGAAACAAGT ACTCCATTAA CTAGTATGCC
8501  TGTCAACCAC ACGCCAGTGG CCAGTTCTGA GGCTGGCACC CTTTCAACAA
8551  CTCCTGTTGA CACCAGCACA CCTGTGACCA CTTCTACTAA AGCCAGTTCA
```

Figure 6D

```
 8601  TCTCCTACAA CTGCTGAAGG TATCGTCGTG CCAATCTCAA CTGCTAGTGA
 8651  AGGAAGTACT CTATTAACAA GTATACCTGT CAGCACCACG CCGGTGGCCA
 8701  GTTCTGAGGC TAGCACCCTT TCAACAACTC CTGTTGATAC CAGCATACCT
 8751  GTCACCACTT CTACTGAAGG CAGTTCTTCT CCTACAACTG CTGAAGGTAC
 8801  CAGCATGCCA ATCTCAACTC CTAGTGAAGT AAGTACTCCA TTAACAAGTA
 8851  TACTTGTCAG CACCGTGCCA GTGGCCGGTT CTGAGGCTAG CACCCTTTCA
 8901  ACAACTCCTG TTGACACCAG GACACCTGTC ACCACTTCTG CTGAAGCTAG
 8951  TTCTTCTCCT ACAACTGCTG AAGGTACCAG CATGCCAATC TCAACTCCTG
 9001  GCGAAAGAAG AACTCCATTA ACAAGTATGT CTGTCAGCAC CATGCCGGTG
 9051  GCCAGTTCTG AGGCTAGCAC CCTTTCAAGA ACTCCTGCTG ACACCAGCAC
 9101  ACCTGTGACC ACTTCTACTG AAGCCAGTTC CTCTCCTACA ACTGCTGAAG
 9151  GTACCGGCAT ACCAATCTCA ACTCCTAGTG AAGGAAGTAC TCCATTAACA
 9201  AGTATACCTG TCAGCACCAC GCCAGTGGCC ATTCCTGAGG CTAGCACCCT
 9251  TTCAACAACT CCTGTTGACT CCAACAGTCC TGTGGTCACT TCTACTGAAG
 9301  TCAGTTCATC TCCTACACCT GCTGAAGGTA CCAGCATGCC AATCTCAACT
 9351  TATAGTGAAG GAAGCACTCC ATTAACAGGT GTGCCTGTCA GCACCACACC
 9401  GGTGACCAGT TCTGCAATCA GCACCCTTTC AACAACTCCT GTTGACACCA
 9451  GCACACCTGT GACCACTTCT ACTGAAGCCC ATTCATCTCC TACAACTTCT
 9501  GAAGGTACCA GCATGCCAAC CTCAACTCCT AGTGAAGGAA GTACTCCATT
 9551  AACATATATG CCTGTCAGCA CCATGCTGGT AGTCAGTTCT GAGGATAGCA
 9601  CCCTTTCAGC AACTCCTGTT GACACCAGCA CACCTGTGAC CACTTCTACT
 9651  GAAGCCACTT CATCTACAAC TGCTGAAGGT ACCAGCATTC AACCTCAAC
 9701  TCCTAGTGAA GGAATGACTC CATTAACTAG TGTACCTGTC AGCAACACGC
 9751  CGGTGGCCAG TTCTGAGGCT AGCATCCTTT CAACAACTCC TGTTGACTCC
 9801  AACACTCCTT TGACCACTTC TACTGAAGCC AGTTCATCTC CTCCCACTGC
 9851  TGAAGGTACC AGCATGCCAA CCTCAACTCC TAGTGAAGGA AGCACTCCAT
 9901  TAACAAGTAT GCCTGTCAGC ACCACAACGG TGGCCAGTTC TGAAACGAGC
 9951  ACCCTTTCAA CAACTCCTGC TGACACCAGC ACACCTGTGA CCACTTATTC
10001  TCAAGCCAGT TCATCTCCTC CAATTGCTGA CGGTACTAGC ATGCCAACCT
10051  CAACTTATAG TGAAGGAAGC ACTCCACTAA CAAATATGTC TTTCAGCACC
10101  ACGCCAGTGG TCAGTTCTGA GGCTAGCACC CTTTCCACAA CTCCTGTTGA
10151  CACCAGCACA CCTGTCACCA CTTCTACTGA AGCCAGTTTA TCTCCTACAA
10201  CTGCTGAAGG TACCAGCATA CCAACCTCAA GTCCTAGTGA AGGAACCACT
10251  CCATTAGCAA GTATGCCTGT CAGCACCACG CCGGTGGTCA GTTCTGAGGT
10301  TAACACCCTT TCAACAACTC CTGTGGACTC CAACACTCTG GTGACCACTT
10351  CTACTGAAGC CAGTTCATCT CCTACAATCG CTGAAGGTAC CAGCTTGCCA
10401  ACCTCAACTA CTAGTGAAGG AAGCACTCCA TTATCAATTA TGCCTCTCAG
10451  TACCACGCCG GTGGCCAGTT CTGAGGCTAG CACCCTTTCA ACAACTCCTG
10501  TTGACACCAG CACACCTGTG ACCACTTCTT CTCCAACCAA TTCATCTCCT
10551  ACAACTGCTG AAGTTACCAG CATGCCAACA TCAACTGCTG GTGAAGGAAG
10601  CACTCCATTA ACAAATATGC CTGTCAGCAC CACACCGGTG GCCAGTTCTG
10651  AGGCTAGCAC CCTTTCAACA ACTCCTGTTG ACTCCAACAC TTTTGTTACC
10701  AGTTCTAGTC AAGCCAGTTC ATCTCCAGCA ACTCTTCAGG TCACCACTAT
10751  GCGTATGTCT ACTCCAAGTG AAGGAAGCTC TTCATTAACA ACTATGCTCC
```

Figure 6E

```
10801  TCAGCAGCAC ATATGTGACC AGTTCTGAGG CTAGCACACC TTCCACTCCT
10851  TCTGTTGACA GAAGCACACC TGTGACCACT TCTACTCAGA GCAATTCTAC
10901  TCCTACACCT CCTGAAGTTA TCACCCTGCC AATGTCAACT CCTAGTGAAG
10951  TAAGCACTCC ATTAACCATT ATGCCTGTCA GCACCACATC GGTGACCATT
11001  TCTGAGGCTG GCACAGCTTC AACACTTCCT GTTGACACCA GCACACCTGT
11051  GATCACTTCT ACCCAAGTCA GTTCATCTCC TGTGACTCCT GAAGGTACCA
11101  CCATGCCAAT CTGGACGCCT AGTGAAGGAA GCACTCCATT AACAACTATG
11151  CCTGTCAGCA CCACACGTGT GACCAGCTCT GAGGGTAGCA CCCTTTCAAC
11201  ACCTTCTGTT GTCACCAGCA CACCTGTGAC CACTTCTACT GAAGCCATTT
11251  CATCTTCTGC AACTCTTGAC AGCACCACCA TGTCTGTGTC AATGCCCATG
11301  GAAATAAGCA CCCTTGGGAC CACTATTCTT GTCAGTACCA CACCTGTTAC
11351  GAGGTTTCCT GAGAGTAGCA CCCCTTCCAT ACCATCTGTT TACACCAGCA
11401  TGTCTATGAC CACTGCCTCT GAAGGCAGTT CATCTCCTAC AACTCTTGAA
11451  GGCACCACCA CCATGCCTAT GTCAACTACG AGTGAAAGAA GCACTTTATT
11501  GACAACTGTC CTCATCAGCC CTATATCTGT GATGAGTCCT TCTGAGGCCA
11551  GCACACTTTC AACACCTCCT GGTGATACCA GCACACCTTT GCTCACCTCT
11601  ACCAAAGCCG GTTCATTCTC CATACCTGCT GAAGTCACTA CCATACGTAT
11651  TTCAATTACC AGTGAAAGAA GCACTCCATT AACAACTCTC CTTGTCAGCA
11701  CCACACTTCC AACTAGCTTT CCTGGGGCCA GCATAGCTTC GACACCTCCT
11751  CTTGACACAA GCACAACTTT TACCCCTTCT ACTGACACTG CCTCAACTCC
11801  CACAATTCCT GTAGCCACCA CCATATCTGT ATCAGTGATC ACAGAAGGAA
11851  GCACACCTGG GACAACCATT TTTATTCCCA GCACTCCTGT CACCAGTTCT
11901  ACTGCTGATG TCTTTCCTGC AACAACTGGT GCTGTATCTA CCCCTGTGAT
11951  AACTTCCACT GAACTAAACA CACCATCAAC CTCCAGTAGT AGTACCACCA
12001  CATCTTTTTC AACTACTAAG GAATTTACAA CACCCGCAAT GACTACTGCA
12051  GCTCCCCTCA CATATGTGAC CATGTCTACT GCCCCAGCA CACCCAGAAC
12101  AACCAGCAGA GGCTGCACTA CTTCTGCATC AACGCTTTCT GCAACCAGTA
12151  CACCTCACAC CTCTACTTCT GTCACCACCC GTCCTGTGAC CCCTTCATCA
12201  GAATCCAGCA GGCCGTCAAC AATTACTTCT CACACCATCC CACCTACATT
12251  TCCTCCTGCT CACTCCAGTA CACCTCCAAC AACCTCTGCC TCCTCCACGA
12301  CTGTGAACCC TGAGGCTGTC ACCACCATGA CCACCAGGAC AAAACCCAGC
12351  ACACGGACCA CTTCCTTCCC CACGGTGACC ACCACCGCTG TCCCCACGAA
12401  TACTACAATT AAGAGCAACC CCACCTCAAC TCCTACTGTG CCAAGAACCA
12451  CAACATGCTT TGGAGATGGG TGCCAGAATA CGGCCTCTCG CTGCAAGAAT
12501  GGAGGCACCT GGGATGGGCT CAAGTGCCAG TGTCCCAACC TCTATTATGG
12551  GGAGTTGTGT GAGGAGGTGG TCAGCAGCAT TGACATAGGG CCACCGGAGA
12601  CTATCTCTGC CCAAATGGAA CTGACTGTGA CAGTGACCAG TGTGAAGTTC
12651  ACCGAAGAGC TAAAAAACCA CTCTTCCCAG GAATTCCAGG AGTTCAAACA
12701  GACATTCACG GAACAGATGA ATATTGTGTA TTCCGGGATC CCTGAGTATG
12751  TCGGGGTGAA CATCACAAAG CTACGTCTTG GCAGTGTGGT GGTGGAGCAT
12801  GACGTCCTCC TAAGAACCAA GTACACACCA GAATACAAGA CAGTATTGGA
12851  CAATGCCACY GAAGTAGTGA AAGAGAAAAT CACAAAAGTG ACCACACAGC
12901  AAATAATGAT TAATGATATT TGCTCAGACA TGATGTGTTT CAACACCACT
12951  GGCACCCAAG TGCAAAACAT TACGGTGACC CAGTACGACC CTGAAGAGGA
```

Figure 6F

```
13001  CTGCCGGAAG ATGGCCAAGG AATATGGAGA CTACTTCGTA GTGGAGTACC
13051  GGGACCAGAA GCCATACTGC ATCAGCCCCT GTGAGCCTGG CTTCAGTGTC
13101  TCCAAGAACT GTAACCTCGG CAAGTGCCAG ATGTCTCTAA GTGGACCTCA
13151  GTGCCTCTGC GTGACCACGG AAACTCACTG GTACAGTGGG GAGACCTGTA
13201  ACCAGGGCAC CCAGAAGAGT CTGGTGTACG GCCTCGTGGG GGCAGGGGTC
13251  GTGCTGATGC TGATCATCCT GGTAGCTCTC CTGATGCTCG TTTTCCGCTC
13301  CAAGAGAGAG GTGAAACGGC AAAAGTACAG ATTGTCTCAG TTATACAAGT
13351  GGCAAGAAGA GGACAGTGGA CCAGCTCCTG GGACCTTCCA AAACATTGGC
13401  TTTGACATCT GCCAAGATGA TGATTCCATC CACCTGGAGT CCATCTATAG
13451  TAATTTCCAG CCCTCCTTGA GACACATAGA CCCTGAAACA AAGATCCGAA
13501  TTCAGAGGCC TCAGGTAATG ACGACATCAT TTTAAGGCAT GGAGCTGAGA
13551  AGTCTGGGAG TGAGGAGATC CCAGTCCGGC TAAGCTTGGT GGAGCATTTT
13601  CCCATTGAGA GCCTTCCATG GAACTCAAT  GTTCCCATTG TAAGTACAGG
13651  AAACAAGCCC CGTACTTACC AAGGAGAAAG AGGAGAGACA GCAGTGCTGG
13701  GAGATTCTCA AATAGAAACC CGTGGACGCT CCAATGGGCT TGTCATGATA
13751  TCAGGCTAGG CTTTCCTGCT CATTTTTCAA AGACGCTCCA GATTTGAGGG
13801  TACTCTGACT GTAACATCTA TCACCCCATT GATCGCCAGG ATTGATTTGG
13851  TTGATCTGGC TGAGCAGGCG GGTGTCCCCG TCCTCCCTCA CTGCCCCATA
13901  TGTGTCCCTC CTAAAGCTGC ATGCTCAGTT GAAGAGGACG AGAGGACGAC
13951  CTTCTCTGAT AGAGGAGGAC CACGCTTCAG TCAAAGGCAT ACAAGTATCT
14001  ATCTGGACTT CCCTGCTGGC ACTTCCAAAC AAGCTCAGAG ATGTTCCTCC
14051  CCTCATCTGC CCGGGTTCAG TACCATGGAC AGCGCCCTCG ACCCGCTGTT
14101  TACAACCATG ACCCCTTGGA CACTGGACTG CATGCACTTT ACATATCACA
14151  AAATGCTCTC ATAAGAATTA TTGCATACCA TCTTCATGAA AAACACCTGT
14201  ATTTAAATAT AGGGCATTTA CCTTTTGGTA AAGAAAAAAA AAAAAA
```

Figure 6G

Variant MUC17 sequence, SEQ ID NO: 2

Final MUC17.seq   Length: 14094
```
   1 TTTCGCCAGC TCCTCTGGGG GTGACAGGCA AGTGAGACGT GCTCAGAGCT
  51 CCGATGCCAA GGCCAGGGAC CATGGCGCTG TGTCTGCTGA CCTTGGTCCT
 101 CTCGCTCTTG CCCCCACAAG CTGCTGCAGA ACAGGGCCTC AGTGTGAACA
 151 GGGCTGTGTG GGATGGAGGA GGGTGCATCT CCCAAGGGGA CGTCTTGAAC
 201 CGTCAGTGCC AGCAGCTGTC TCAGCACGTT AGGACAGGTT CTGCGACAAA
 251 CACCGCCACA GGTACAACAT CTACAAATGT CGTGGAGCCA AGAATGTATT
 301 TGAGTTGCAG CACCAACCCT GAGATGACCT CGATTGAGTC CAGtGTGACT
 351 TCAGACACTC CTGGTGTCTC CAGTACCAGG ATGACACCAA CAGAATCCAG
 401 AACAACTTCA GAATCTACCA GTGACAGCAC CACACTTTTC CCCAGTCCTA
 451 CTGAAGACAC TTCATCTCCT ACAACTCCTG AAGGCACCGA CGTGCCCATG
 501 TCAACACCAA GTGAAGAAAG CATTTCATCA ACAATGGCTT TTGTCAGCAC
 551 TGCACCTCTT CCCAGTTTTG AGGCCTACAC ATCTTTAACA TATAAGGTTG
 601 ATATGAGCAC ACCTCTGACC ACTTCTACTC AGGCAAGTTC ATCTCCTACT
 651 ACTCCTGAAA GCACCACCAT ACCCAAATCA ACTAACAGTG AAGGAAGCAC
 701 TCCATTAACA AGTATGCCTG CCAGCACCAT GAAGGTGGCC AGTTCAGAGG
 751 CTATCACCCT TTTGACAACT CCTGTTGAAA TCAGCACACC TGTGACCATT
 801 TCTGCTCAAG CCAGTTCATC TCCTACAACT GCTGAAGGTC CAGCCTGTC
 851 AAACTCAGCT CCTAGTGGAG GAAGCACTCC ATTAACAAGA ATGCCTCTCA
 901 GCGTGATGCT GGTGGTCAGT TCTGAGGCTA GCACCCTTTC AACAACTCCT
 951 GCTGCCACCA ACATTCCTGT GATCACTTCT ACTGAAGCCA GTTCATCTCC
1001 TACAACGGCT GAAGGCACCA GCATACCAAC CTCAACTTAT ACTGAAGGAA
1051 GCACTCCATT AACAAGTACG CCTGCCAGCA CCATGCCGGT TGCCACTTCT
1101 GAAATGAGCA CACTTTCAAT AACTCCTGTT GACACCAGCA CACTTGTGAC
1151 CACTTCTACT GAACCCAGTT CACTTCCTAC AACTGCTGAA GCTACCAGCA
1201 TGCTAACCTC AACTCTTAGT GAAGGAAGCA CTCCATTAAC AAATATGCCT
1251 GTCAGCACCA TATTGGTGGC CAGTTCTGAG GCTAGCACCA CTTCAACAAT
1301 TCCTGTTGAC TCCAAAACTT TTGTGACCAC TGCTAGTGAA GCCAGCTCAT
1351 CTCCCACAAC TGCTGAAGAT ACCAGCATTG CAACCTCAAC TCCTAGTGAA
1401 GGAAGCACTC CATTAACAAG TATGCCTGTC AGCACCACTC CAGTGGCCAG
1451 TTCTGAGGCT AGCAACCTTT CAACAACTCC TGTTGACTCC AAAACTCAGG
1501 TGACCACTTC TACTGAAGCC AGTTCATCTC CTCCAACTGC TGAAGTTAAC
1551 AGCATGCCAA CCTCAACTCC TAGTGAAGGA AGCACTCCAT TAACAAGTAT
1601 GTCTGTCAGC ACCATGCCGG TGGCCAGTTC TGAGGCTAGC ACCCTTTCAA
1651 CAACTCCTGT TGACACCAGC ACACCTGTGA CCACTTCTAG TGAAGCCAGT
1701 TCATCTTCTA CAACTCCTGA AGGTACCAGC ATACCAACCT CAACTCCTAG
1751 TGAAGGAAGC ACTCCATTAA CAAACATGCC TGTCAGCACC AGGCTGGTGG
1801 TCAGTTCTGA GGCTAGCACC ACTTCAACAA CTCCTGCTGA CTCCAACACT
1851 TTTGTGACCA CTTCTAGTGA AGCTAGTTCA TCTTCTACAA CTGCTGAAGG
1901 TACCAGCATG CCAACCTCAA CTTACAGTGA AAGAGGCACT ACAATAACAA
1951 GTATGTCTGT CAGCACCACA CTGGTGGCCA GTTCTGAGGC TAGCACCCTT
```

Figure 7A

```
2001  TCAACAACTC CTGTTGACTC CAACACTCCT GTGACCACTT CAACTGAAGC
2051  CACTTCATCT TCTACAACTG CGGAAGGTAC CAGCATGCCA ACCTCAACTT
2101  ATACTGAAGG AAGCACTCCA TTAACAAGTA TGCCTGTCAA CACCACACTG
2151  GTGGCCAGTT CTGAGGCTAG CACCCTTTCA ACAACTCCTG TTGACACCAG
2201  CACACCTGTG ACCACTTCAA CTGAAGCCAG TTCCTCTCCT ACAACTGCTG
2251  ATGGTGCCAG TATGCCAACC TCAACTCCTA GTGAAGGAAG CACTCCATTA
2301  ACAAGTATGC CTGTCAGCAA AACGCTGTTG ACCAGTTCTG AGGCTAGCAC
2351  CCTTTCAACA ACTCCTCTTG ACAAGCAC ACATATCACC ACTTCTACTG
2401  AAGCCAGTTG CTCTCCTACA ACCACTGAAG GTACCAGCAT GCCAATCTCA
2451  ACTCCTAGTG AAGGAAGTCC TTTATTAACA AGTATACCTG TCAGCATCAC
2501  ACCGGTGACC AGTCCTGAGG CTAGCACCCT TTCAACAACT CCTGTTGACT
2551  CCAACAGTCC TGTGACCACT TCTACTGAAG TCAGTTCATC TCCTACACCT
2601  GCTGAAGGTA CCAGCATGCC AACCTCAACT TATAGTGAAG GAAGAACTCC
2651  TTTAACAAGT ATGCCTGTCA GCACCACACT GGTGGCCACT TCTGCAATCA
2701  GCACCCTTTC AACAACTCCT GTTGACACCA GCACACCTGT GACCAATTCT
2751  ACTGAAGCCC GTTCGTCTCC TACAACTTCT GAAGGTACCA GCATGCCAAC
2801  CTCAACTCCT GGGGAAGGAA GCACTCCATT AACAAGTATG CCTGACAGCA
2851  CCACGCCGGT AGTCAGTTCT GAGGCTAGAA CACTTTCAGC AACTCCTGTT
2901  GACACCAGCA CACCTGTGAC CACTTCTACT GAAGCCACTT CATCTCCTAC
2951  AACTGCTGAA GGTACCAGCA TACCAACCTC GACTCCTAGT GAAGGAACGA
3001  CTCCATTAAC AAGCACACCT GTCAGCCACA CGCTGGTGGC CAATTCTGAG
3051  GCTAGCACCC TTTCAACAAC TCCTGTTGAC TCCAACACTC CTTTGACCAC
3101  TTCTACTGAA GCCAGTTCAC CTCCTCCCAC TGCTGAAGGT ACCAGCATGC
3151  CAACCTCAAC TCCTAGTGAA GGAAGCACTC CATTAACACG TATGCCTGTC
3201  AGCACCACAA TGGTGGCCAG TTCTGAAACG AGCACACTTT CAACAACTCC
3251  TGCTGACACC AGCACACCTG TGACCACTTA TTCTCAAGCC AGTTCATCTT
3301  CTACAACTGC TGACGGTACC AGCATGCCAA CCTCAACTTA TAGTGAAGGA
3351  AGCACTCCAC TAACAAGTGT GCCTGTCAGC ACCAGGCTGG TGGTCAGTTC
3401  TGAGGCTAGC ACCCTTTCCA CAACTCCTGT CGACACCAGC ATACCTGTCA
3451  CCACTTCTAC TGAAGCCAGT TCATCTCCTA CAACTGCTGA AGGTACCAGC
3501  ATACCAACCT CACCTCCCAG TGAAGGAACC ACTCCGTTAG CAAGTATGCC
3551  TGTCAGCACC ACGCTGGTGG TCAGTTCTGA GGCTAACACC CTTTCAACAA
3601  CTCCTGTGGA CTCCAAAACT CAGGTGGCCA CTTCTACTGA AGCCAGTTCA
3651  CCTCCTCCAA CTGCTGAAGT TACCAGCATG CCAACCTCAA CTCCTGGAGA
3701  AAGAAGCACT CCATTAACAA GTATGCCTGT CAGACACACG CCAGTGGCCA
3751  GTTCTGAGGC TAGCACCCTT TCAACATCTC CGTTGACAC CAGCACACCT
3801  GTGACCACTT CTGCTGAAAC CAGTTCCTCT CCTACAACCG CTGAAGGTAC
3851  CAGCTTGCCA ACCTCAACTA CTAGTGAAGG AAGTACTCTA TTAACAAGTA
3901  TACCTGTCAG CACCACGCTG GTGACCAGTC CTGAGGCTAG CACCCTTTTA
3951  ACAACTCCTG TTGACACTAA AGGTCCTGTG GTCACTTCTA ATGAAGTCAG
4001  TTCATCTCCT ACACCTGCTG AAGGTACCAG CATGCCAACC TCAACTTATA
4051  GTGAAGGAAG AACTCCTTTA ACAAGTATAC CTGTCAACAC CACACTGGTG
4101  GCCAGTTCTG CAATCAGCAT CCTTTCAACA ACTCCTGTTG ACAACAGCAC
4151  ACCTGTGACC ACTTCTACTG AAGCCTGTTC ATCTCCTACA ACTTCTGAAG
```

Figure 7B

```
4201  GTACCAGCAT GCCAAACTCA AATCCTAGTG AAGGAACCAC TCCGTTAACA
4251  AGTATACCTG TCAGCACCAC GCCGGTAGTC AGTTCTGAGG CTAGCACCCT
4301  TTCAGCAACT CCTGTTGACA CCAGCACCCC TGGGACCACT TCTGCTGAAG
4351  CCACTTCATC TCCTACAACT GCTGAAGGTA TCAGCATACC AACCTCAACT
4401  CCTAGTGAAG GAAAGACTCC ATTAAAAAGT ATACCTGTCA GCAACACGCC
4451  GGTGGCCAAT TCTGAGGCTA GCACCCTTTC AACAACTCCT GTTGACTCTA
4501  ACAGTCCTGT GGTCACTTCT ACAGCAGTCA GTTCATCTCC TACACCTGCT
4551  GAAGGTACCA GCATAGCAAT CTCAACGCCT AGTGAAGGAA GCACTGCATT
4601  AACAAGTATA CCTGTCAGCA CCACAACAGT GGCCAGTTCT GAAATCAACA
4651  GCCTTTCAAC AACTCCTGCT GTCACCAGCA CACCTGTGAC CACTTATTCT
4701  CAAGCCAGTT CATCTCCTAC AACTGCTGAC GGTACCAGCA TGCAAACCTC
4751  AACTTATAGT GAAGGAAGCA CTCCACTAAC AAGTTTGCCT GTCAGCACCA
4801  TGCTGGTGGT CAGTTCTGAG GCTAACACCC TTTCAACAAC CCCTATTGAC
4851  TCCAAAACTC AGGTGACCGC TTCTACTGAA GCCAGTTCAT CTACAACCGC
4901  TGAAGGTAGC AGCATGACAA TCTCAACTCC TAGTGAAGGA AGTCCTCTAT
4951  TAACAAGTAT ACCTGTCAGC ACCACGCCGG TGGCCAGTCC TGAGGCTAGC
5001  ACCCTTTCAA CAACTCCTGT TGACTCCAAC AGTCCTGTGA TCACTTCTAC
5051  TGAAGTCAGT TCATCTCCTA CACCTGCTGA AGGTACCAGC ATGCCAACCT
5101  CAACTTATAC TGAAGGAAGA ACTCCTTTAA CAAGTATAAC TGTCAGAACA
5151  ACACCGGTGG CCAGCTCTGC AATCAGCACC CTTTCAACAA CTCCGTTGA
5201  CAACAGCACA CCTGTGACCA CTTCTACTGA AGCCCGTTCA TCTCCTACAA
5251  CTTCTGAAGG TACCAGCATG CCAAACTCAA CTCCTAGTGA AGGAACCACT
5301  CCATTAACAA GTATACCTGT CAGCACCACG CCGGTACTCA GTTCTGAGGC
5351  TAGCACCCTT TCAGCAACTC CTATTGACAC CAGCACCCCT GTGACCACTT
5401  CTACTGAAGC CACTTCGTCT CCTACAACTG CTGAAGGTAC CAGCATACCA
5451  ACCTCGACTC TTAGTGAAGG AATGACTCCA TTAACAAGCA CACCTGTCAG
5501  CCACACGCTG GTGGCCAATT CTGAGGCTAG CACCCTTTCA ACAACTCCTG
5551  TTGACTCTAA CAGTCCTGTG GTCACTTCTA CAGCAGTCAG TTCATCTCCT
5601  ACACCTGCTG AAGGTACCAG CATAGCAACC TCAACGCCTA GTGAAGGAAG
5651  CACTGCATTA ACAAGTATAC CTGTCAGCAC CACAACAGTG GCCAGTTCTG
5701  AAACCAACAC CCTTTCAACA ACTCCCGCTG TCACCAGCAC ACCTGTGACC
5751  ACTTATGCTC AAGTCAGTTC ATCTCCTACA ACTGCTGACG GTAGCAGCAT
5801  GCCAACCTCA ACTCCTAGGG AAGGAAGGCC TCCATTAACA AGTATACCTG
5851  TCAGCACCAC AACAGTGGCC AGTTCTGAAA TCAACACCCT TTCAACAACT
5901  CTTGCTGACA CCAGGACACC TGTGACCACT TATTCTCAAG CCAGTTCATC
5951  TCCTACAACT GCTGATGGTA CCAGCATGCC AACCCCAGCT TATAGTGAAG
6001  GAAGCACTCC ACTAACAAGT ATGCCTCTCA GCACCACGCT GGTGGTCAGT
6051  TCTGAGGCTA GCACTCTTTC ACAACTCCT GTTGACACCA GCACTCCTGC
6101  CACCACTTCT ACTGAAGGCA GTTCATCTCC TACAACTGCA GGAGGTACCA
6151  GCATACAAAC CTCAACTCCT AGTGAACGGA CCACTCCATT AGCAGGTATG
6201  CCTGTCAGCA CTACGCTGT GGTCAGTTCT GAGGGTAACA CCCTTTCAAC
6251  AACTCCTGTT GACTCCAAAA CTCAGGTGAC CAATTCTACT GAAGCCAGTT
6301  CATCTGCAAC CGCTGAAGGT AGCAGCATGA CAATCTCAGC TCCTAGTGAA
6351  GGAAGTCCTC TACTAACAAG TATACCTCTC AGCACCACGC CGGTGGCCAG
```

Figure 7C

```
6401  TCCTGAGGCT AGCACCCTTT CAACAACTCC TGTTGACTCC AACAGTCCTG
6451  TGATCACTTC TACTGAAGTC AGTTCATCTC CTATACCTAC TGAAGGTACC
6501  AGCATGCAAA CCTCAACTTA TAGTGACAGA AGAACTCCTT TAACAAGTAT
6551  GCCTGTCAGC ACCACAGTGG TGGCCAGTTC TGCAATCAGC ACCCTTTCAA
6601  CAACTCCTGT TGACACCAGC ACACCTGTGA CCAATTCTAC TGAAGCCCGT
6651  TCATCTCCTA CAACTTCTGA AGGTACCAGC ATGCCAACCT CAACTCCTAG
6701  TGAAGGAAGC ACTCCATTCA CAAGTATGCC TGTCAGCACC ATGCCGGTAG
6751  TTACTTCTGA GGCTAGCACC CTTTCAGCAA CTCCTGTTGA CACCAGCACA
6801  CCTGTGACCA CTTCTACTGA AGCCACTTCA TCTCCTACAA CTGCTGAAGG
6851  TACCAGCATA CCAACTTCAA CTCTTAGTGA AGGAACGACT CCATTAACAA
6901  GTATACCTGT CAGCCACACG CTGGTGGCCA ATTCTGAGGT TAGCACCCTT
6951  TCAACAACTC CTGTTGACTC CAACACTCCT TTCACTACTT CTACTGAAGC
7001  CAGTTCACCT CCTCCCACTG CTGAAGGTAC CAGCATGCCA ACCTCAACTT
7051  CTAGTGAAGG AAACACTCCA TTAACACGTA TGCCTGTCAG CACCACAATG
7101  GTGGCCAGTT TTGAAACAAG CACACTTTCT ACAACTCCTG CTGACACCAG
7151  CACACCTGTG ACTACTTATT CTCAAGCCGG TTCATCTCCT ACAACTGCTG
7201  ACGATACTAG CATGCCAACC TCAACTTATA GTGAAGGAAG CACTCCACTA
7251  ACAAGTGTGC CTGTCAGCAC CATGCCGGTG GTCAGTTCTG AGGCTAGCAC
7301  CCATTCCACA ACTCCTGTTG ACACCAGCAC ACCTGTCACC ACTTCTACTG
7351  AAGCCAGTTC ATCTCCTACA ACTGCTGAAG GTACCAGCAT ACCAACCTCA
7401  CCTCCTAGTG AAGGAACCAC TCCGTTAGCA AGTATGCCTG TCAGCACCAC
7451  GCCGGTGGTC AGTTCTGAGG CTGGCACCCT TTCCACAACT CCTGTTGACA
7501  CCAGCACACC TATGACCACT TCTACTGAAG CCAGTTCATC TCCTACAACT
7551  GCTGAAGATA TCGTCGTGCC AATCTCAACT GCTAGTGAAG GAAGTACTCT
7601  ATTAACAAGT ATACCTGTCA GCACCACGCC AGTGGCCAGT CCTGAGGCTA
7651  GCACCCTTTC AACAACTCCT GTTGACTCCA ACAGTCCTGT GGTCACTTCT
7701  ACTGAAATCA GTTCATCTGC TACATCCGCT GAAGGTACCA GCATGCCTAC
7751  CTCAACTTAT AGTGAAGGAA GCACTCCATT AAGAAGTATG CCTGTCAGCA
7801  CCAAGCCGTT GGCCAGTTCT GAGGCTAGCA CTCTTTCAAC AACTCCTGTT
7851  GACACCAGCA TACCTGTCAC CACTTCTACT GAAACCAGTT CATCTCCTAC
7901  AACTGCAAAA GATACCAGCA TGCCAATCTC AACTCCTAGT GAAGTAAGTA
7951  CTTCATTAAC AAGTATACTT GTCAGCACCA TGCCAGTGGC CAGTTCTGAG
8001  GCTAGCACCC TTTCAACAAC TCCTGTTGAC ACCAGGACAC TTGTGACCAC
8051  TTCCACTGGA ACCAGTTCAT CTCCTACAAC TGCTGAAGGT AGCAGCATGC
8101  CAACCTCAAC TCCTGGTGAA AGAAGCACTC CATTAACAAA TATACTTGTC
8151  AGCACCACGC TGTTGGCCAA TTCTGAGGCT AGCACCCTTT CAACAACTCC
8201  TGTTGACACC AGCACACCTG TCACCACTTC TGCTGAAGCC AGTTCTTCTC
8251  CTACAACTGC TGAAGGTACC AGCATGCGAA TCTCAACTCC TAGTGATGGA
8301  AGTACTCCAT TAACAAGTAT ACTTGTCAGC ACCCTGCCAG TGGCCAGTTC
8351  TGAGGCTAGC ACCGTTTCAA CAACTGCTGT TGACACCAGC ATACCTGTCA
8401  CCACTTCTAC TGAAGCCAGT TCCTCTCCTA CAACTGCTGA AGTTACCAGC
8451  ATGCCAACCT CAACTCCTAG TGAAACAAGT ACTCCATTAA CTAGTATGCC
8501  TGTCAACCAC ACGCCAGTGG CCAGTTCTGA GGCTGGCACC CTTTCAACAA
8551  CTCCTGTTGA CACCAGCACA CCTGTGACCA CTTCTACTAA AGCCAGTTCA
```

Figure 7D

```
8601  TCTCCTACAA CTGCTGAAGG TATCGTCGTG CCAATCTCAA CTGCTAGTGA
8651  AGGAAGTACT CTATTAACAA GTATACCTGT CAGCACCACG CCGGTGGCCA
8701  GTTCTGAGGC TAGCACCCTT TCAACAACTC CTGTTGATAC CAGCATACCT
8751  GTCACCACTT CTACTGAAGG CAGTTCTTCT CCTACAACTG CTGAAGGTAC
8801  CAGCATGCCA ATCTCAACTC CTAGTGAAGT AAGTACTCCA TTAACAAGTA
8851  TACTTGTCAG CACCGTGCCA GTGGCCGGTT CTGAGGCTAG CACCCTTTCA
8901  ACAACTCCTG TTGACACCAG GACACCTGTC ACCACTTCTG CTGAAGCTAG
8951  TTCTTCTCCT ACAACTGCTG AAGGTACCAG CATGCCAATC TCAACTCCTG
9001  GCGAAAGAAG AACTCCATTA ACAAGTATGT CTGTCAGCAC CATGCCGGTG
9051  GCCAGTTCTG AGGCTAGCAC CCTTTCAAGA ACTCCTGCTG ACACCAGCAC
9101  ACCTGTGACC ACTTCTACTG AAGCCAGTTC CTCTCCTACA ACTGCTGAAG
9151  GTACCGGCAT ACCAATCTCA ACTCCTAGTG AAGGAAGTAC TCCATTAACA
9201  AGTATACCTG TCAGCACCAC GCCAGTGGCC ATTCCTGAGG CTAGCACCCT
9251  TTCAACAACT CCTGTTGACT CCAACAGTCC TGTGGTCACT TCTACTGAAG
9301  TCAGTTCATC TCCTACACCT GCTGAAGGTA CCAGCATGCC AATCTCAACT
9351  TATAGTGAAG GAAGCACTCC ATTAACAGGT GTGCCTGTCA GCACCACACC
9401  GGTGACCAGT TCTGCAATCA GCACCCTTTC AACAACTCCT GTTGACACCA
9451  GCACACCTGT GACCACTTCT ACTGAAGCCC ATTCATCTCC TACAACTTCT
9501  GAAGGTACCA GCATGCCAAC CTCAACTCCT AGTGAAGGAA GTACTCCATT
9551  AACATATATG CCTGTCAGCA CCATGCTGGT AGTCAGTTCT GAGGATAGCA
9601  CCCTTTCAGC AACTCCTGTT GACACCAGCA CACCTGTGAC CACTTCTACT
9651  GAAGCCACTT CATCTACAAC TGCTGAAGGT ACCAGCATTC CAACCTCAAC
9701  TCCTAGTGAA GGAATGACTC CATTAACTAG TGTACCTGTC AGCAACACGC
9751  CGGTGGCCAG TTCTGAGGCT AGCATCCTTT CAACAACTCC TGTTGACTCC
9801  AACACTCCTT TGACCACTTC TACTGAAGCC AGTTCATCTC CTCCCACTGC
9851  TGAAGGTACC AGCATGCCAA CCTCAACTCC TAGTGAAGGA AGCACTCCAT
9901  TAACAAGTAT GCCTGTCAGC ACCACAACGG TGGCCAGTTC TGAAACGAGC
9951  ACCCTTTCAA CAACTCCTGC TGACACCAGC ACACCTGTGA CCACTTATTC
10001 TCAAGCCAGT TCATCTCCTC CAATTGCTGA CGGTACTAGC ATGCCAACCT
10051 CAACTTATAG TGAAGGAAGC ACTCCACTAA CAAATATGTC TTTCAGCACC
10101 ACGCCAGTGG TCAGTTCTGA GGCTAGCACC CTTTCCACAA CTCCTGTTGA
10151 CACCAGCACA CCTGTCACCA CTTCTACTGA AGCCAGTTTA TCTCCTACAA
10201 CTGCTGAAGG TACCAGCATA CCAACCTCAA GTCCTAGTGA AGGAACCACT
10251 CCATTAGCAA GTATGCCTGT CAGCACCACG CCGGTGGTCA GTTCTGAGGT
10301 TAACACCCTT TCAACAACTC CTGTGGACTC CAACACTCTG GTGACCACTT
10351 CTACTGAAGC CAGTTCATCT CCTACAATCG CTGAAGGTAC CAGCTTGCCA
10401 ACCTCAACTA CTAGTGAAGG AAGCACTCCA TTATCAATTA TGCCTCTCAG
10451 TACCACGCCG GTGGCCAGTT CTGAGGCTAG CACCCTTTCA ACAACTCCTG
10501 TTGACACCAG CACACCTGTG ACCACTTCTT CTCCAACCAA TTCATCTCCT
10551 ACAACTGCTG AAGTTACCAG CATGCCAACA TCAACTGCTG GTGAAGGAAG
10601 CACTCCATTA ACAAATATGC CTGTCAGCAC CACACCGGTG GCCAGTTCTG
10651 AGGCTAGCAC CCTTTCAACA ACTCCTGTTG ACTCCAACAC TTTTGTTACC
10701 AGTTCTAGTC AAGCCAGTTC ATCTCCAGCA ACTCTTCAGG TCACCACTAT
10751 GCGTATGTCT ACTCCAAGTG AAGGAAGCTC TTCATTAACA ACTATGCTCC
```

Figure 7E

```
10801  TCAGCAGCAC ATATGTGACC AGTTCTGAGG CTAGCACACC TTCCACTCCT
10851  TCTGTTGACA GAAGCACACC TGTGACCACT TCTACTCAGA GCAATTCTAC
10901  TCCTACACCT CCTGAAGTTA TCACCCTGCC AATGTCAACT CCTAGTGAAG
10951  TAAGCACTCC ATTAACCATT ATGCCTGTCA GCACCACATC GGTGACCATT
11001  TCTGAGGCTG GCACAGCTTC AACACTTCCT GTTGACACCA GCACACCTGT
11051  GATCACTTCT ACCCAAGTCA GTTCATCTCC TGTGACTCCT GAAGGTACCA
11101  CCATGCCAAT CTGGACGCCT AGTGAAGGAA GCACTCCATT AACAACTATG
11151  CCTGTCAGCA CCACACGTGT GACCAGCTCT GAGGGTAGCA CCCTTTCAAC
11201  ACCTTCTGTT GTCACCAGCA CACCTGTGAC CACTTCTACT GAAGCCATTT
11251  CATCTTCTGC AACTCTTGAC AGCACCACCA TGTCTGTGTC AATGCCCATG
11301  GAAATAAGCA CCCTTGGGAC CACTATTCTT GTCAGTACCA CACCTGTTAC
11351  GAGGTTTCCT GAGAGTAGCA CCCCTTCCAT ACCATCTGTT TACACCAGCA
11401  TGTCTATGAC CACTGCCTCT GAAGGCAGTT CATCTCCTAC AACTCTTGAA
11451  GGCACCACCA CCATGCCTAT GTCAACTACG AGTGAAAGAA GCACTTTATT
11501  GACAACTGTC CTCATCAGCC CTATATCTGT GATGAGTCCT TCTGAGGCCA
11551  GCACACTTTC AACACCTCCT GGTGATACCA GCACACCTTT GCTCACCTCT
11601  ACCAAAGCCG GTTCATTCTC CATACCTGCT GAAGTCACTA CCATACGTAT
11651  TTCAATTACC AGTGAAAGAA GCACTCCATT AACAACTCTC CTTGTCAGCA
11701  CCACACTTCC AACTAGCTTT CCTGGGGCCA GCATAGCTTC GACACCTCCT
11751  CTTGACACAA GCACAACTTT TACCCCTTCT ACTGACACTG CCTCAACTCC
11801  CACAATTCCT GTAGCCACCA CCATATCTGT ATCAGTGATC ACAGAAGGAA
11851  GCACACCTGG ACAACCATT TTTATTCCCA GCACTCCTGT CACCAGTTCT
11901  ACTGCTGATG TCTTTCCTGC AACAACTGGT GCTGTATCTA CCCCTGTGAT
11951  AACTTCCACT GAACTAAACA CACCATCAAC CTCCAGTAGT AGTACCACCA
12001  CATCTTTTTC AACTACTAAG GAATTTACAA CACCCGCAAT GACTACTGCA
12051  GCTCCCCTCA CATATGTGAC CATGTCTACT GCCCCAGCA CACCCAGAAC
12101  AACCAGCAGA GGCTGCACTA CTTCTGCATC AACGCTTTCT GCAACCAGTA
12151  CACCTCACAC CTCTACTTCT GTCACCACCC GTCCTGTGAC CCCTTCATCA
12201  GAATCCAGCA GGCCGTCAAC AATTACTTCT CACACCATCC CACCTACATT
12251  TCCTCCTGCT CACTCCAGTA CACCTCCAAC AACCTCTGCC TCCTCCACGA
12301  CTGTGAACCC TGAGGCTGTC ACCACCATGA CCACCAGGAC AAAACCCAGC
12351  ACACGGACCA CTTCCTTCCC CACGGTGACC ACCACCGCTG TCCCCACGAA
12401  TACTACAATT AAGAGCAACC CCACCTCAAC TCCTACTGTG CCAAGAACCA
12451  CAACATGCTT TGGAGATGGG TGCCAGAATA CGGCCTCTCG CTGCAAGAAT
12501  GGAGGCACCT GGGATGGGCT CAAGTGCCAG TGTCCCAACC TCTATTATGG
12551  GGAGTTGTGT GAGGAGGTGG TCAGCAGCAT TGACATAGGG CCACCGGAGA
12601  CTATCTCTGC CCAAATGGAA CTGACTGTGA CAGTGACCAG TGTGAAGTTC
12651  ACCGAAGAGC TAAAAAACCA CTCTTCCCAG GAATTCCAGG AGTTCAAACA
12701  GACATTCACG GAACAGATGA ATATTGTGTA TTCCGGGATC CCTGAGTATG
12751  TCGGGGTGAA CATCACAAAG CTACGTCATG ATGTGTTTCA ACACCACTGG
12801  CACCCAAGTG CAAAACATTA CGGTGACCCA GTACGACCCT GAAGAGGACT
```

Figure 7F

```
12851  GCCGGAAGAT GGCCAAGGAA TATGGAGACT ACTTCGTAGT GGAGTACCGG
12901  GACCAGAAGC CATACTGCAT CAGCCCCTGT GAGCCTGGCT TCAGTGTCTC
12951  CAAGAACTGT AACCTCGGCA AGTGCCAGAT GTCTCTAAGT GGACCTCAGT
13001  GCCTCTGCGT GACCACGGAA ACTCACTGGT ACAGTGGGGA GACCTGTAAC
13051  CAGGGCACCC AGAAGAGTCT GGTGTACGGC CTCGTGGGGG CAGGGGTCGT
13101  GCTGATGCTG ATCATCCTGG TAGCTCTCCT GATGCTCGTT TTCCGCTCCA
13151  AGAGAGAGGT GAAACGGCAA AAGTACAGAT TGTCTCAGTT ATACAAGTGG
13201  CAAGAAGAGG ACAGTGGACC AGCTCCTGGG ACCTTCCAAA ACATTGGCTT
13251  TGACATCTGC CAAGATGATG ATTCCATCCA CCTGGAGTCC ATCTATAGTA
13301  ATTTCCAGCC CTCCTTGAGA CACATAGACC CTGAAACAAA GATCCGAATT
13351  CAGAGGCCTC AGGTAATGAC GACATCATTT TAAGGCATGG AGCTGAGAAG
13401  TCTGGGAGTG AGGAGATCCC AGTCCGGCTA AGCTTGGTGG AGCATTTTCC
13451  CATTGAGAGC CTTCCATGGG AACTCAATGT TCCCATTGTA AGTACAGGAA
13501  ACAAGCCCCG TACTTACCAA GGAGAAAGAG GAGAGACAGC AGTGCTGGGA
13551  GATTCTCAAA TAGAAACCCG TGGACGCTCC AATGGGCTTG TCATGATATC
13601  AGGCTAGGCT TTCCTGCTCA TTTTTCAAAG ACGCTCCAGA TTTGAGGGTA
13651  CTCTGACTGT AACATCTATC ACCCCATTGA TCGCCAGGAT TGATTTGGTT
13701  GATCTGGCTG AGCAGGCGGG TGTCCCCGTC CTCCCTCACT GCCCCATATG
13751  TGTCCCTCCT AAAGCTGCAT GCTCAGTTGA AGAGGACGAG AGGACGACCT
13801  TCTCTGATAG AGGAGGACCA CGCTTCAGTC AAAGGCATAC AAGTATCTAT
13851  CTGGACTTCC CTGCTGGCAC TTCCAAACAA GCTCAGAGAT GTTCCTCCCC
13901  TCATCTGCCC GGGTTCAGTA CCATGGACAG CGCCCTCGAC CCGCTGTTTA
13951  CAACCATGAC CCCTTGGACA CTGGACTGCA TGCACTTTAC ATATCACAAA
14001  ATGCTCTCAT AAGAATTATT GCATACCATC TTCATGAAAA ACACCTGTAT
14051  TTAAATATAG GGCATTTACC TTTTGGTAAA GAAAAAAAAA AAAA
```

Figure 7G

```
MUC17 full length, SEQ ID NO: 3, 4493 aa
ORIGIN
       1 MPRPGTMALC LLTLVLSLLP PQAAAEQGLS VNRAVWDGGG CISQGDVLNR QCQQLSQHVR
      61 TGSATNTATG TTSTNVVEPR MYLSCSTNPE MTSIESSVTS DTPGVSSTRM TPTESRTTSE
     121 STSDSTTLFP SPTEDTSSPT TPEGTDVPMS TPSEESISST MAFVSTAPLP SFEAYTSLTY
     181 KVDMSTPLTT STQASSSPTT PESTTIPKST NSEGSTPLTS MPASTMKVAS SEAITLLTTP
     241 VEISTPVTIS AQASSSPTTA EGPSLSNSAP SGGSTPLTRM PLSVMLVVSS EASTLSTTPA
     301 ATNIPVITST EASSSPTTAE GTSIPTSTYT EGSTPLTSTP ASTMPVATSE MSTLSITPVD
     361 TSTLVTTSTE PSSLPTTAEA TSMLTSTLSE GSTPLTNMPV STILVASSEA STTSTIPVDS
     421 KTFVTTASEA SSSPTTAEDT SIATSTPSEG STPLTSMPVS TTPVASSEAS NLSTTPVDSK
     481 TQVTTSTEAS SSPPTAEVNS MPTSTPSEGS TPLTSMSVST MPVASSEAST LSTTPVDTST
     541 PVTTSSEASS SSTTPEGTSI PTSTPSEGST PLTNMPVSTR LVVSSEASTT STTPADSNTF
     601 VTTSSEASSS STTAEGTSMP TSTYSERGTT ITSMSVSTTL VASSEASTLS TTPVDSNTPV
     661 TTSTEATSSS TTAEGTSMPT STYTEGSTPL TSMPVNTTLV ASSEASTLST TPVDTSTPVT
     721 TSTEASSSPT TADGASMPTS TPSEGSTPLT SMPVSKTLLT SSEASTLSTT PLDTSTHITT
     781 STEASCSPTT TEGTSMPIST PSEGSPLLTS IPVSITPVTS PEASTLSTTP VDSNSPVTTS
     841 TEVSSSPTPA EGTSMPTSTY SEGRTPLTSM PVSTTLVATS AISTLSTTPV DTSTPVTNST
     901 EARSSPTTSE GTSMPTSTPG EGSTPLTSMP DSTTPVVSSE ARTLSATPVD TSTPVTTSTE
     961 ATSSPTTAEG TSIPTSTPSE GTTPLTSTPV SHTLVANSEA STLSTTPVDS NTPLTTSTEA
    1021 SSPPPTAEGT SMPTSTPSEG STPLTRMPVS TTMVASSETS TLSTTPADTS TPVTTYSQAS
    1081 SSSTTADGTS MPTSTYSEGS TPLTSVPVST RLVVSSEAST LSTTPVDTSI PVTTSTEASS
    1141 SPTTAEGTSI PTSPPSEGTT PLASMPVSTT LVVSSEANTL STTPVDSKTQ VATSTEASSP
    1201 PPTAEVTSMP TSTPGERSTP LTSMPVRHTP VASSEASTLS TSPVDTSTPV TTSAETSSSP
    1261 TTAEGTSLPT STTSEGSTLL TSIPVSTTLV TSPEASTLLT TPVDTKGPVV TSNEVSSSPT
    1321 PAEGTSMPTS TYSEGRTPLT SIPVNTTLVA SSAISILSTT PVDNSTPVTT STEACSSPTT
    1381 SEGTSMPNSN PSEGTTPLTS IPVSTTPVVS SEASTLSATP VDTSTPGTTS AEATSSPTTA
    1441 EGISIPTSTP SEGKTPLKSI PVSNTPVANS EASTLSTTPV DSNSPVVTST AVSSSPTPAE
    1501 GTSIAISTPS EGSTALTSIP VSTTTVASSE INSLSTTPAV TSTPVTTYSQ ASSSPTTADG
    1561 TSMQTSTYSE GSTPLTSLPV STMLVVSSEA NTLSTTPIDS KTQVTASTEA SSSTTAEGSS
    1621 MTISTPSEGS PLLTSIPVST TPVASPEAST LSTTPVDSNS PVITSTEVSS SPTPAEGTSM
    1681 PTSYTEGRT PLTSITVRTT PVASSAISTL STTPVDNSTP VTTSTEARSS PTTSEGTSMP
    1741 NSTPSEGTTP LTSIPVSTTP VLSSEASTLS ATPIDTSTPV TTSTEATSSP TTAEGTSIPT
    1801 STLSEGMTPL TSTPVSHTLV ANSEASTLST TPVDSNSPVV TSTAVSSSPT PAEGTSIATS
    1861 TPSEGSTALT SIPVSTTTVA SSETNTLSTT PAVTSTPVTT YAQVSSSPTT ADGSSMPTST
    1921 PREGRPPLTS IPVSTTTVAS SEINTLSTTL ADTRTPVTTY SQASSSPTTA DGTSMPTPAY
    1981 SEGSTPLTSM PLSTTLVVSS EASTLSTTPV DTSTPATTST EGSSSPTTAG GTSIQTSTPS
    2041 ERTTPLAGMP VSTTLVVSSE GNTLSTTPVD SKTQVTNSTE ASSSATAEGS SMTISAPSEG
    2101 SPLLTSIPLS TTPVASPEAS TLSTTPVDSN SPVITSTEVS SSPIPTEGTS MQTSTYSDRR
    2161 TPLTSMPVST TVVASSAIST LSTTPVDTST PVTNSTEARS SPTTSEGTSM PTSTPSEGST
    2221 PFTSMPVSTM PVVTSEASTL SATPVDTSTP VTTSTEATSS PTTAEGTSIP TSTLSEGTTP
    2281 LTSIPVSHTL VANSEVSTLS TTPVDSNTPF TTSTEASSPP PTAEGTSMPT STSSEGNTPL
    2341 TRMPVSTTMV ASFETSTLST TPADTSTPVT TYSQAGSSPT TADDTSMPTS TYSEGSTPLT
    2401 SVPVSTMPVV SSEASTHSTT PVDTSTPVTT STEASSSPTT AEGTSIPTSP PSEGTTPLAS
    2461 MPVSTTPVVS SEAGTLSTTP VDTSTPMTTS TEASSSPTTA EDIVVPISTA SEGSTLLTSI
    2521 PVSTTPVASP EASTLSTTPV DSNSPVVTST EISSSATSAE GTSMPTSTYS EGSTPLRSMP
    2581 VSTKPLASSE ASTLSTTPVD TSIPVTTSTE TSSSPTTAKD TSMPISTPSE VSTSLTSILV
    2641 STMPVASSEA STLSTTPVDT RTLVTTSTGT SSSPTTAEGS SMPTSTPGER STPLTNILVS
    2701 TTLLANSEAS TLSTTPVDTS TPVTTSAEAS SSPTTAEGTS MRISTPSDGS TPLTSILVST
    2761 LPVASSEAST VSTTAVDTSI PVTTSTEASS SPTTAEVTSM PTSTPSETST PLTSMPVNHT
    2821 PVASSEAGTL STTPVDTSTP VTTSTKASSS PTTAEGIVVP ISTASEGSTL LTSIPVSTTP
    2881 VASSEASTLS TTPVDSTPIPV TTSTEGSSSP TTAEGTSMPI STPSEVSTPL TSILVSTVPV
    2941 AGSEASTLST TPVDTRTPVT TSAEASSSPT TAEGTSMPIS TPGERRTPLT SMSVSTMPVA
    3001 SSEASTLSRT PADTSTPVTT STEASSSPTT AEGTGIPIST PSEGSTPLTS IPVSTTPVAI
    3061 PEASTLSTTP VDSNSPVVTS TEVSSSPTPA EGTSMPISTY SEGSTPLTGV PVSTTPVTSS
    3121 AISTLSTTPV DTSTPVTTST EAHSSPTTSE GTSMPTSTPS EGSTPLTYMP VSTMLVVSSE
```

Figure 8A

```
3181 DSTLSATPVD TSTPVTTSTE ATSSTTAEGT SIPTSTPSEG MTPLTSVPVS NTPVASSEAS
3241 ILSTTPVDSN TPLTTSTEAS SSPPTAEGTS MPTSTPSEGS TPLTSMPVST TTVASSETST
3301 LSTTPADTST PVTTYSQASS SPPIADGTSM PTSTYSEGST PLTNMSFSTT PVVSSEASTL
3361 STTPVDTSTP VTTSTEASLS PTTAEGTSIP TSSPSEGTTP LASMPVSTTP VVSSEVNTLS
3421 TTPVDSNTLV TTSTEASSSP TIAEGTSLPT STTSEGSTPL SIMPLSTTPV ASSEASTLST
3481 TPVDTSTPVT TSSPTNSSPT TAEVTSMPTS TAGEGSTPLT NMPVSTTPVA SSEASTLSTT
3541 PVDSNTFVTS SSQASSSPAT LQVTTMRMST PSEGSSSLTT MLLSSTYVTS SEASTPSTPS
3601 VDRSTPVTTS TQSNSTPTPP EVITLPMSTP SEVSTPLTIM PVSTTSVTIS EAGTASTLPV
3661 DTSTPVITST QVSSSPVTPE GTTMPIWTPS EGSTPLTTMP VSTTRVTSSE GSTLSTPSVV
3721 TSTPVTTSTE AISSSATLDS TTMSVSMPME ISTLGTTILV STTPVTRFPE SSTPSIPSVY
3781 TSMSMTTASE GSSSPTTLEG TTTMPMSTTS ERSTLLTTVL ISPISVMSPS EASTLSTPPG
3841 DTSTPLLTST KAGSFSIPAE VTTIRISITS ERSTPLTTLL VSTTLPTSFP GASIASTPPL
3901 DTSTTFTPST DTASTPTIPV ATTISVSVIT EGSTPGTTIF IPSTPVTSST ADVFPATTGA
3961 VSTPVITSTE LNTPSTSSSS TTTSFSTTKE FTTPAMTTAA PLTYVTMSTA PSTPRTTSRG
4021 CTTSASTLSA TSTPHTSTSV TTRPVTPSSE SSRPSTITSH TIPPTFPPAH SSTPPTTSAS
4081 STTVNPEAVT TMTTRTKPST RTTSFPTVTT TAVPTNTTIK SNPTSTPTVP RTTTCFGDGC
4141 QNTASRCKNG GTWDGLKCQC PNLYYGELCE EVVSSIDIGP PETISAQMEL TVTVTSVKFT
4201 EELKNHSSQE FQEFKQTFTE QMNIVYSGIP EYVGVNITKL RLGSVVVEHD VLLRTKYTPE
4261 YKTVLDNAXE VVKEKITKVT TQQIMINDIC SDMMCFNTTG TQVQNITVTQ YDPEEDCRKM
4321 AKEYGDYFVV EYRDQKPYCI SPCEPGFSVS KNCNLGKCQM SLSGPQCLCV TTETHWYSGE
4381 TCNQGTQKSL VYGLVGAGVV LMLIILVALL MLVFRSKREV KRQKYRLSQL YKWQEEDSGP
4441 APGTFQNIGF DICQDDDSIH LESIYSNFQP SLRHIDPETK IRIQRPQVMT TSF
```

Figure 8B

MUC17 Variant, SEQ ID NO: 4, 4262 aa
ORIGIN
```
       1 MPRPGTMALC LLTLVLSLLP PQAAAEQGLS VNRAVWDGGG CISQGDVLNR QCQQLSQHVR
      61 TGSATNTATG TTSTNVVEPR MYLSCSTNPE MTSIESSVTS DTPGVSSTRM TPTESRTTSE
     121 STSDSTTLFP SPTEDTSSPT TPEGTDVPMS TPSEESISST MAFVSTAPLP SFEAYTSLTY
     181 KVDMSTPLTT STQASSSPTT PESTTIPKST NSEGSTPLTS MPASTMKVAS SEAITLLTTP
     241 VEISTPVTIS AQASSSPTTA EGPSLSNSAP SGGSTPLTRM PLSVMLVVSS EASTLSTTPA
     301 ATNIPVITST EASSSPTTAE GTSIPTSTYT EGSTPLTSTP ASTMPVATSE MSTLSITPVD
     361 TSTLVTTSTE PSSLPTTAEA TSMLTSTLSE GSTPLTNMPV STILVASSEA STTSTIPVDS
     421 KTFVTTASEA SSSPTTAEDT SIATSTPSEG STPLTSMPVS TTPVASSEAS NLSTTPVDSK
     481 TQVTTSTEAS SSPPTAEVNS MPTSTPSEGS TPLTSMSVST MPVASSEAST LSTTPVDTST
     541 PVTTSSEASS SSTTPEGTSI PTSTPSEGST PLTNMPVSTR LVVSSEASTT STTPADSNTF
     601 VTTSSEASSS STTAEGTSMP TSTYSERGTT ITSMSVSTTL VASSEASTLS TTPVDSNTPV
     661 TTSTEATSSS TTAEGTSMPT STYTEGSTPL TSMPVNTTLV ASSEASTLST TPVDTSTPVT
     721 TSTEASSSPT TADGASMPTS TPSEGSTPLT SMPVSKTLLT SSEASTLSTT PLDTSTHITT
     781 STEASCSPTT TEGTSMPIST PSEGSPLLTS IPVSITPVTS PEASTLSTTP VDSNSPVTTS
     841 TEVSSSPTPA EGTSMPTSTY SEGRTPLTSM PVSTTLVATS AISTLSTTPV DTSTPVTNST
     901 EARSSPTTSE GTSMPTSTPG EGSTPLTSMP DSTTPVVSSE ARTLSATPVD TSTPVTTSTE
     961 ATSSPTTAEG TSIPTSTPSE GTTPLTSTPV SHTLVANSEA STLSTTPVDS NTPLTTSTEA
    1021 SSPPPTAEGT SMPTSTPSEG STPLTRMPVS TTMVASSETS TLSTTPADTS TPVTTYSQAS
    1081 SSSTTADGTS MPTSTYSEGS TPLTSVPVST RLVVSSEAST LSTTPVDTSI PVTTSTEASS
    1141 SPTTAEGTSI PTSPPSEGTT PLASMPVSTT LVVSSEANTL STTPVDSKTQ VATSTEASSP
    1201 PPTAEVTSMP TSTPGERSTP LTSMPVRHTP VASSEASTLS TSPVDTSTPV TTSAETSSSP
    1261 TTAEGTSLPT STTSEGSTLL TSIPVSTTLV TSPEASTLLT TPVDTKGPVV TSNEVSSSPT
    1321 PAEGTSMPTS TYSEGRTPLT SIPVNTTLVA SSAISILSTT PVDNSTPVTT STEACSSPTT
    1381 SEGTSMPNSN PSEGTTPLTS IPVSTTPVVS SEASTLSATP VDTSTPGTTS AEATSSPTTA
    1441 EGISIPTSTP SEGKTPLKSI PVSNTPVANS EASTLSTTPV DSNSPVVTST AVSSSPTPAE
    1501 GTSIAISTPS EGSTALTSIP VSTTTVASSE INSLSTTPAV TSTPVTTYSQ ASSSPTTADG
    1561 TSMQTSTYSE GSTPLTSLPV STMLVVSSEA NTLSTTPIDS KTQVTASTEA SSSTTAEGSS
    1621 MTISTPSEGS PLLTSIPVST TPVASPEAST LSTTPVDSNS PVITSTEVSS SPTPAEGTSM
    1681 PTSTYTEGRT PLTSITVRTT PVASSAISTL STTPVDNSTP VTTSTEARSS PTTSEGTSMP
    1741 NSTPSEGTTP LTSIPVSTTP VLSSEASTLS ATPIDTSTPV TTSTEATSSP TTAEGTSIPT
    1801 STLSEGMTPL TSTPVSHTLV ANSEASTLST TPVDSNSPVV TSTAVSSSPT PAEGTSIATS
    1861 TPSEGSTALT SIPVSTTTVA SSETNLSTT PAVTSTPVTT YAQVSSSPTT ADGSSMPTST
    1921 PREGRPPLTS IPVSTTTVAS SEINTLSTTL ADTRTPVTTY SQASSSPTTA DGTSMPTPAY
    1981 SEGSTPLTSM PLSTTLVVSS EASTLSTTPV DTSTPATTST EGSSSPTTAG GTSIQTSTPS
    2041 ERTTPLAGMP VSTTLVVSSE GNTLSTTPVD SKTQVTNSTE ASSSATAEGS SMTISAPSEG
    2101 SPLLTSIPLS TTPVASPEAS TLSTTPVDSN SPVITSTEVS SSPIPTEGTS MQTSTYSDRR
    2161 TPLTSMPVST TVVASSAIST LSTTPVDTST PVTNSTEARS SPTTSEGTSM PTSTPSEGST
    2221 PFTSMPVSTM PVVTSEASTL SATPVDTSTP VTTSTEATSS PTTAEGTSIP TSTLSEGTTP
    2281 LTSIPVSHTL VANSEVSTLS TTPVDSNTPF TTSTEASSPP PTAEGTSMPT STSSEGNTPL
    2341 TRMPVSTTMV ASFETSTLST TPADTSTPVT TYSQAGSSPT TADDTSMPTS TYSEGSTPLT
    2401 SVPVSTMPVV SSEASTHSTT PVDTSTPVTT STEASSSPTT AEGTSIPTSP PSEGTTPLAS
    2461 MPVSTTPVVS SEAGTLSTTP VDTSTPMTTS TEASSSPTTA EDIVVPISTA SEGSTLLTSI
    2521 PVSTTPVASP EASTLSTTPV DSNSPVVTST EISSSATSAE GTSMPTSTYS EGSTPLRSMP
    2581 VSTKPLASSE ASTLSTTPVD TSIPVTTSTE TSSSPTTAKD TSMPISTPSE VSTSLTSILV
    2641 STMPVASSEA STLSTTPVDT RTLVTTSTGT SSSPTTAEGS SMPTSTPGER STPLTNILVS
    2701 TTLLANSEAS TLSTTPVDTS TPVTTSAEAS SSPTTAEGTS MRISTPSDGS TPLTSILVST
    2761 LPVASSEAST VSTTAVDTSI PVTTSTEASS SPTTAEVTSM PTSTPSETST PLTSMPVNHT
    2821 PVASSEAGTL STTPVDTSTP VTTSTKASSS PTTAEGIVVP ISTASEGSTL LTSIPVSTTP
    2881 VASSEASTLS TTPVDTSIPV TTSTEGSSSP TTAEGTSMPI STPSEVSTPL TSILVSTVPV
    2941 AGSEASTLST TPVDTRTPVT TSAEASSSPT TAEGTSMPIS TPGERRTPLT SMSVSTMPVA
    3001 SSEASTLSRT PADTSTPVTT STEASSSPTT AEGTGIPIST PSEGSTPLTS IPVSTTPVAI
    3061 PEASTLSTTP VDSNSPVVTS TEVSSSPTPA EGTSMPISTY SEGSTPLTGV PVSTTPVTSS
    3121 AISTLSTTPV DTSTPVTTST EAHSSPTTSE GTSMPTSTPS EGSTPLTYMP VSTMLVVSSE
```

Figure 9A

```
3181 DSTLSATPVD TSTPVTTSTE ATSSTTAEGT SIPTSTPSEG MTPLTSVPVS NTPVASSEAS
3241 ILSTTPVDSN TPLTTSTEAS SSPPTAEGTS MPTSTPSEGS TPLTSMPVST TTVASSETST
3301 LSTTPADTST PVTTYSQASS SPPIADGTSM PTSTYSEGST PLTNMSFSTT PVVSSEASTL
3361 STTPVDTSTP VTTSTEASLS PTTAEGTSIP TSSPSEGTTP LASMPVSTTP VVSSEVNTLS
3421 TTPVDSNTLV TTSTEASSSP TIAEGTSLPT STTSEGSTPL SIMPLSTTPV ASSEASTLST
3481 TPVDTSTPVT TSSPTNSSPT TAEVTSMPTS TAGEGSTPLT NMPVSTTPVA SSEASTLSTT
3541 PVDSNTFVTS SSQASSSPAT LQVTTMRMST PSEGSSSLTT MLLSSTYVTS SEASTPSTPS
3601 VDRSTPVTTS TQSNSTPTPP EVITLPMSTP SEVSTPLTIM PVSTTSVTIS EAGTASTLPV
3661 DTSTPVITST QVSSSPVTPE GTTMPIWTPS EGSTPLTTMP VSTTRVTSSE GSTLSTPSVV
3721 TSTPVTTSTE AISSSATLDS TTMSVSMPME ISTLGTTILV STTPVTRFPE SSTPSIPSVY
3781 TSMSMTTASE GSSSPTTLEG TTTMPMSTTS ERSTLLTTVL ISPISVMSPS EASTLSTPPG
3841 DTSTPLLTST KAGSFSIPAE VTTIRISITS ERSTPLTTLL VSTTLPTSFP GASIASTPPL
3901 DTSTTFTPST DTASTPTIPV ATTISVSVIT EGSTPGTTIF IPSTPVTSST ADVFPATTGA
3961 VSTPVITSTE LNTPSTSSSS TTTSFSTTKE FTTPAMTTAA PLTYVTMSTA PSTPRTTSRG
4021 CTTSASTLSA TSTPHTSTSV TTRPVTPSSE SSRPSTITSH TIPPTFPPAH SSTPPTTSAS
4081 STTVNPEAVT TMTTRTKPST RTTSFPTVTT TAVPTNTTIK SNPTSTPTVP RTTTCFGDGC
4141 QNTASRCKNG GTWDGLKCQC PNLYYGELCE EVVSSIDIGP PETISAQMEL TVTVTSVKFT
4201 EELKNHSSQE FQEFKQTFTE QMNIVYSGIP EYVGVNITKL RHDVFQHHWH PSAKHYGDPV
4261 RP
//
```

Figure 9B

MUC17 ENCODING NUCLEIC ACID SEQUENCES, POLYPEPTIDES, ANTIBODIES AND METHODS OF USE THEREOF

GOVERNMENT RIGHTS

Pursuant to 35 U.S.C. §202(c), it is acknowledged that the U.S. Government has certain rights in the invention described herein, which was made in part with funds from the National Institutes of Health, Grant Number: 5 RO1-CA078590-06.

FIELD OF THE INVENTION

This invention relates to the fields of molecular biology and oncology. Specifically, the invention provides MUC17 encoding nucleic acid sequences, polypeptides, antibodies, and methods of use thereof.

BACKGROUND OF THE INVENTION

Several publications and patents are cited in this application in order to more fully describe the state of the art to which this invention pertains. The disclosure of each of these citations is incorporated by reference herein.

Adenocarcinoma of pancreatic ducts is the fifth leading cause of cancer-related deaths in the United States (1;2). The survival time for patients diagnosed with pancreatic cancer ranges from three to six months on average, with a 5% chance of five-year survival. The highest cure rate occurs if the tumor is truly localized to the pancreas; however, this stage of disease accounts for fewer than 20% of cases. For those patients with localized disease and small cancers (<2 centimeters), with no lymph node metastases and no extension beyond the "capsule" of the pancreas, complete surgical resection can yield actuarial 5-year survival rates of 18% to 24% (3;4). Unfortunately, the signs of early stage pancreatic cancer are vague, and often attributed to other problems by both patients and physicians. More specific symptoms tend to develop after the tumor has grown to invade other organs or blocked the bile ducts. Patients are usually diagnosed at an advanced stage, with a high incidence of associated metastases, which spread throughout the body.

There are no tumor-specific markers for pancreatic cancer; markers such as serum CA19-9 have low specificity (5). 65% of patients with pancreatic cancer will have CA19-9 levels greater than 120 U/L, whereas only 2% of cases of pancreatitis will have levels this high. Indeed, CA-19-9 levels increase with pancreatic cancer (97%) to values greater than 1000 U/L, however most of these cancers will be unresectable. Anti-CA19-9 recognizes a mucin-type glycoprotein sialosyl lewis antigen (6). For over two decades, oligosaccharide structure antigens such as CA19-9, DUPAN2, or CA125 were heavily investigated for the development of serum-based immunoassays for the early detection of cancers. These saccharidic epitopes are carried by high molecular weight glycoproteins called mucins. CA19-9 (7;8) and DUPAN2 (7;9) are present in MUC1 and CA125 is present in MUC16 (10; 11).

Interestingly, both mucin gene expression and the glycosylation pattern of mucins are dysregulated in cancer development and progression. Indeed, a specific mucin expression pattern is usually associated with one type of adenocarcinoma, which is distinct from its normal counterpart. For instance, it has previously been reported that overexpression of the MUC1 gene and aberrant expression of the MUC4 gene is associated with pancreatic cancer development and progression. MUC4 is highly expressed in human pancreatic tumors and pancreatic tumor cell lines, but is minimally or not expressed in normal pancreas or chronic pancreatitis (12–15). MUC4 is expressed by metasplastic ducts and its expression increases with higher grade in Pancreatic intraepithelial neoplasias (PanINs) (16). However, MUC4 is expressed by only 70 to 75% of the pancreatic tumors studied.

Mucins, the main components of the mucus network, are high molecular weight O-glycoproteins expressed and secreted by epithelial cells and in some case by endothelial cells. Their principal function is to protect and lubricate epithelial surfaces, and recent reports demonstrate that mucins and more specifically membrane-bound mucins might play a key role in the initiation and transduction of signals, which trigger apoptosis and/or proliferation. The rMuc4 (rat homologue of human MUC4) forms a ligand-receptor type intramembrane complex with HER2, induces its phosphorylation and triggers survival of cells by repression of apoptosis (17).

Currently, nineteen genes are within the MUC gene family and include: MUC1–2, MUC3, MUC4, MUC5AC, MUC5B, MUC6–13, MUC15–19 (18–22). These mucins can further be grouped in two subfamilies, e.g. secreted mucins and membrane-bound mucins. Secreted mucins are expressed exclusively by specialized epithelial cells, are secreted in the mucus, and demonstrate a restricted expression pattern within the human body. Membrane-bound mucins, composed of MUC1, MUC3, MUC4, MUC12–13, MUC16, and MUC17 often possess EGF-like domains (MUC3, 4, 12, 13, and 17) and appear to share numerous common properties. As compared to the secreted mucins, membrane-bound mucins demonstrate a wide and complex expression pattern. They can be expressed in four distinct forms; 1) membrane-anchored, 2) soluble (proteolytic cleavage of the membrane-bound form), 3) secreted (alternative splice variants), and 4) lacking the tandem repeat array (alternatively spliced variants) (14;23–26). The ratio of one form to another appears to be tissue specific as is association with the physiologic condition, e.g.,(normal or malignant phenotypes) (26;27).

SUMMARY OF THE INVENTION

In accordance with the present invention, methods and compositions for detecting pancreatic cancer are provided. Specifically, two MUC17 encoding nucleic acids are disclosed, as well as methods of detecting pancreatic cancer by detecting elevations in expression levels of the same.

One embodiment of the invention comprises an isolated, enriched, or purified nucleic acid molecule encoding MUC17 or a secreted variant thereof designated as MUC17sec herein. Exemplary nucleic acids encoding these MUC17 proteins have the sequences of SEQ ID NOS 1 and 2 and encode MUC 17 proteins of SEQ ID NOS: 3 and 4 respectively.

Also provided in accordance with the invention are oligonucleotides, including probes and primers, that specifically hybridize with the nucleic acid sequences set forth above.

In a further aspect of the invention, recombinant DNA molecules comprising the nucleic acid molecules set forth above, operably linked to a vector are provided. The invention also encompasses host cells comprising a vector encoding the MUC17 polypeptides of the invention.

One embodiment of the invention comprises an isolated, enriched, or purified MUC17 polypeptide. Preferably, the MUC17 polypeptide is full length or an alternatively spliced secreted variant. Most preferably, a MUC17 polypeptide is the polypeptide encoded by SEQ ID NOS:1 or 2, or is the polypeptide of SEQ ID NO:3 or 4.

In another aspect of the invention, an antibody immunologically specific for a MUC 17 polypeptide is provided. Such antibodies may be monoclonal or polyclonal, and include recombinant, chimerized, humanized, antigen binding fragments of such antibodies, and anti-idiotypic antibodies.

In another aspect of the invention, methods for detecting MUC17 associated molecules in a biological sample are provided. Such molecules can be MUC17 encoding nucleic acids, such as mRNA, DNA, cDNA, or MUC17 encoded polypeptides or fragments thereof. Exemplary methods comprise mRNA analysis, for example by RT-PCR. Immunological methods include for example contacting a sample with a detectably labeled antibody immunologically specific for a MUC17 polypeptide and determining the presence of the polypeptide as a function of the amount of detectably labeled antibody bound by the sample relative to control cells. In a preferred embodiment, these assays may be used to detect MUC17 or the secreted variant thereof. In a most preferred embodiment, assays which detect MUC17 are used to diagnose pancreatic cancer. In an alternative embodiment of the method, MUC 4 and MUC 12 expression levels are also examined as these mucins have previously been associated with the occurrence of pancreatic cancer.

In another aspect of the invention, recombinant organisms, or transgenic organisms which have a new combination of genes or nucleic acid molecules are provided.

In a further aspect of the invention, kits for detection of pancreatic cancer are provided. An exemplary kit comprises a MUC17 protein, polynucleotide, or antibody, which are optionally linked to a detectable label. The kits may also include a pharmaceutically acceptable carrier and/or excipient, a suitable container, and instructions for use.

BRIEF DESCRIPTION OF THE DRAWINGS

FIG. 1 is a pair of gels showing the expression of membrane-bound mucin genes in normal pancreas and pancreatitis tissue samples. Total RNA from two normal pancreatic and eight pancreatitis tissue samples were analyzed by RT-PCR using primers specific for MUC1, 3, 4, 12, 13, 16, and 17. β actin was used as internal control. Only MUC1 and MUC13 were detected in the normal pancreas specimen while MUC1, MUC13, and MUC16 were detected in the pancreatitis tissue samples.

FIGS. 6A–6G show the nucleotide sequence of MUC17-encoding sequence, SEQ ID NO: 1.

FIGS. 7A–7G show the nucleotide sequence of MUC17SEC-encoding sequence, SEQ ID NO: 2.

FIGS. 8A and 8B show the amino acid sequence of MUC17 protein, SEQ ID NO: 3.

FIGS. 9A and 9B show the amino acid sequence of MUC17SEC protein, SEQ ID NO: 4.

DETAILED DESCRIPTION OF THE INVENTION

Figure 2:
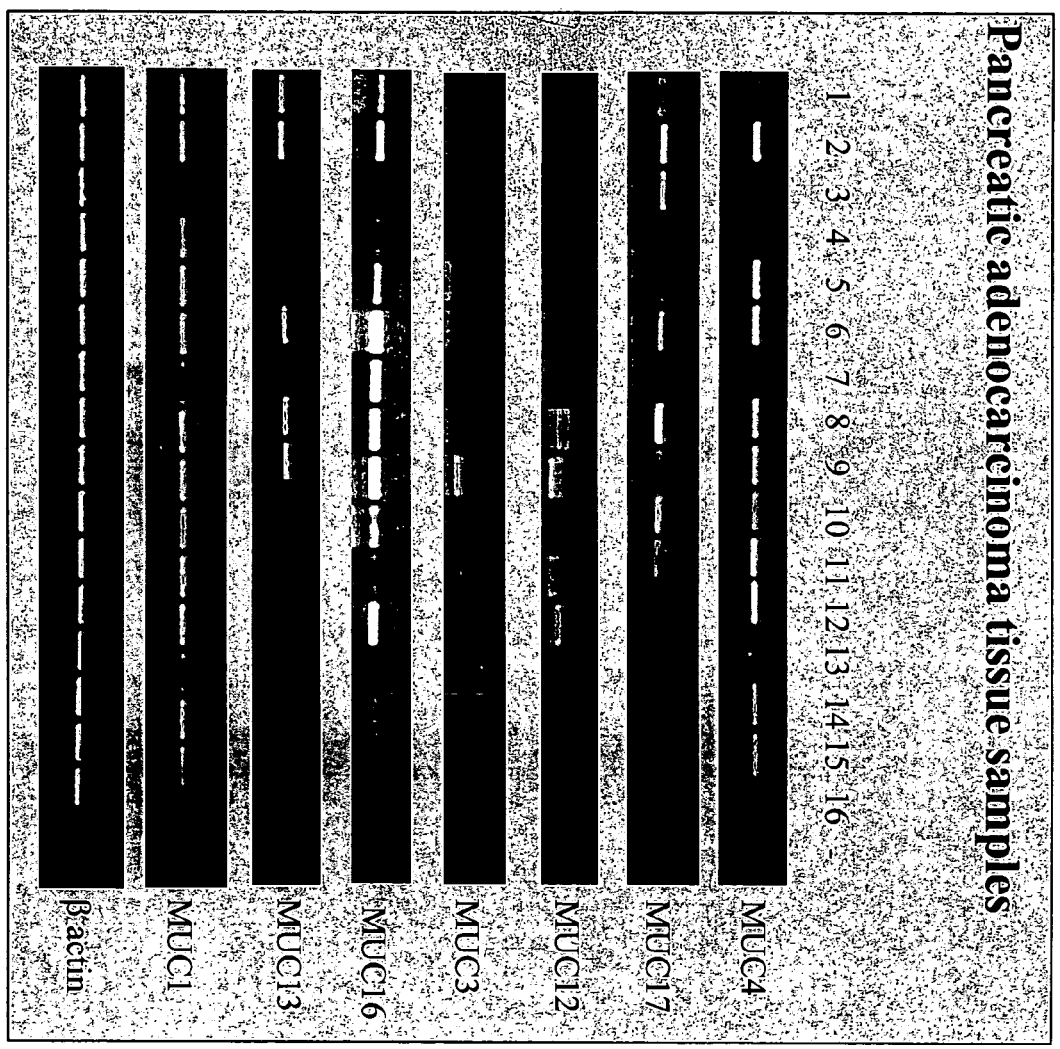
FIG. 2 is a gel showing the expression of membrane-bound mucin genes in sixteen pancreatic adenocarcinoma tissue samples. Total RNAs were prepared using the guanidinium isothiocyanate-cesium chloride ultracentrifugation method and analyzed by RT-PCR. β actin was used as internal control. MUC1, MUC13, and MUC16 were detected respectively in 100, 56, and 95% of the samples. As disclosed previously (28), MUC4 was detected in 93% of the samples. MUC3, MUC12, and MUC17 were expressed in 6, 75, and 87% of the specimens tested.

The present invention relates to the discovery of full-length MUC17-encoding sequence (SEQ ID NO: 1) and a variant MUC17SEC-encoding sequence (SEQ ID NO: 2), which encode the full-length MUC17 protein (SEQ ID NO: 3) and a variant MUC17 secreted protein (SEQ ID NO: 4), respectively. The present invention also relates to antibodies having binding affinity for MUC17 or MUC17SEC protein. As used herein, a "MUC17 protein" or "MUC17 polypeptide" may refer to both the MUC17 protein of SEQ ID NO: 3 and the variant MUC17SEC protein of SEQ ID NO: 4.

The present invention further relates to methods for diagnosing pancreatic caner in patients by detecting the expression levels of MUC17 related molecules which include without limitation MUC17 acids. (e.g. DNA and RNA) and MUC17 proteins or polypeptides. The method optionally includes detecting the expression levels of other mucin genes, such as MUC4 and MUC12.

Also encompassed within the invention are kits for performing the methods described above.

I. Preparation of Human MUC17-Encoding Nucleic Acid Molecules, MUC 17 Proteins, and Antibodies thereto Nucleic Acid Molecules: Nucleic acid molecules encoding the human MUC17 proteins of the invention may be prepared by two general methods: (1) synthesis from appropriate nucleotide triphosphates, or (2) isolation from biological sources. Both methods utilize protocols well known in the art. The availability of nucleotide sequence information, such as cDNAs having the sequences of SEQ ID NOs: 1 and 2, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 14 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 14 kb double-stranded molecule. A synthetic DNA molecule so constructed may then be cloned and amplified in an appropriate vector. Nucleic acid sequences encoding the human MUC17 protein may be isolated from appropriate biological sources using methods known in the art. In a preferred embodiment, a cDNA clone is isolated from a cDNA expression library of human origin. In an alternative embodiment, utilizing the sequence information provided by the cDNA sequence, human genomic clones encoding MUC17 proteins may be isolated. Suitable probes for this purpose are derived from sequences within the MUC17 cDNAs.

Additionally, cDNAs or genomic clones having homology with human MUC17 may be isolated from other species using oligonucleotide probes corresponding to predetermined sequences within the human MUC17 encoding nucleic acids.

In accordance with the present invention, nucleic acids having the appropriate level of sequence homology with the protein coding region of SEQ ID NOs: 1 or 2 may be identified by using hybridization and washing conditions of appropriate stringency. For example, hybridizations may be performed, according to the method of Sambrook et al., *Molecular Cloning*, Cold Spring Harbor Laboratory (1989), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows:

$$T_m=81.5° C.+16.6 \text{ Log } [Na+]+0.41(\% G+C)-0.63 (\% \text{ formamide})-600/\#bp \text{ in duplex}$$

As an illustration of the above formula, using $[Na^+]$= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1×SSC and 0.5% SDS at 65° C. for 15 minutes.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell.

MUC17-encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention, such as selected segments of the cDNA having SEQ ID NOs: 1 or 2. As mentioned previously, such oligonucleotides are useful as probes for detecting or isolating MUC17 genes.

Antisense nucleic acid molecules may be targeted to translation initiation sites and/or splice sites to inhibit the expression of the MUC17 gene or production of the MUC17 protein of the invention. Such antisense molecules are typically between 15 and 30 nucleotides in length and often span the translational start site of MUC17 encoding mRNA molecules.

Alternatively, antisense constructs may be generated which contain the entire MUC17 cDNAs in reverse orientation. Such antisense constructs are endompassed by the present invention.

It will be appreciated by persons skilled in the art that variants (e.g., allelic variants) of MUC17 sequences exist in the human population, and must be taken into account when designing and/or utilizing oligonucleotides of the invention. Accordingly, it is within the scope of the present invention to encompass such variants, with respect to the MUC17 sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants. Additionally, the term "substantially complementary" refers to oligonucleotide sequences that may not be perfectly matched to a target sequence, but such mismatches do not materially affect the ability of the oligonucleotide to hybridize with its target sequence under the conditions described.

Proteins: Full-length human MUC17 protein (SEQ ID NO: 3) and its variant MUC17SEC protein (SEQ ID NO: 4) of the present invention may be prepared in a variety of ways, according to known methods. The protein may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding MUC17 and MUC17SEC proteins enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or Gibco-BRL, Gaithersburg, Md.

Alternatively, according to a preferred embodiment, larger quantities of MUC17 or MUC17SEC proteins may be produced by expression in a suitable prokaryotic or eukaryotic system. For example, part or all of a DNA molecule, such as a cDNA having SEQ ID NOs: 1 or 2 may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

The human MUC17 protein (SEQ ID NO: 3) or its variant form (SEQ ID NO: 4) produced by gene expression in a recombinant procaryotic or eukaryotic system may be purified according to methods known in the art. In a preferred embodiment, a commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope or the hemagglutinin epitope. Such methods are commonly used by skilled practitioners.

The human MUC17 protein and its variant, prepared by the aforementioned methods, may be analyzed according to standard procedures. For example, such proteins may be subjected to amino acid sequence analysis, according to known methods.

Antibodies: The present invention also provides antibodies capable of immunospecifically binding to proteins of the invention. Polyclonal antibodies directed toward human MUC17 proteins may be prepared according to standard methods. In a preferred embodiment, monoclonal antibodies are prepared, which react immunospecifically with the various epitopes of the MUC17 proteins described herein. Monoclonal antibodies may be prepared according to general methods of Köhler and Milstein, following standard protocols. Polyclonal or monoclonal antibodies that immunospecifically interact with MUC17 proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-MUC17 antibodies are described below.

II. Uses of MUC17-Encoding Nucleic Acids, MUC17 Proteins and Antibodies thereto

In accordance with the present invention, MUC4, MUC12, and MUC17 are specifically up-regulated in pancreatic adenocarcinoma specimens (FIGS. 1 and 2). Thus, the MUC17 nucleic acids, proteins, and anti-MUC17 antibodies may be used for diagnosing pancreatic cancer in patients.

Additionally, the methods for diagnosing pancreatic cancer may further comprise assessing MUC4 and/or MUC12 expression levels in the patients. The nucleic acid sequences encoding human MUC4 and MUC12 are available in GenBank. MUC 4 Accession numbers are AJ276359, AJ100901 and AJ000281. The MUC12 Accession number is AF147790.

MUC17-Encoding Nucleic Acids: MUC17-encoding nucleic acids may be used for a variety of purposes in accordance with the present invention. MUC17-encoding DNA, RNA, or fragments thereof may be used as probes to detect the presence of and/or expression of genes encoding MUC17 proteins. Methods in which MUC17-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR). Thus, MUC17-encoding nucleic acids of the present invention may be used for detecting up-regulation of MUC17 genes in patients and thereby determining the presence of pancreatic carcinoma in the patients.

Further, the MUC17-encoding nucleic acids of the invention may also be utilized as probes to identify related genes from other animal species. As is well known in the art, hybridization stringencies may be adjusted to allow hybridization of nucleic acid probes with complementary sequences of varying degrees of homology.

Thus, MUC17-encoding nucleic acids may be used to advantage to identify and characterize other genes of varying degrees of relation to the MUC17 genes of the invention thereby enabling further identification of genes whose up-regulation is associated with pancreatic adenocarcinomas. Additionally, the nucleic acids of the invention may be used to identify genes encoding proteins that interact with MUC17 proteins (e.g., by the "interaction trap" technique).

Nucleic acid molecules, or fragments thereof, encoding MUC17 genes may also be utilized to control the production of MUC17 proteins in target cells. As mentioned above, antisense oligonucleotides corresponding to essential processing sites in MUC17-encoding mRNA molecules may be utilized to inhibit MUC17 protein production in targeted cells. Alterations in the physiological amount of MUC17 proteins may dramatically affect the activity of other protein factors involved in the progression of pancreatic carcinoma.

The MUC17 nucleic acids of the invention may be introduced into host cells. In a preferred embodiment, mammalian cell lines are provided which comprise a MUC17-encoding nucleic acid or a variant thereof. Host cells contemplated for use include, but are not limited to NIH3T3, CHO, HELA, yeast, bacteria, insect and plant cells. The MUC17 encoding nucleic acids may be operably linked to appropriate regulatory expression elements suitable for the particular host cell to be utilized. Methods for introducing nucleic acids into host cells are well known in the art. Such methods include, but are not limited to, transfection, transformation, calcium phosphate precipitation, electroporation and lipofection.

The host cells described above may be used as screening tools to identify compounds that modulate MUC17 expression and/or activity. Modulation of MUC17 expression and/or activity may be assessed by measuring alterations in MUC17 mRNA or protein levels in the presence of the test compound.

The availability of MUC17 encoding nucleic acids enables the production of strains of laboratory mice carrying part or all of the MUC17 gene or mutated sequences thereof, in single or amplified copies. Such mice may provide an in vivo model for cancer, and may be particularly useful in studying pancreatic cancer. Alternatively, the human MUC17 nucleic acid sequence information provided herein enables the cloning of the murine homolog for use in the production of knockout mice in which the endogenous gene encoding MUC17 has been specifically inactivated. Methods of introducing transgenes and knockouts in laboratory mice are known to those of skill in the art. Three common methods include: 1) integration of retroviral vectors encoding the foreign gene of interest into an early embryo; 2) injection of DNA into the pronucleus of a newly fertilized egg; and 3) the incorporation of genetically manipulated embryonic stem cells into an early embryo. Production of the transgenic and knockout mice described above will facilitate the molecular elucidation of the role MUC17 proteins play in differentiation and tumorigenesis.

The alterations to the MUC17 gene envisioned herein include modifications, deletions, and substitutions. Modifications and deletions render the naturally occurring gene nonfunctional, producing a "knock out" animal. Substitutions of the naturally occurring gene for a gene from a second species results in an animal that produces a MUC17 gene from the second species. Substitution of the naturally occurring gene for a gene having a mutation results in an animal with a mutated MUC17 protein. A transgenic mouse carrying the human MUC17 gene is generated by direct replacement of the mouse MUC17 gene with the human gene. These transgenic animals are valuable for use in vivo assays for elucidation of other medical disorders associated with cellular activities modulated by MUC17 genes. A transgenic animal carrying a "knock out" of a MUC17-encoding nucleic acid is useful for the establishment of a nonhuman model for pancreatic cancer involving MUC17 regulation.

As a means to define the role that MUC17 plays in mammalian systems, mice can be generated that cannot make MUC17 proteins because of a targeted mutational disruption of a MUC17 gene.

The term "animal" as used in this section includes all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered MUC17 gene generally should not fully encode the same MUC17 protein native to the host animal and its expression product should be altered to a minor or great degree, or absent altogether. However, it is conceivable that a more modestly modified MUC17 gene will fall within the scope of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof. A preferred type of target cell for transgene introduction is the embryonal stem (ES) cell. ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated MUC17 genes to selectively inactivate the wild-type gene in totipotent ES cells (such as those described above) and then generate transgenic mice. The use of gene-targeted ES cells in the generation of gene-targeted transgenic mice is known in the art.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Knockout mice of the invention can be injected with tumor cells or treated with carcinogens to generate carcinomas. Such mice provide a biological system for assessing the role played by a MUC17 gene of the invention. Accordingly, therapeutic agents which inhibit the expression and/or action of MUC17 proteins may be screened in studies using MUC17 knock out mice.

As described above, MUC17-encoding nucleic acids are also used to advantage to produce large quantities of substantially pure MUC17 proteins, or selected portions thereof.

MUC17 Protein and Antibodies: Purified MUC17 protein, or fragments thereof, may be used to produce polyclonal or monoclonal antibodies which also may serve as sensitive detection reagents for the presence and accumulation of MUC17 protein (or complexes containing MUC17 protein) in mammalian cells. Recombinant techniques enable expression of fusion proteins containing part or all of MUC17 protein. The full length protein or fragments of the protein may be used to advantage to generate an array of monoclonal antibodies specific for various epitopes of MUC17 protein, thereby providing even greater sensitivity for detection of MUC17 protein in cells.

Polyclonal or monoclonal antibodies immunologically specific for MUC17 protein may be used in a variety of assays designed to detect and quantitate the protein. Such assays include, but are not limited to: (1) flow cytometric analysis; (2) immunochemical detection/localization of MUC17 protein in tumor cells or cells in various stages of differentiation; and (3) immunoblot analysis (e.g., dot blot, Western blot) of extracts from various cells. Additionally, as described above, anti-MUC17 antibodies can be used for purification of MUC17 protein and any associated subunits (e.g., affinity column purification, immunoprecipitation).

From the foregoing discussion, it can be seen that MUC17-encoding nucleic acids, MUC17 expressing vectors, MUC17 protein and anti-MUC17 antibodies of the invention can be used to detect MUC17 gene expression and alter MUC17 protein accumulation.

Methods of Use for the Compositions of the Invention and Kits for Performing the Disclosed Methods:

Exemplary approaches for detecting MUC17 nucleic acids or polypeptides/proteins include:

a) comparing the amount of MUC17 mRNAs in the sample from a patient suspecting having pancreatic cancer with that from a healthy subject without pancreatic cancer; or b) comparing the amount of MUC17 proteins in the sample from a patient suspecting having pancreatic cancer with that from a healthy subject without pancreatic cancer; or c) using a specific binding member capable of binding to a MUC17 nucleic acid sequence or the polypeptide encoded by it, the specific binding member comprising nucleic acid hybridizable with the MUC17 sequence, or substances comprising an antibody domain with specificity for MUC17 nucleic acid sequence or the polypeptide encoded by it, the specific binding member being labelled so that binding of the specific binding member to its binding partner is detectable and/or quantifiable.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair comprise nucleic acid sequences, they will be of a length to hybridize to each other under conditions of the assay, preferably greater than 10 nucleotides long, more preferably greater than 15 or 20 nucleotides long.

In most embodiments for screening for cancer, the MUC17 nucleic acid in the sample will initially be amplified, e.g. using RT-PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides.

In terms of antigen detection, the biological sample analyzed may be any sample that is suspected of containing the MUC17 antigen, such as a pancreas or lymph node tissue section or specimen, a homogenized tissue extract, an isolated cell, a cell membrane preparation, separated or purified forms of any of the above protein-containing compositions, or even any biological fluid that comes into contact with pancreatic tissues, including blood and lymphatic fluid.

Contacting the chosen biological sample with the antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any MUC17 antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art. The immunodetection methods of the present invention have evident utility in the diagnosis of pancreatic cancer.

In the clinical diagnosis or monitoring of patients with pancreatic cancer, the detection of MUC17 antigen, or an increase in the levels of such an antigen, in comparison to the levels in a corresponding biological sample from a normal subject is indicative of a patient with pancreatic cancer. The basis for such diagnostic methods lies, in part, with the finding that the MUC17 nucleic acid identified in the present invention is overexpressed in pancreatic cancer tissue samples (see Examples below). By extension, it may be inferred that this nucleic acid produces elevated levels of encoded MUC17 proteins which may also be used as pancreatic cancer markers.

As mentioned previously, cell lines expressing the MUC17-encoding nucleic acids or variants thereof may be used in screening methods to identify agents which modulate MUC17 expression and/or function.

In one broad aspect, the present invention encompasses kits for use in detecting expression of MUC17 in pancreatic tissues. Such a kit may comprise one or more pairs of primers for amplifying nucleic acids corresponding to the MUC17 gene. The kit may further comprise samples of total mRNA derived from tissue of various physiological states, such as normal, early stage and metastatically progressive tumor, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting pancreatic cancer cells in a biological sample comprising oligonucleotide probes effective to bind with high affinity to MUC17 mRNA in a Northern blot assay and containers for each of these probes. In a further embodiment, the invention encompasses a kit for use in detecting MUC17 proteins in pancreatic cancer cells comprising antibodies specific for MUC17 proteins encoded by the MUC17 nucleic acids of the present invention.

Further details regarding the practice of this invention are set forth in the following examples, which are provided for illustrative purposes only and are in no way intended to limit the invention. The following materials and methods are provided to facilitate the practice of the present invention.

Tissue specimens and cell lines—A total of 24 pancreatic adenocarcinomas, 10 pancreatitis tissue samples (all obtained at the time of primary surgery from various patients) and 2 normal pancreatic tissue samples (obtained from previously healthy organ donors) were used in this study. Samples were collected under the protocol approved by the Institutional Review Board at the University of Nebraska Medical Center, Omaha, Nebr., and the Department of Visceral and Transplantation Surgery, University of Bern, Bern, Switzerland. Informed consent was obtained from all subjects. Tissue specimens were frozen in liquid nitrogen and stored at −80° C. until they were processed for RNA extraction.

RNA isolation and reverse transcription RT-PCR analysis—Total RNA was isolated from tissue samples and cell lines by the guanidinium isothiocyanate-cesium chloride ultracentrifugation method (28). Two micrograms of RNA were reverse transcribed using the SuperScript™II RNase Reverse Transcriptase system (Invitrogen, USA) Samples were subjected to PCR amplification using the parameters and primers described previously (12;29). Additional primers were: MUC12 (forward GCACATGTCAGCTG-CAACGCA; SEQ ID NO: 5, reverse GGCTCTGTGTTTG-CAGCTCTC; SEQ ID NO: 6), MUC13 (forward AACTGCTAGCACCACAGCAA; SEQ ID NO: 7, reverse CTCAGTCACAGTCTTCTCATT: SEQ ID NO: 8), MUC16 (forward CAGTCAACTACATGACACATT; SEQ ID NO: 9, reverse ACTCTGTCTACTCTCCGAGCC; SEQ ID NO: 10), MUC17 (forward GACCAGAAGCCATACT-GCATC; SEQ ID NO: 11, reverse CTCCTCACTCCCA-GACTTCTC; SEQ ID NO: 12). β-actin was used as an internal control. PCR products were electrophoretically resolved on 1% agarose gels stained with ethidium bromide. Photographs were taken under UV light, using the GelExpert software system (Nucleotech, USA). DNA sequencing and comparison with previously published sequences from the GenBank database confirmed the authenticity of PCR products.

5' Rapid amplification of cDNA ends (RACE procedure.—The 5' RACE kit (RACE) was used to synthesize first-strand cDNA species from total AsPC1 cell line RNA (2 µg) with specific MUC17 primer (RACE 171: GTGATAGC-CTCTGAACTGGCC; SEQ ID NO: 13). Terminal transferase was used to add a poly (dA) tail to the 3' end of the cDNA. RACE-PCR experiments were performed in 50 µl reaction volumes containing 5 µl of 10× buffer (100 mM Tris/HCl/15 mM MgCl$_2$/500 mM KCl, pH 8.3), 5 µl of 10 mM deoxynucleoside triphosphates, 5 µl of poly(dA)-tailed cDNA, 0.2 µM of each primers (MUC17 specific RACE 172: CATGGTGCTGGCAGGCATACT; SEQ ID NO: 14, and the oligo(dT)-anchor primer provide by the supplier), and 2 units of Taq DNA polymerase (Fermentase). The mixture was denatured at 94° C. for 2 min followed by 30 cycles at 94° C. for 30 s, 60° C. for 1 min and additionally 72° C. for 2 min. The elongation step was extended for an additional 15 min period. A 1 µl amplification product was further amplified by a second PCR reaction with a nested specific primer of MUC17 (RACE 173: GTAGGAGAT-GAACTTGCCTGA; SEQ ID NO: 15) and the PCR anchor primer (Provided by the supplier Roche). The thermal cycling protocol used was the same as for the primary RACE amplification step. PCR products were electrophoretically resolved on 1% agarose gels stained with ethidium bromide. Photographs were taken under UV light, using the GelExpert software system (Nucleotech, USA). Amplification products were excised and purified with QIAquick® Gel Extraction Kit (QIAgen), cloned into pCR2.1 vector (Invitrogen), and finally sequenced.

Expand long PCR—To identify potential MUC17 splice variants in the 3'-extremity, an RT-PCR strategy was performed, using the Expand™ Long PCR System (ROCHE) with sense primer CTGTGCCAAGAACCACAACAT; SEQ ID NO: 16 and antisense primer CTCCTCACTCCCA-GACTTCTC; SEQ ID NO: 17. Expand long PCR experiments were performed in 50 µl reaction volumes containing 5 µl of AsPC1 cDNA, 5 µl of 10× buffer 3, 2.5 µl of 40 mM deoxynucleoside triphosphates, 0.2 µM of each primer, 0.75 mM MgCl$_2$, and 2.5 units of polymerase mixture (ROCHE). The mixture was denatured at 94° C. for 2 min followed by 30 cycles at 94° C. for 30 s, 60° C. for 1 min and additionally 68° C. for 4 min with elongation time for the last 20 cycles extended 40 s for each cycle. The elongation step was extended for an additional 30 min period. Amplification products were directly cloned into pCR2.1 vector (Invitrogen) and positive clones were further processed for sequencing.

Transcription and translation assay in vitro—An amplification product generated using forward primer GCCAGCTCCTCTGGGGTGAC; SEQ ID NO: 18 and reverse primer RACE 171 (described previously) was subcloned in pCR2.1 under the control to the T7 promoter. The cDNA, coding for a peptide with a predicted size of 36 kDa, comprises the putative Kozak sequence followed by an ATG as well as the 25-residue N-terminal signal sequence. Transcription and translation experiments were performed with the TnT® Quick Coupled Transcription/Translation System (Promega) in accordance with the manufacturer's instructions. The amino acid mixture lacking methionine, supplemented with [$^{35}$S] methionine, was used. Translation products were analyzed by SDS/PAGE.

Figure 5:
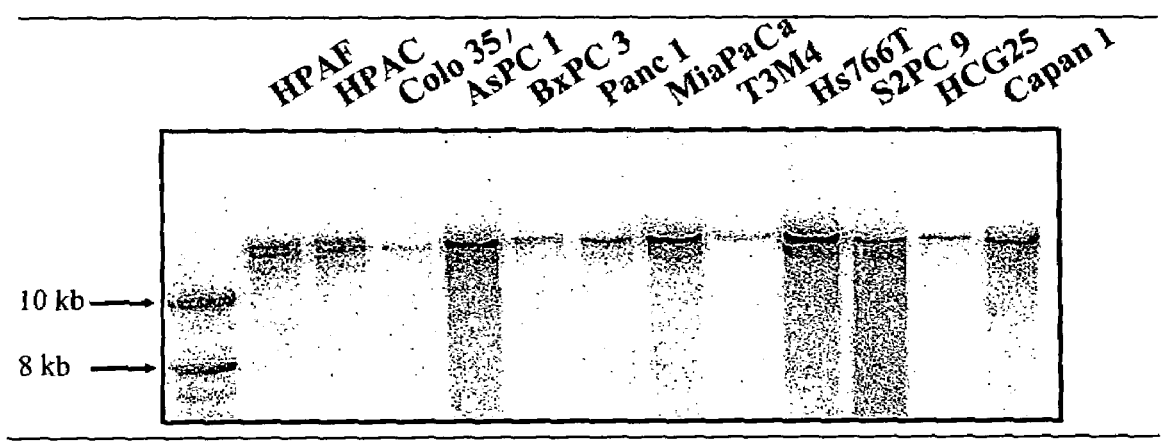
FIG. 5 is a Southern Blot of genomic DNA from various pancreatic tumor cell lines. After digestion with EcoRI and Pst I, the DNA was fractionated on an 0.8% agarose gel. The blot was probed with a $^{32}$P-labeled tandem repeat sequence of MUC 17.

Southern blot analysis—Genomic DNA from the human pancreatic tumor cell lines such as Pancl, CD18/HPAF, BxPC3, AsPC1, Capan1, and SW1990 were digested with EcoRI and HindIII restriction endonucleases. Digested products were resolved by electrophoresis in 0.8% agarose gels and transferred to nylon membranes. The blot was hybridized with MUC17 tandem repeat probe. See FIG. 5. The probe was prepared by PCR amplification using MUC17 TR forward primer: GATATGAGCACACCTCTGACC; (SEQ ID NO: 19) and MUC17 TR reverse primer: ATGTTGTG-GTTCTTGGCACAG; (SEQ ID NO: 20). A 3-kb amplification product was obtained, subcloned in pCR2.1, and sequences. The corresponding insert was radio labeled using the Random Primers DNA Labeling System (Invitrogen) and [$^{32}$p]dCTP (ICN).

RESULTS

Pancreatic Expression Pattern of the Membrane-Bound Mucins in Inflammatory and Tumoral Physiologic Conditions Dysregulation of mucins is a frequent occurrence in malignancies of epithelial origin. MUC4 (12;16) has previously been identified as a specific marker for pancreatic cancer and has been proposed as a target for the development of cancer therapy as well as early diagnosis. However, 25% of pancreatic adenocarcinoma tumors studied were negative for MUC4 expression and thus other markers are required to accurately diagnose this type of cancer. To improve the sensitivity of detection and develop an early diagnostic able to screen a wide range of patients, a multimarker screening method has been developed.

The expression of MUC1, MUC3, MUC4, MUC12, MUC13, MUC16, and MUC17 was studied in a panel of 2 normal pancreas samples, 8 pancreatitis samples, and 16 pancreatic adenocarcinoma samples. As shown in FIG. 1 and FIG. 2, results from RT-PCR analysis revealed an alteration in the expression pattern of the membrane-bound mucins, as tissue progressed from normal to malignant. Indeed, only MUC1 and MUC13 were detected in normal pancreas. Their level of expression was low, at the limit of detection for MUC13. Seven out of 8 pancreatitis specimens expressed MUC1 and MUC13 at a higher level than that observed in the normal pancreas. In addition to MUC1 and MUC13, MUC16 was also detected in 7 out 8 of the pancreatitis tissues. The tissue sample negative for MUC16 expression was also negative for MUC1 and MUC13. As expected, relatively high levels of MUC1 and MUC4 transcripts were detected in 100% and 93%, respectively, of the pancreatic adenocarcinoma specimens tested (FIG. 2). Fifteen out of the 16 samples examined were positive for MUC4 expression, although 3 were at the limit of detection. Surprisingly, MUC13 was detected in only 56% of the tumors tested with a level of expression in the positive samples comparable to that observed in the pancreatitis samples. MUC16, which was slightly expressed in pancreatitis, presented a very high level of expression in 95% of the tumor samples examined. Regarding the mucins clustered on chromosome 7q22, MUC3, MUC12, and MUC17 were expressed at 6%, 75%, and 87%, respectively, in the tumor samples. These results indicate that in addition to MUC4, MUC12 and MUC17 up-regulation is associated with the occurrence of pancreatic cancer.

Figure 3:
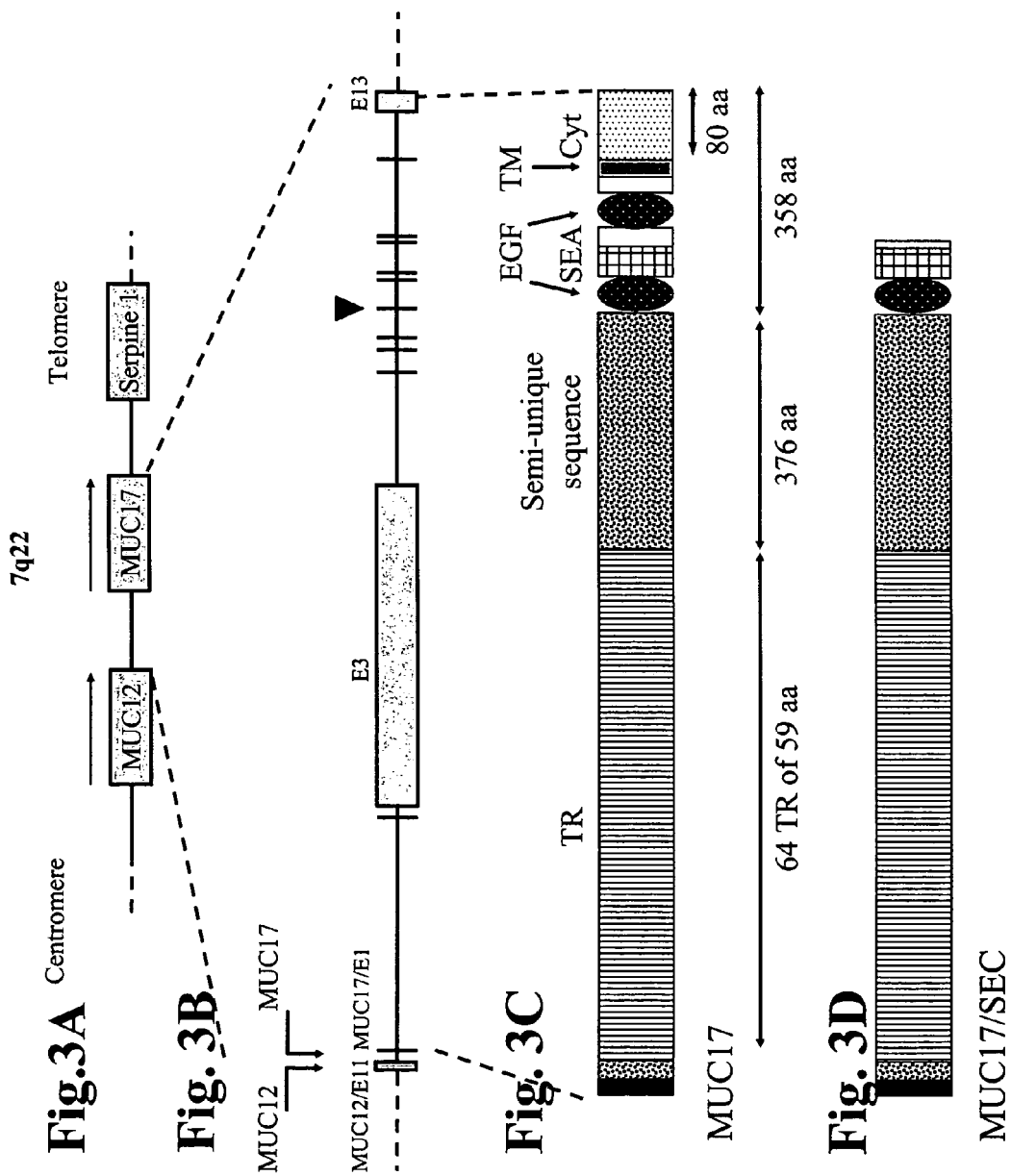
FIGS. 3A–3D are schematic drawings of the structure of the MUC17 gene and the protein encoded thereby. A) MUC17 is clustered with MUC3 and MUC12 on chromosome 7 in the region q22. MUC17 is oriented centromere to telomere between MUC12 and Serpine 1. B) MUC17 encompasses 13 exons and overlaps 39 kb of genomic DNA. Its first exon is located at 1146 bp from the last exon of MUC12. The black triangle indicates a position in exon 7 where alternative splicing occurs. C) MUC17 RNA is 14221 bp long and codes for a membrane-bound mucin. Its central domain is composed of 64 repeating motifs of 59 amino acid residues rich in serine, threonine, and proline. A 25 amino acid signal peptide is found at the N-terminus. D) An alternative splice event, which excludes exon 7, gives rise to the secreted form of MUC17, MUC17/SEC. MUC17/SEC lacks the unique sequence located upstream of the SEA module, as well as the second EGF-like domain, transmembrane sequence and the cytoplasmic tail. The last 21 residues are specific to MUC17/SEC.

Identification of the Full Length Sequence of MUC17 MUC17 was identified by computational analysis by Gum et al. (22) who employed a 59 amino acid residue peptide believed at that time to be part of MUC3. The authors were able to demonstrate that this sequence belonged to a new mucin called MUC17 and was clustered on chromosome 7q22 with MUC3 and MUC12. Using RT-PCR techniques, Gum et al cloned the carboxy-terminal sequence of MUC17. With this sequence (accession number AF430017), the human genome resources database from the National Center of Biotechnology information server and the human genome project (DOE Joint Genome Institute Human Genome Project) were screened to precisely localize the MUC17 coding sequence to chromosome 7 in the region q22.1, oriented from centromere to telomere, between the MUC12 gene and the serine proteinase inhibitor SERPINE1. To extend MUC17 sequence in the 5' end, the 177 bp motif of repetition that characterized the tandem repeat array of MUC17 was positioned in a way to extend the upstream sequence by walking on the chromosome. MUC17 allele in the data base (BAC RP11-395B7 with accession number AC105443) showed 64 repetitions of this motif of 177 bp. Up to 600 bp of degenerated repetitive sequence were located at the 5'-extremity of 177 bp array domain. Three antisense primers were chosen in this degenerate sequence and used to perform a 5'-RACE-PCR on the MUC17 highly expressing pancreatic adenocarcinoma cell line AsPC1. Several amplification products were detected with a size varying from 200 to 800 bp for the first PCR, and from 200 to 700 bp after nested PCR. Products from the nested PCR were cloned and the largest cDNA fragment of 653 bp was sequenced. Its 3'-end was overlapping the 5'-extremity of degenerated repetition located upstream of the 64 motif of 177 bp. Comparing the 5'-end of the RACE-PCR product with the sequence of the BAC RP11-395B7, two new exons were identified. The compiled nucleotide sequences of the RACE-PCR clone, with the 177 bp tandem repeat of the BAC RP11-395B7, and with the sequence identified and characterized by Gum et al (AF430017), allowed us to establish the complete sequence of MUC17 (FIG. 3).

Genomic DNA from pancreatic adenocarcinoma cell lines was digested with HindIII and EcoRI endonuclease enzymes. One HindIII site is located at 5434 bp upstream of the tandem repeat array and one EcoRI site is located at 1128 bp downstream from the repetitive sequence. Digestion using these two enzymes of the BAC RP11-395B7 predicted a fragment of 18.75 kb. Southern blot analysis demonstrated one unique band of 18 kb for all the cell lines investigated with the exception of HPAF and HPAC lines where two close alleles were seen. See FIG. 5. Therefore, in contrast to other mucin genes, MUC17 did not exhibit very high degree of variable number of tandem repeat polymorphisms (VNTR).

MUC17 mRNA is 14221 bp long and overlaps a 39000 bp DNA fragment between MUC12 and SERPINE1 on chromosome 7 in the region q22 (FIG. 3A). MUC17 encompass 13 exons ranging in size from 61 bp to 12185 bp (Table I) whereas intron size ranged from 121 to 10902 bp (FIG. 3B).

All the 5' donor and 3' acceptor sites were consistent with the consensus gt-ag motifs described for splice sites in Eukaryote genes. The largest exon, E3, is at a central position and is composed of 64 repetitions of a motif of 177 bp, encoding the main O-glycosylated domain of MUC17 which is a hallmark of mucin family members. The N-terminal domain of MUC17 is encoded by 2 exons, the first one, E1, located at 1146 bp from the 3'-extremity of MUC12 last exon. The position of MUC17 first exon was checked by PCR amplification on AsPC1 genomic DNA using a forward primer located in MUC12 last exon and a reverse primer located in MUC17 first exon. The expected amplification product was detected (data not shown). El contains the 5'-UTR as well as the sequence coding for MUC17 signal peptide. A methionine residue at position 54 is contained within the context for initiation of translation, AGAGCTCCGATG, as described by Kozak (30). The Kyte-Doolittle (31) hydropathy plot of the N-terminal extremity of MUC17 show that the initial 25 residues encoded by exon 1 are very hydrophobic. Additionally, the SignalP V1.1 software from the Center for Biological Sequence Analysis predicted the presence of a signal peptide within these 25 amino acid residues with a cleavage site located between position 25 and 26 (AAA-EQ). A schematic representation of MUC17 deduced amino acid sequence is shown in FIG. 3C.

TABLE I

Characteristics of the exon-intron junctions of the MUC17 gene
Capital letters indicate exons and small letters indicate introns.
Positions are defined according to the sequence of MUC17 (XXXXX)

| Protein domain | Exon N° | Size (bp) | 5'-Splice donor | Intron Name | Position | Size (bp) |
|---|---|---|---|---|---|---|
| 5'-UTR, leader sequence | 1 | 136 | A C A A G gt g a g t g a c c | 1 | 136–137 | 10902 |
| amino terminal | 2 | 101 | G G A C A G gt a a g g c a a c | 2 | 237–238 | 379 |
| central | 3 | 12185 | C A A C A T gt a a g t g a t t | 3 | 12456–12457 | 4163 |
| EGF1 | 4 | 132 | A C A T A G gt g a g t g c a a | 4 | 12587–12588 | 729 |
| EGF1, SEA | 5 | 129 | G A A C A G gt a a g t c t g g | 5 | 12715–12716 | 351 |
| SEA | 6 | 61 | G C T A C G gt a a g t g t c t | 5' | 12775–12776 | 1101 |
| SEA | 7 | 153 | G C T C A G gt g a a c t c t g | 6 | 12927–12928 | 977 |
| SEA, EGF2 | 8 | 70 | C T G A A G gt a g g t g a t a | 7 | 12996–12997 | 121 |
| EGF2 | 9 | 160 | G T G C C T gt g a g t g c t c | 8 | 13156–13157 | 1023 |
| transmembrane sequence | 10 | 163 | G A A A C G gt g a g c g a g c | 9 | 13318–13319 | 191 |
| cytoplasmic tail | 11 | 99 | G C C A A G gt a t t g g c c t | 10 | 13416–13417 | 2757 |
| cytoplasmic tail | 12 | 77 | A C A A A G gt a a g a a g g g | 11 | 13492–13493 | 1730 |
| cytoplasmic tail, 3'-UTR | 13 | 755 | | | | |

| Protein domain | Class | 3'-Splice acceptor |
|---|---|---|
| 5'-UTR, leader sequence | 3 | t c t c t t t c ag A C C T C A |
| amino terminal | 2 | t c t t a a a c ag G T T C T G |
| central | 2 | t t c c a c a g ag G C T T T G |
| EGF1 | 2 | c c c g c c t c ag G G C C A C |
| EGF1, SEA | 1 | t g c c t t t c ag A T G A A T |
| SEA | 3 | c c c t c t t c ag T C T T G G |
| SEA | 2 | t c t t t c a c ag A C A T G A |
| SEA, EGF2 | 2 | c c c c c a c c ag A G G A C T |
| EGF2 | 3 | c c c a t c t c ag C T G C G T |
| transmembrane sequence | 3 | c c a t c a c t ag G C A A A A |

TABLE I-continued

Characteristics of the exon-intron junctions of the MUC17 gene
Capital letters indicate exons and small letters indicate introns.
Positions are defined according to the sequence of MUC17 (XXXXX)

| | | |
|---|---|---|
| cytoplasmic tail | 2 | c c t c c a c a a g A T G A T G |
| cytoplasmic tail | 1 | c t c t t t t c a g A T C C G A |
| cytoplasmic tail, 3'-UTR | | |

Figure 4:
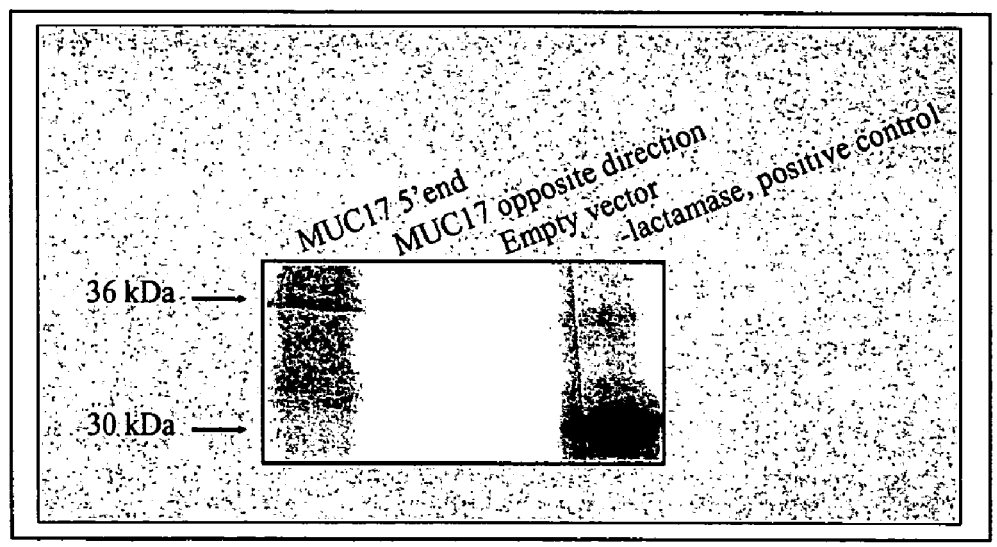
FIG. 4 is a gel showing the results of in vitro transcription and translation of the MUC17 complete coding region (SEQ ID NO: 3).

The region upstream of the tandem repeat of MUC17 was amplified by PCR on AsPC1 cDNA and subcloned into the PCR2.1 vector (Invitrogen). The positive clones were screen by sequencing and one clone comprising the MUC17 ATG directly downstream the T7 promoter of the PCR2.2 vector was used to perform in vitro transcription and translation using the TnT® Quick Coupled Transcription/translation System (Promega). As negative control, empty vector as well as a vector containing the coding sequence of MUC17 in an antisense orientation was used. FIG. 4 provides the results of these experiments. As expected, a 36 kDa protein was detected using the vector encoding the full length coding sequence for MUC17. No proteins were detected in the negative control samples. As positive control, the β galactosidase gene was used (provide by the supplier Promega). The expected 30 kDa protein is shown on the gel (FIG. 4). Therefore, the ATG located downstream the kozak sequence can initiate translation.

The presence of an alternative splice site in the 3'-extremity of MUC17 was investigated by RT-PCR. For this purpose, a forward primer was chosen in exon 3 (tandem repeat domain) and a reverse primer chosen in the 3'-UTR as described above in materials and methods. Using these primers, an expand long RT-PCR was carried out on AsPC1 cDNA, and the amplification product cloned and screened. Two distinct fragments were identified and fully sequenced. One of the fragments was 100% identical with the previous identified sequence of MUC17 (accession number AF430017). The second fragment revealed the presence of an alternative splice site that resulted in the deletion of exon 7. This alternative splicing event generated a frameshift with a stop codon positioned 66 nucleotides after the intron/exon junction. The resulting protein encoded a secreted form of MUC17, wherein the second EGF domain of the transmembrane domain and cytoplasmic tail were deleted. The last 21 amino acid residue of secreted MUC17 (MUC17SEC) was unique to this spliced form.

Pancreatic adenocarcinoma is the fifth leading cause of cancer in the United States, and the 5-year survival for the patients with this malignancy is less than 5%. Overall, 28,900 people in this country die each year from pancreatic cancer. Its incidence has tripled over the last 40 years. The present invention provides compositions and methods to facilitate detection and diagnosis of this deadly cancer.

REFERENCES

1. Landis, S. H., Murray, T., Bolden, S., and Wingo, P. A. (1999) *CA Cancer J Clin* 49, 8–31, 1
2. Parker, S. L., Tong, T., Bolden, S., and Wingo, P. A. (1997) *CA Cancer J Clin* 47, 5–27
3. Yeo, C. J., Cameron, J. L., Sohn, T. A., Coleman, J., Sauter, P. K., Hruban, R. H., Pitt, H. A., and Lillemoe, K. D. (1999) *Ann.Surg.* 229, 613–622
4. Yeo, C. J., Abrams, R. A., Grochow, L. B., Sohn, T. A., Ord, S. E., Hruban, R. H., Zahurak, M. L., Dooley, W. C., Coleman, J., Sauter, P. K., Pitt, H. A., Lillemoe, K. D., and Cameron, J. L. (1997) *Ann.Surg.* 225, 621–633
5. Rhodes, J. M. (1999) *Ann.Oncol.* 10, 118–121
6. Sell, S. (1990) *Hum.Pathol* 21, 1003–1019
7. Ho, J. J., Norton, K., Chung, Y. S., and Kim, Y. S. (1993) *Oncol Res* 5, 347–356
8. Ho, J. J. and Kim, Y. S. (1994) *Pancreas* 9, 674–691
9. Khorrami, A. M., Choudhury, A., Andrianifahanana, M., Varshney, G. C., Bhattacharyya, S. N., Hollingsworth, M. A., Kaufman, B., and Batra, S. K. (2002) *J Biochem (Tokyo)* 131, 21–29
10. Yin, B. W., Dnistrian, A., and Lloyd, K. O. (2002) *Int.J Cancer* 98, 737–740
11. Yin, B. W. and Lloyd, K. O. (2001) *J Biol.Chem.* % 20;276, 27371–27375
12. Andrianifahanana, M., Moniaux, N., Schmied, B. M., Ringel, J., Friess, H., Hollingsworth, M. A., Buchler, M. W., Aubert, J. P., and Batra, S. K. (2001) *Clin Cancer Res* 7, 4033–4040
13. Balague, C., Gambus, G., Carrato, C., Porchet, N., Aubert, J. P., Kim, Y. S., and Real, F. X. (1994) *Gastroenterology* 106, 1054–1061
14. Choudhury, A., Moniaux, N., Winpenny, J. P., Hollingsworth, M. A., Aubert, J. P., and Batra, S. K. (2000) *J Biochem (Tokyo)* 128, 233–243
15. Hollingsworth, M. A., Strawhecker, J. M., Caffrey, T. C., and Mack, D. R. (1994) *Int J Cancer* 57, 198–203
16. Swart, M. J., Batra, S. K., Varshney, G. C., Hollingsworth, M. A., Yeo, C. J., Cameron, J. L., Willentz, R. E., Hruban, R. H., and Argani, P. (2002) *Am J Clin Pathol* 117, 791–796
17. Jepson, S., Komatsu, M., Haq, B., Arango, M. E., Huang, D., Carraway, C. A., and Carraway, K. L. (2002) *Oncogene* 21, 7524–7532
18. Moniaux, N., Escande, F., Porchet, N., Aubert, J. P., and Batra, S. K. (2001) *Front Biosci.* 6, D1192–D1206
19. Yin, B. W. and Lloyd, K. O. (2001) *J Biol.Chem.* 276, 27371–27375
20. O'Brien, T. J., Beard, J. B., Underwood, L. J., Dennis, R. A., Santin, A. D., and York, L. (2001) *Tumour.Biol.* 22, 348–366
21. Chen, Y., Zhao, Y. H., Kalaslavadi, T. B., Hamati, E., Nehrke, K., Le, A. D., Ann, D. K., and Wu, R. (2003) *Am J Respir.Cell Mol.Biol.*,
22. Gum, J. R., Jr., Crawley, S. C., Hicks, J. W., Szymkowski, D. E., and Kim, Y. S. (2002) *Biochem Biophys.Res Commun.* 291, 466–475
23. Baruch, A., Hartmann, M., Yoeli, M., Adereth, Y., Greenstein, S., Stadler, Y., Skornik, Y., Zaretsky, J., Smorodinsky, N. I., Keydar, I., and Wreschner, D. H. (1999) *Cancer Res* 59, 1552–1561

24. Choudhury, A., Moniaux, N., Ringel, J., King, J., Moore, E., Aubert, J. P., and, and Batra, S. K. (2001) *Teratogenesis,Carcinogenesis, and Mutagenesis* 21, 83–96
25. Crawley, S. C., Gum, J. R. J., Hicks, J. W., Pratt, W. S., Aubert, J. P., Swallow, D. M., and Kim, Y. S. (1999) *Biochem Biophys Res Commun* 263, 728–736
26. Moniaux, N., Escande, F., Batra, S. K., Porchet, N., Laine, A., and Aubert, J. P. (2000) *Eur J Biochem* 267, 4536–4544
27. Obermair, A., Schmid, B. C., Stimpfl, M., Fasching, B., Preyer, O., Leodolter, S., Crandon, A. J., and Zeillinger, R. (2001) *Gynecol.Oncol.* 83, 343–347
28. Chirgwin, J. M., Przybyla, A. E., MacDonald, R. J., and Rutter, W. J. (1979) *Biochemistry* 18, 5294–5299
29. Choudhury, A., Singh, R. K., Moniaux, N., El-Metwally, T. H., Aubert, J. P., and Batra, S. K. (2000) *J Biol Chem* 275, 33929–33936
30. Kozak, M. (1987) *Nucleic Acids Res* 15, 8125–8148
31. Kyte, J. and Doolittle, R. F. (1982) *J Mol.Biol.* 157, 105–132
32. Inglis, S. K., Corboz, M. R., Taylor, A. E., and Ballard, S. T. (1997) *Am J Physiol* 272, L372–L377
33. Inglis, S. K., Corboz, M. R., and Ballard, S. T. (1998) *Am J Physiol* 274, L762–L766
34. Boat, T. F. and Cheng, P. W. (1989) *Acta Paediatr Scand Suppl* 363, 25–29
35. Moniaux, N., Nollet, S., Porchet, N., Degand, P., Laine, A., and Aubert, J. P. (1999) *Biochem J* 338, 325–333
36. Buisine, M. P., Devisme, L., Savidge, T. C., Gespach, C., Gosselin, B., Porchet, N., and Aubert, J. P. (1998) *Gut* 43, 519–524
37. Buisine, M. P., Devisme, L., Copin, M. C., Durand-Reville, M., Gosselin, B., Aubert, J. P., and Porchet, N. (1999) *Am J Respir Cell Mol Biol* 20, 209–218
38. Reid, C. J., Gould, S., and Harris, A. (1997) *Am J Respir Cell Mol Biol* 17, 592–598
39. Buisine, M. P., Desreumaux, P., Leteurtre, E., Copin, M. C., Colombel, J. F., Porchet, N., and Aubert, J. P. (2001) *Gut* 49, 544–551
40. Weiss, A. A., Babyatsky, M. W., Ogata, S., Chen, A., and Itzkowitz, S. H. (1996) *J Histochem.Cytochem.* 44, 1161–1166
41. Taylor-Papadimitriou, J., Burchell, J. M., Plunkett, T., Graham, R., Correa, I., Miles, D., and Smith, M. (2002) *J Mammary.Gland.Biol.Neoplasia.* 7, 209–221
42. Van, S., I, Pigny, P., Perrais, M., Porchet, N., and Aubert, J. P. (2001) *Front Biosci.* 6:D1216–34., D1216–D1234
43. Copin, M. C., Buisine, M. P., Devisme, L., Leroy, X., Escande, F., Gosselin, B., Aubert, J. P., and Porchet, N. (2001) *Front Biosci.* 6:D1264–75., D1264–D1275
44. Gendler, S. J. (2001) *J Mammary.Gland.Biol.Neoplasia.* 6, 339–353
45. Carraway, K. L., Price-Schiavi, S. A., Komatsu, M., Jepson, S., Perez, A., and Carraway, C. A. (2001) *J Mammary.Gland.Biol.Neoplasia.* 6, 323–337
46. Apostolopoulos, V., Pietersz, G. A., and McKenzie, I. F. (1999) *Curr.Opin.Mol.Ther.* 1, 98–103
47. Pecher, G., Haring, A., Kaiser, L., and Thiel, E. (2002) *Cancer Immunol.Immunother.* 51, 669–673
48. Mitchell, M. S. (2002) *Curr.Opin.Investig.Drugs* 3, 150–158
49. Kontani, K., Taguchi, O., Ozaki, Y., Hanaoka, J., Tezuka, N., Sawai, S., Inoue, S., Fujino, S., Maeda, T., Itoh, Y., Ogasawara, K., Sato, H., Ohkubo, I., and Kudo, T. (2002) *Cancer Gene Ther.* 9, 330–337
50. Heukamp, L. C., van Hall, T., Ossendorp, F., Burchell, J. M., Melief, C. J., Taylor-Papadimitriou, J., and Offringa, R. (2002) *J Immunother.* 25, 46–56
51. Koprowski, H., Steplewski, Z., Mitchell, K., Herlyn, M., Herlyn, D., and Fuhrer, P. (1979) *Somatic.Cell Genet.* 5, 957–971
52. Magnani, J. L., Nilsson, B., Brockhaus, M., Zopf, D., Steplewski, Z., Koprowski, H., and Ginsburg, V. (1982) *J Biol.Chem.* 257, 14365–14369
53. Balague, C., Audie, J. P., Porchet, N., and Real, F. X. (1995) *Gastroenterology* 109, 953–964
54. Gum, J. R., Jr., Hicks, J. W., Crawley, S. C., Dahl, C. M., Yang, S. C., Roberton, A. M., and Kim, Y. S. (2003) *J Biol. Chem.,*
55. Williams, S. J., McGuckin, M. A., Gotley, D. C., Eyre, H. J., Sutherland, G. R., and Antalis, T. M. (1999) *Cancer Res* 59, 4083–4089

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule comprising a nucleotide sequence encoding a mucin 17 (MUC17) polypeptide, wherein said MUC17 polypeptide has an amino acid sequence selected from the group consisting of SEQ ID NO: 3 and SEQ ID NO: 4.

2. The isolated nucleic acid molecule of claim 1, wherein said MUC17 polypeptide has the amino acid sequence of SEQ ID NO: 3.

3. The isolated nucleic acid molecule of claim 1, wherein said MUC17 polypeptide has the amino acid sequence of SEQ ID NO: 4.

4. The isolated nucleic acid molecule of claim 1, wherein said nucleotide sequence is SEQ ID NO: 1.

5. The isolated nucleic acid molecule of claim 1, wherein said nucleotide sequence is sequence of SEQ ID NO: 2.

6. The isolated nucleic acid of claim 1, which is DNA.

7. The isolated nucleic acid of claim 6, which is a cDNA encoding a MUC17 polypeptide.

8. The isolated nucleic acid of claim 6, which is a gene comprising introns and exons, said exons encoding said MUC17 polypeptide of SEQ ID NO: 3 or SEQ ID NO: 4, and said nucleic acid sequence having the intron exon junctions of Table I.

9. An isolated RNA molecule transcribed from the nucleic acid of claim 6.

10. An isolated plasmid comprising the nucleic acid molecule of claim 1.

11. An isolated vector comprising the nucleic acid molecule of claim 1.

12. An isolated retroviral vector comprising the nucleic acid molecule of claim 1.

13. An isolated host cell comprising the nucleic acid molecule of claim 1.

14. The isolated host cell of claim 13, wherein said host cell is selected from the group consisting of bacterial, fungal, mammalian, insect and plant cells.

15. The isolated host cell of claim 13, wherein said nucleic acid molecule is provided in a plasmid and is operably linked to mammalian regulatory elements in reverse, antisense orientation.

16. A method for diagnosing pancreatic cancer in a patient comprising:
   a) measuring the level of the nucleic acid molecule encoding MUC17 of claim 1 in a biological sample from said patient; and
   b) comparing said level of said MUC 17 nucleic acid molecule from said patient with that from a healthy subject, wherein an elevation of said level of said MUC17 nucleic acid molecule from said patient is indicative that said patient has pancreatic cancer.

17. The method of claim 16, wherein said MUC17 nucleic acid molecule is an mRNA which encodes a MUC17 protein having a sequence of SEQ ID NO: 3.

18. The method of claim 16, wherein said MUC17 nucleic acid molecule is an mRNA which encodes a MUC17 protein having a sequence of SEQ ID NO: 4.

19. The method of claim 16, further comprising:
   c) measuring expression levels MUC4 and/or MUC12 in said biological sample from said patient; and
   d) comparing said expression levels MUC4 and/or MUC12 from said patient with that from said healthy subject, wherein an elevation of said expression levels of MUC4 and/or MUC12 is indicative that said patient has pancreatic cancer.

20. A kit for diagnosing pancreatic cancer in a patient comprising:
   a) means for isolating RNAs from a biological sample;
   b) means for detecting and quantifying the nucleic acid molecule of claim 1, comprising at least one nucleic acid probe consisting of a sequence selected from the group consistina of SEQ ID NO: 13, SEQ ID NO: 14, and SEQ ID NO: 15; and optionally
   c) instructional material.

21. The kit of claim 20, wherein said nucleic acid probe further comprises a detectable label.

22. The kit of claim 20, wherein said mRNA encodes a MUC17 protein with a sequence of SEQ ID NO: 3.

23. The kit of claim 20, wherein said mRNA encodes a MUC17 protein with a sequence of SEQ ID NO: 4.

* * * * *

SEQUENCE LISTING

```
<160> NUMBER OF SEQ ID NOS: 45

<210> SEQ ID NO 1
<211> LENGTH: 14246
<212> TYPE: DNA
<213> ORGANISM: Homo Sapiens
<220> FEATURE:
<221> NAME/KEY: misc_feature
<222> LOCATION: (12860)...(12860)
<223> OTHER INFORMATION: y = t or c

<400> SEQUENCE: 1
tttcgccagc tcctctgggg gtgacaggca agtgagacgt gctcagagct ccgatgccaa      60
ggccagggac catggcgctg tgtctgctga ccttggtcct ctcgctcttg ccccacaag     120 ctgctgcaga acagggcctc agtgtgaaca gggctgtgtg ggatggagga gggtgcatct     180
```

```
cccaagggga cgtcttgaac cgtcagtgcc agcagctgtc tcagcacgtt aggacaggtt       240
ctgcgacaaa caccgccaca ggtacaacat ctacaaatgt cgtggagcca agaatgtatt       300
tgagttgcag caccaaccct gagatgacct cgattgagtc cagtgtgact tcagacactc       360
ctggtgtctc cagtaccagg atgacaccaa cagaatccag aacaacttca gaatctacca       420
gtgacagcac cacactttc cccagtccta ctgaagacac ttcatctcct acaactcctg        480
aaggcaccga cgtgcccatg tcaacaccaa gtgaagaaag catttcatca acaatggctt       540
ttgtcagcac tgcacctctt cccagttttg aggcctacac atctttaaca tataaggttg       600
atatgagcac acctctgacc acttctactc aggcaagttc atctcctact actcctgaaa       660
gcaccaccat acccaaatca actaacagtg aaggaagcac tccattaaca agtatgcctg       720
ccagcaccat gaaggtggcc agttcagagg ctatcaccct tttgacaact cctgttgaaa       780
tcagcacacc tgtgaccatt tctgctcaag ccagttcatc tcctacaact gctgaaggtc       840
ccagcctgtc aaactcagct cctagtggag gaagcactcc attaacaaga atgcctctca       900
gcgtgatgct ggtggtcagt tctgaggcta gcaccctttc aacaactcct gctgccacca       960
acattcctgt gatcacttct actgaagcca gttcatctcc tacaacggct gaaggcacca      1020
gcataccaac ctcaacttat actgaaggaa gcactccatt aacaagtacg cctgccagca      1080
ccatgccggt tgccacttct gaaatgagca cactttcaat aactcctgtt gacaccagca      1140
cacttgtgac cacttctact gaacccagtt cacttcctac aactgctgaa gctaccagca      1200
tgctaacctc aactcttagt gaaggaagca ctccattaac aaatatgcct gtcagcacca      1260
tattggtggc cagttctgag gctagcacca cttcaacaat tcctgttgac tccaaaactt      1320
ttgtgaccac tgctagtgaa gccagctcat ctcccacaac tgctgaagat accagcattg      1380
caacctcaac tcctagtgaa ggaagcactc cattaacaag tatgcctgtc agcaccactc      1440
cagtggccag ttctgaggct agcaaccttt caacaactcc tgttgactcc aaaactcagg      1500
tgaccacttc tactgaagcc agttcatctc ctccaactgc tgaagttaac agcatgccaa      1560
cctcaactcc tagtgaagga agcactccat taacaagtat gtctgtcagc accatgccgg      1620
tggccagttc tgaggctagc acccttcaa caactcctgt tgacaccagc acacctgtga       1680
ccacttctag tgaagccagt tcatcttcta caactcctga aggtaccagc ataccaacct      1740
caactcctag tgaaggaagc actccattaa caaacatgcc tgtcagcacc aggctggtgg      1800
tcagttctga ggctagcacc acttcaacaa ctcctgctga ctccaacact tttgtgacca      1860
cttctagtga agctagttca tcttctacaa ctgctgaagg taccagcatg ccaacctcaa      1920
cttacagtga agaggcact acaataacaa gtatgtctgt cagcaccaca ctggtggcca       1980
gttctgaggc tagcacccct tcaacaactc tgttgactc caacactcct gtgaccactt       2040
caactgaagc cacttcatct tctacaactg cggaaggtac cagcatgcca acctcaactt      2100
atactgaagg aagcactcca ttaacaagta tgcctgtcaa caccacactg gtggccagtt      2160
ctgaggctag cacccttca acaactcctg ttgacaccag cacacctgtg accacttcaa       2220
ctgaagccag ttcctctcct acaactgctg atggtgccag tatgccaacc tcaactccta      2280
gtgaaggaag cactccatta acaagtatgc ctgtcagcaa acgctgttg accagttctg       2340 aggctagcac ccttcaaca actcctcttg acacaagcac acatatcacc acttctactg       2400
aagccagttg ctctcctaca accactgaag gtaccagcat gccaatctca actcctagtg      2460
aaggaagtcc tttattaaca agtatacctg tcagcatcac accggtgacc agtcctgagg      2520
ctagcaccct ttcaacaact cctgttgact ccaacagtcc tgtgaccact tctactgaag      2580
```

-continued

```
tcagttcatc tcctacacct gctgaaggta ccagcatgcc aacctcaact tatagtgaag    2640
gaagaactcc tttaacaagt atgcctgtca gcaccacact ggtggccact tctgcaatca    2700 gcacccttc aacaactcct gttgacacca gcacacctgt gaccaattct actgaagccc    2760
gttcgtctcc tacaacttct gaaggtacca gcatgccaac ctcaactcct ggggaaggaa    2820
gcactccatt aacaagtatg cctgacagca ccacgccggt agtcagttct gaggctagaa    2880
cactttcagc aactcctgtt gacaccagca cctgtgac cacttctact gaagccactt    2940
catctcctac aactgctgaa ggtaccagca taccaacctc gactcctagt gaaggaacga    3000
ctccattaac aagcacacct gtcagccaca cgctggtggc caattctgag gctagcaccc    3060
tttcaacaac tcctgttgac tccaacactc ctttgaccac ttctactgaa gccagttcac    3120
ctcctcccac tgctgaaggt accagcatgc caacctcaac tcctagtgaa ggaagcactc    3180
cattaacacg tatgcctgtc agcaccacaa tggtggccag ttctgaaacg agcacacttt    3240
caacaactcc tgctgacacc agcacacctg tgaccactta ttctcaagcc agttcatctt    3300
ctacaactgc tgacggtacc agcatgccaa cctcaactta tagtgaagga agcactccac    3360
taacaagtgt gcctgtcagc accaggctgg tggtcagttc tgaggctagc acctttcca    3420 caactcctgt cgacaccagc atacctgtca ccacttctac tgaagccagt tcatctccta    3480
caactgctga aggtaccagc ataccaacct cacctcccag tgaaggaacc actccgttag    3540
caagtatgcc tgtcagcacc acgctggtgg tcagttctga ggctaacacc ctttcaacaa    3600
ctcctgtgga ctccaaaact caggtggcca cttctactga agccagttca cctcctccaa    3660
ctgctgaagt taccagcatg ccaacctcaa ctcctggaga agaagcact ccattaacaa    3720 gtatgcctgt cagacacacg ccagtggcca gttctgaggc tagcacctt tcaacatctc    3780 ccgttgacac cagcacacct gtgaccactt ctgctgaaac cagttcctct cctacaaccg    3840
ctgaaggtac cagcttgcca acctcaacta ctagtgaagg aagtactcta ttaacaagta    3900
tacctgtcag caccacgctg gtgaccagtc ctgaggctag caccttttta caaactcctg    3960
ttgacactaa aggtcctgtg gtcacttcta atgaagtcag ttcatctcct acacctgctg    4020
aaggtaccag catgccaacc tcaacttata gtgaaggaag aactccttta caagtatac    4080 ctgtcaacac cacactggtg gccagttctg caatcagcat cctttcaaca actcctgttg    4140
acaacagcac acctgtgacc acttctactg aagcctgttc atctcctaca acttctgaag    4200
gtaccagcat gccaaactca atcctagtg aaggaaccac tccgttaaca agtatacctg    4260
tcagcaccac gccggtagtc agttctgagg ctagcacct tcagcaact cctgttgaca    4320 ccagcacccc tgggaccact tctgctgaag ccacttcatc tcctacaact gctgaaggta    4380
tcagcatacc aacctcaact cctagtgaag gaaagactcc attaaaaagt atacctgtca    4440
gcaacacgcc ggtggccaat tctgaggcta gcacccttc aacaactcct gttgactcta    4500
acagtcctgt ggtcacttct acagcagtca gttcatctcc tacacctgct gaaggtacca    4560
gcatagcaat ctcaacgcct agtgaaggaa gcactgcatt aacaagtata cctgtcagca    4620
ccacaacagt ggccagttct gaaatcaaca gcctttcaac aactcctgct gtcaccagca    4680
cacctgtgac cacttattct caagccagtt catctcctac aactgctgac ggtaccagca    4740
tgcaaacctc aacttatagt gaaggaagca ctccactaac aagtttgcct gtcagcacca    4800
tgctggtggt cagttctgag gctaacaccc tttcaacaac ccctattgac tccaaaactc    4860
aggtgaccgc ttctactgaa gccagttcat ctacaaccg tgaaggtagc agcatgacaa    4920
```

```
tctcaactcc tagtgaagga agtcctctat taacaagtat acctgtcagc accacgccgg    4980
tggccagtcc tgaggctagc accctttcaa caactcctgt tgactccaac agtcctgtga    5040
tcacttctac tgaagtcagt tcatctccta cacctgctga aggtaccagc atgccaacct    5100
caacttatac tgaaggaaga actcctttaa caagtataac tgtcagaaca acaccggtgg    5160
ccagctctgc aatcagcacc ctttcaacaa ctcccgttga caacagcaca cctgtgacca    5220
cttctactga agcccgttca tctcctacaa cttctgaagg taccagcatg ccaaactcaa    5280
ctcctagtga aggaaccact ccattaacaa gtatacctgt cagcaccacg ccggtactca    5340
gttctgaggc tagcacccct tcagcaactc ctattgacac cagcacccct gtgaccactt    5400
ctactgaagc cacttcgtct cctacaactg ctgaaggtac cagcatacca acctcgactc    5460
ttagtgaagg aatgactcca ttaacaagca cacctgtcag ccacgcgtg gtggccaatt    5520
```

| | |
|---|---|
| acaccagcac acctgtcacc acttctactg aagccagttc atctcctaca actgctgaag | 7380 |
| gtaccagcat accaacctca cctcctagtg aaggaaccac tccgttagca agtatgcctg | 7440 |
| tcagcaccac gccggtggtc agttctgagg ctggcaccct ttccacaact cctgttgaca | 7500 |
| ccagcacacc tatgaccact tctactgaag ccagttcatc tcctacaact gctgaagata | 7560 |
| tcgtcgtgcc aatctcaact gctagtgaag gaagtactct attaacaagt atacctgtca | 7620 |
| gcaccacgcc agtggccagt cctgaggcta gcacccttc aacaactcct gttgactcca | 7680 |
| acagtcctgt ggtcacttct actgaaatca gttcatctgc tacatccgct gaaggtacca | 7740 |
| gcatgcctac ctcaacttat agtgaaggaa gcactccatt aagaagtatg cctgtcagca | 7800 |
| ccaagccgtt ggccagttct gaggctagca ctctttcaac aactcctgtt gacaccagca | 7860 |
| tacctgtcac cacttctact gaaccagtt catctcctac aactgcaaaa gataccagca | 7920 |
| tgccaatctc aactcctagt gaagtaagta cttcattaac aagtatactt gtcagcacca | 7980 |
| tgccagtggc cagttctgag gctagcaccc tttcaacaac tcctgttgac accaggacac | 8040 |
| ttgtgaccac ttccactgga accagttcat ctcctacaac tgctgaaggt agcagcatgc | 8100 |
| caacctcaac tcctggtgaa agaagcactc cattaacaaa tatacttgtc agcaccacgc | 8160 |
| tgttggccaa ttctgaggct agcaccctt caacaactcc tgttgacacc agcacacctg | 8220 |
| tcaccacttc tgctgaagcc agttcttctc ctacaactgc tgaaggtacc agcatgcgaa | 8280 |
| tctcaactcc tagtgatgga agtactccaa taacaagtat acttgtcagc ccctgccag | 8340 |
| tggccagttc tgaggctagc accgtttcaa caactgctgt tgacaccagc atacctgtca | 8400 |
| ccacttctac tgaagccagt tcctctccta caactgctga agttaccagc atgccaacct | 8460 |
| caactcctag tgaaacaagt actccattaa ctagtatgcc tgtcaccac acgccagtgg | 8520 |
| ccagttctga ggctggcacc ctttcaacaa ctcctgttga caccagcaca cctgtgacca | 8580 |
| cttctactaa agccagttca tctcctacaa ctgctgaagg tatcgtcgtg ccaatctcaa | 8640 |
| ctgctagtga aggaagtact ctattaacaa gtatacctgt cagcaccacg ccggtggcca | 8700 |
| gttctgaggc tagcacccett tcaacaactc ctgttgatac cagcatacct gtcaccactt | 8760 |
| ctactgaagg cagttcttct cctacaactg ctgaaggtac cagcatgcca atctcaactc | 8820 |
| ctagtgaagt aagtactcca ttaacaagta tacttgtcag caccgtgcca gtggccggtt | 8880 |
| ctgaggctag caccctttca acaactcctg ttgacaccag gacacctgtc accacttctg | 8940 |
| ctgaagctag ttcttctcct acaactgctg aaggtaccag catgccaatc tcaactcctg | 9000 |
| gcgaaagaag aactccatta acaagtatgt ctgtcagcac catgccggtg gccagttctg | 9060 |
| aggctagcac cctttcaaga actcctgctg acaccagcac acctgtgacc acttctactg | 9120 |
| aagccagttc ctctcctaca actgctgaag gtaccggcat accaatctca actcctagtg | 9180 |
| aaggaagtac tccattaaca agtatacctg tcagcaccac gccagtggcc attcctgagg | 9240 |
| ctagcacccct ttcaacaact cctgttgact ccaacagtcc tgtggtcact tctactgaag | 9300 |
| tcagttcatc tcctacacct gctgaaggta ccagcatgcc aatctcaact tatagtgaag | 9360 |
| gaagcactcc attaacaggt gtgcctgtca gcaccacacc ggtgaccagt tctgcaatca | 9420 |
| gcaccctttc aacaactcct gttgacacca gcacacctgt gaccacttct actgaagccc | 9480 |
| attcatctcc tacaacttct gaaggtacca gcatgccaac ctcaactcct agtgaaggaa | 9540 |
| gtactccatt aacatatatg cctgtcagca ccatgctggt agtcagttct gaggatagca | 9600 |
| ccctttcagc aactcctgtt gacaccagca cacctgtgac cacttctact gaagccactt | 9660 |

| | |
|---|---|
| catctacaac tgctgaaggt accagcattc caacctcaac tcctagtgaa ggaatgactc | 9720 |
| cattaactag tgtacctgtc agcaacacgc cggtggccag ttctgaggct agcatccttt | 9780 |
| caacaactcc tgttgactcc aacactcctt tgaccacttc tactgaagcc agttcatctc | 9840 |
| ctcccactgc tgaaggtacc agcatgccaa cctcaactcc tagtgaagga agcactccat | 9900 |
| taacaagtat gcctgtcagc accacaacgg tggccagttc tgaaacgagc cccttcaa | 9960 |
| caactcctgc tgacaccagc acctgtga ccacttattc tcaagccagt tcatctcctc | 10020 |
| caattgctga cggtactagc atgccaacct caacttatag tgaaggaagc actccactaa | 10080 |
| caaatatgtc tttcagcacc acgccagtgg tcagttctga ggctagcacc ctttccacaa | 10140 |
| ctcctgttga caccagcaca cctgtcacca cttctactga agccagttta tctcctacaa | 10200 |
| ctgctgaagg taccagcata ccaacctcaa gtcctagtga aggaaccact ccattagcaa | 10260 |
| gtatgcctgt cagcaccacg ccggtggtca gttctgaggt taacacccctt tcaacaactc | 10320 |
| ctgtggactc caacactctg gtgaccactt ctactgaagc cagttcatct cctacaatcg | 10380 |
| ctgaaggtac cagcttgcca acctcaacta ctagtgaagg aagcactcca ttatcaatta | 10440 |
| tgcctctcag taccacgccg gtggccagtt ctgaggctag cacccttca acaactcctg | 10500 |
| ttgacaccag cacacctgtg accacttctt ctccaaccaa ttcatctcct acaactgctg | 10560 |
| aagttaccag catgccaaca tcaactgctg gtgaaggaag cactccatta acaaatatgc | 10620 |
| ctgtcagcac cacaccggtg gccagttctg aggctagcac ccttcaaca actcctgttg | 10680 |
| actccaaaac ttttgttacc agttctagtc aagccagttc atctccagca actcttcagg | 10740 |
| tcaccactat gcgtatgtct actccaagtg aaggaagctc ttcattaaca actatgctcc | 10800 |
| tcagcagcac atatgtgacc agttctgagg ctagcacacc ttccactcct tctgttgaca | 10860 |
| gaagcacacc tgtgaccact tctactcaga gcaattctac tcctacacct cctgaagtta | 10920 |
| tcaccctgcc aatgtcaact cctagtgaag taagcactcc attaaccatt atgcctgtca | 10980 |
| gcaccacatc ggtgaccatt tctgaggctg cacagcttca acacttcct gttgacacca | 11040 |
| gcacacctgt gatcacttct acccaagtca gttcatctcc tgtgactcct gaaggtacca | 11100 |
| ccatgccaat ctggacgcct agtgaaggaa gcactccatt aacaactatg cctgtcagca | 11160 |
| ccacacgtgt gaccagctct gagggtagca cccttcaac accttctgtt gtcaccagca | 11220 |
| cacctgtgac cacttctact gaagccattt catcttctgc aactcttgac agcaccacca | 11280 |
| tgtctgtgtc aatgcccatg gaaataagca cccttgggac cactattctt gtcagtacca | 11340 |
| cacctgttac gaggtttcct gagagtagca ccccttccat accatctgtt tacaccagca | 11400 |
| tgtctatgac cactgcctct gaaggcagtt catctcctac aactcttgaa ggcaccacca | 11460 |
| ccatgcctat gtcaactacg agtgaaagaa gcactttatt gacaactgtc ctcatcagcc | 11520 |
| ctatatctgt gatgagtcct tctgaggcca gcacactttc aacacctcct ggtgatacca | 11580 |
| gcacaccttt gctcacctct accaaagccg gttcattctc catacctgct gaagtcacta | 11640 |
| ccatacgtat ttcaattacc agtgaaagaa gcactccatt aacaactctc cttgtcagca | 11700 |
| ccacacttcc aactagcttt cctggggcca gcatagcttc gacacctcct cttgacacaa | 11760 |
| gcacaacttt tacccttcct actgacactg cctcaactcc cacaattcct gtagccacca | 11820 |
| ccatatctgt atcagtgatc acagaaggaa gcacacctgg gacaaccatt tttattccca | 11880 |
| gcactcctgt caccagttct actgctgatg tcttccctgc aacaactggt gctgtatcta | 11940 |
| cccctgtgat aacttccact gaactaaaca caccatcaac ctccagtagt agtaccacca | 12000 |
| catcttttc aactactaag gaatttacaa caccccgcaat gactactgca gctcccctca | 12060 |

```
catatgtgac catgtctact gcccccagca cacccagaac aaccagcaga ggctgcacta    12120
cttctgcatc aacgctttct gcaaccagta cacctcacac ctctacttct gtcaccaccc    12180
gtcctgtgac cccttcatca gaatccagca ggccgtcaac aattacttct cacaccatcc    12240
cacctacatt tcctcctgct cactccagta cacctccaac aacctctgcc tcctccacga    12300
ctgtgaaccc tgaggctgtc accaccatga ccaccaggac aaaacccagc acacggacca    12360
cttccttccc cacggtgacc accaccgctg tccccacgaa tactacaatt aagagcaacc    12420
ccacctcaac tcctactgtg ccaagaacca caacatgctt tggagatggg tgccagaata    12480
cggcctctcg ctgcaagaat ggaggcacct gggatgggct caagtgccag tgtcccaacc    12540
tctattatgg ggagttgtgt gaggaggtgg tcagcagcat tgacataggg ccaccggaga    12600
ctatctctgc ccaaatggaa ctgactgtga cagtgaccag tgtgaagttc accgaagagc    12660
taaaaaacca ctcttcccag gaattccagg agttcaaaca gacattcacg aacagatga    12720
atattgtgta ttccgggatc cctgagtatg tcggggtgaa catcacaaag ctacgtcttg    12780
gcagtgtggt ggtggagcat gacgtcctcc taagaaccaa gtacacacca gaatacaaga    12840
cagtattgga caatgccacy gaagtagtga agagaaaat cacaaaagtg accacacagc    12900
aaataatgat taatgatatt tgctcagaca tgatgtgttt caacaccact ggcacccaag    12960
tgcaaaacat tacggtgacc cagtacgacc ctgaagagga ctgccggaag atggccaagg    13020
aatatggaga ctacttcgta gtggagtacc gggaccagaa gccatactgc atcagcccct    13080
gtgagcctgg cttcagtgtc tccaagaact gtaacctcgg caagtgccag atgtctctaa    13140
gtggacctca gtgcctctgc gtgaccacgg aaactcactg gtacagtggg gagacctgta    13200
accagggcac ccagaagagt ctggtgtacg gcctcgtggg ggcaggggtc gtgctgatgc    13260
tgatcatcct ggtagctctc ctgatgctcg ttttccgctc caagagagag gtgaaacggc    13320
aaaagtacag attgtctcag ttatacaagt ggcaagaaga ggacagtgga ccagctcctg    13380
ggaccttcca aaacattggc tttgacatct gccaagatga tgattccatc cacctggagt    13440
ccatctatag taatttccag ccctccttga cacacataga ccctgaaaca aagatccgaa    13500
ttcagaggcc tcaggtaatg acgacatcat tttaaggcat ggagctgaga agtctgggag    13560
tgaggagatc ccagtccggc taagcttggt ggagcatttt cccattgaga gccttccatg    13620
ggaactcaat gttcccattg taagtacagg aaacaagccc cgtacttacc aaggagaaag    13680
aggagagaca gcagtgctgg gagattctca aatagaaacc cgtggacgct ccaatgggct    13740
tgtcatgata tcaggctagg cttttcctgct cattttcaa agacgctcca gatttgaggg    13800
tactctgact gtaacatcta tcaccccatt gatcgccagg attgatttgg ttgatctggc    13860
tgagcaggcg ggtgtccccg tcctccctca ctgccccata tgtgtccctc ctaaagctgc    13920
atgctcagtt gaagaggacg agaggacgac cttctctgat agaggaggac cacgcttcag    13980
tcaaaggcat acaagtatct atctggactt ccctgctggc acttccaaac aagctcagag    14040
atgttcctcc cctcatctgc ccgggttcag taccatggac agcgccctcg acccgctgtt    14100
tacaaccatg accccttgga cactggactg catgcacttt acatatcaca aaatgctctc    14160
ataagaatta ttgcatacca tcttcatgaa aaacacctgt attaaatat agggcattta    14220
ccttttggta aagaaaaaaa aaaaaa                                         14246

<210> SEQ ID NO 2
<211> LENGTH: 14094
<212> TYPE: DNA
```

<213> ORGANISM: Homo Sapiens

<400> SEQUENCE: 2

| | | | | | |
|---|---|---|---|---|---|
| tttcgccagc | tcctctgggg | gtgacaggca | agtgagacgt | gctcagagct | ccgatgccaa | 60 |
| ggccagggac | catggcgctg | tgtctgctga | ccttggtcct | ctcgctcttg | cccccacaag | 120 |
| ctgctgcaga | acagggcctc | agtgtgaaca | gggctgtgtg | ggatggagga | gggtgcatct | 180 |
| cccaagggga | cgtcttgaac | cgtcagtgcc | agcagctgtc | tcagcacgtt | aggacaggtt | 240 |
| ctgcgacaaa | caccgccaca | ggtacaacat | ctacaaatgt | cgtggagcca | agaatgtatt | 300 |
| tgagttgcag | caccaaccct | gagatgacct | cgattgagtc | cagtgtgact | tcagacactc | 360 |
| ctggtgtctc | cagtaccagg | atgacaccaa | cagaatccag | aacaacttca | gaatctacca | 420 |
| gtgacagcac | cacactttc | cccagtccta | ctgaagacac | ttcatctcct | acaactcctg | 480 |
| aaggcaccga | cgtgcccatg | tcaacaccaa | gtgaagaaag | catttcatca | acaatggctt | 540 |
| tgtcagcac | tgcacctctt | cccagttttg | aggcctacac | atctttaaca | tataaggttg | 600 |
| atatgagcac | acctctgacc | acttctactc | aggcaagttc | atctcctact | actcctgaaa | 660 |
| gcaccaccat | acccaaatca | actaacagtg | aaggaagcac | tccattaaca | agtatgcctg | 720 |
| ccagcaccat | gaaggtggcc | agttcagagg | ctatcaccct | tttgacaact | cctgttgaaa | 780 |
| tcagcacacc | tgtgaccatt | tctgctcaag | ccagttcatc | tcctacaact | gctgaaggtc | 840 |
| ccagcctgtc | aaactcagct | cctagtggag | aagcactcc | attaacaaga | atgcctctca | 900 |
| gcgtgatgct | ggtggtcagt | tctgaggcta | gcaccctttc | aacaactcct | gctgccacca | 960 |
| acattcctgt | gatcacttct | actgaagcca | gttcatctcc | tacaacggct | gaaggcacca | 1020 |
| gcataccaac | ctcaacttat | actgaaggaa | gcactccatt | aacaagtacg | cctgccagca | 1080 |
| ccatgccggt | tgccacttct | gaaatgagca | cactttcaat | aactcctgtt | gacaccagca | 1140 |
| cacttgtgac | cacttctact | gaacccagtt | cacttcctac | aactgctgaa | gctaccagca | 1200 |
| tgctaacctc | aactcttagt | gaaggaagca | ctccattaac | aaatatgcct | gtcagcacca | 1260 |
| tattggtggc | cagttctgag | gctagcacca | cttcaacaat | tcctgttgac | tccaaaactt | 1320 |
| ttgtgaccac | tgctagtgaa | gccagctcat | ctcccacaac | tgctgaagat | accagcattg | 1380 |
| caacctcaac | tcctagtgaa | ggaagcactc | cattaacaag | tatgcctgtc | agcaccactc | 1440 |
| cagtggccag | ttctgaggct | agcaacccttt | caacaactcc | tgttgactcc | aaaactcagg | 1500 |
| tgaccacttc | tactgaagcc | agttcatctc | ctccaactgc | tgaagttaac | agcatgccaa | 1560 |
| cctcaactcc | tagtgaagga | agcactccat | taacaagtat | gtcgtcagc | accatgccgg | 1620 |
| tggccagttc | tgaggctagc | acccttcaa | caactcctgt | tgacaccagc | acacctgtga | 1680 |
| ccacttctag | tgaagccagt | tcatcttcta | caactcctga | aggtaccagc | ataccaacct | 1740 |
| caactcctag | tgaaggaagc | actccattaa | caaacatgcc | tgtcagcacc | aggctggtgg | 1800 |
| tcagttctga | ggctagcacc | acttcaacaa | ctcctgctga | ctccaacact | tttgtgacca | 1860 |
| cttctagtga | agctagttca | tcttctacaa | ctgctgaagg | taccagcatg | ccaacctcaa | 1920 |
| cttacagtga | aagaggcact | acaataacaa | gtatgtctgt | cagcaccaca | ctggtggcca | 1980 |
| gttctgaggc | tagcaccctt | tcaacaactc | ctgttgactc | caacactcct | gtgaccactt | 2040 |
| caactgaagc | cacttcatct | tctacaactg | cggaaggtac | cagcatgcca | acctcaactt | 2100 |
| atactgaagg | aagcactcca | ttaacaagta | tgcctgtcaa | caccacactg | gtggccagtt | 2160 |
| ctgaggctag | cacccttca | acaactcctg | ttgacaccag | cacacctgtg | accacttcaa | 2220 |
| ctgaagccag | ttcctctcct | acaactgctg | atggtgccag | tatgccaacc | tcaactccta | 2280 |

```
gtgaaggaag cactccatta acaagtatgc ctgtcagcaa aacgctgttg accagttctg    2340
aggctagcac cctttcaaca actcctcttg acacaagcac acatatcacc acttctactg    2400
aagccagttg ctctcctaca accactgaag gtaccagcat gccaatctca actcctagtg    2460
aaggaagtcc tttattaaca agtatacctg tcagcatcac accggtgacc agtcctgagg    2520
ctagcaccct ttcaacaact cctgttgact ccaacagtcc tgtgaccact tctactgaag    2580
tcagttcatc tcctacacct gctgaaggta ccagcatgcc aacctcaact tatagtgaag    2640
gaagaactcc tttaacaagt atgcctgtca gcaccacact ggtggccact tctgcaatca    2700 gcacccttc aacaactcct gttgacacca gcacacctgt gaccaattct actgaagccc    2760
gttcgtctcc tacaacttct gaaggtacca gcatgccaac ctcaactcct ggggaaggaa    2820
gcactccatt aacaagtatg cctgacagca ccacgccggt agtcagttct gaggctagaa    2880
cactttcagc aactcctgtt gacaccagca cacctgtgac cacttctact gaagccactt    2940
catctcctac aactgctgaa ggtaccagca taccaacctc gactcctagt gaaggaacga    3000
ctccattaac aagcacacct gtcagccaca cgctggtggc caattctgag gctagcaccc    3060
tttcaacaac tcctgttgac tccaacactc ctttgaccac ttctactgaa gccagttcac    3120
ctcctcccac tgctgaaggt accagcatgc caacctcaac tcctagtgaa ggaagcactc    3180
cattaacacg tatgcctgtc agcaccacaa tggtggccag ttctgaaacg agcacacttt    3240
caacaactcc tgctgacacc agcacacctg tgaccactta ttctcaagcc agttcatctt    3300
ctacaactgc tgacggtacc agcatgccaa cctcaactta gtgaagga agcactccac    3360 taacaagtgt gcctgtcagc accaggctgg tggtcagttc tgaggctagc acccttttcca    3420 caactcctgt cgacaccagc atacctgtca ccacttctac tgaagccagt tcatctccta    3480
caactgctga aggtaccagc ataccaacct cacctcccag tgaaggaacc actccgttag    3540
caagtatgcc tgtcagcacc acgctggtgg tcagttctga ggctaacacc ctttcaacaa    3600
ctcctgtgga ctccaaaact caggtggcca cttctactga agccagttca cctcctccaa    3660
ctgctgaagt taccagcatg ccaacctcaa ctcctggaga agaagcact ccattaacaa    3720 gtatgcctgt cagacacacg ccagtggcca gttctgaggc tagcacccct tcaacatctc    3780
ccgttgacac cagcacacct gtgaccactt ctgctgaaac cagttcctct cctacaaccg    3840
ctgaaggtac cagcttgcca acctcaacta ctagtgaagg aagtactcta ttaacaagta    3900
tacctgtcag caccacgctg gtgaccagtc ctgaggctag caccctttta caactcctg    3960 ttgacactaa aggtcctgtg gtcacttcta atgaagtcag ttcatctcct acacctgctg    4020
aaggtaccag catgccaacc tcaacttata gtgaaggaag aactccttta acaagtatac    4080
ctgtcaacac cacactggtg gccagttctg caatcagcat cctttcaaca actcctgttg    4140
acaacagcac acctgtgacc acttctactg aagcctgttc atctcctaca acttctgaag    4200
gtaccagcat gccaaactca aatcctagtg aaggaaccac tccgttaaca agtatacctg    4260
tcagcaccac gccggtagtc agttctgagg ctagcaccct ttcagcaact cctgttgaca    4320
ccagcacccc tgggaccact tctgctgaag ccacttcatc tcctacaact gctgaaggta    4380
tcagcatacc aacctcaact cctagtgaag gaaagactcc attaaaaagt atacctgtca    4440
gcaacacgcc ggtggccaat tctgaggcta gcacccttc aacaactcct gttgactcta    4500
acagtcctgt ggtcacttct acagcagtca gttcatctcc tacacctgct gaaggtacca    4560
gcatagcaat ctcaacgcct agtgaaggaa gcactgcatt aacaagtata cctgtcagca    4620
```

-continued

```
ccacaacagt ggccagttct gaaatcaaca gcctttcaac aactcctgct gtcaccagca      4680
cacctgtgac cacttattct caagccagtt catctcctac aactgctgac ggtaccagca      4740
tgcaaacctc aacttatagt gaaggaagca ctccactaac aagtttgcct gtcagcacca      4800
tgctggtggt cagttctgag gctaacaccc tttcaacaac ccctattgac tccaaaactc      4860
aggtgaccgc ttctactgaa gccagttcat ctacaaccgc tgaaggtagc agcatgacaa      4920
tctcaactcc tagtgaagga agtcctctat taacaagtat acctgtcagc accacgccgg      4980
tggccagtcc tgaggctagc accctttcaa caactcctgt tgactccaac agtcctgtga      5040
tcacttctac tgaagtcagt tcatctccta cacctgctga aggtaccagc atgccaacct      5100
caacttatac tgaaggaaga actccttttaa caagtataac tgtcagaaca caccggtgg       5160 ccagctctgc aatcagcacc ctttcaacaa ctcccgttga acacagcaca cctgtgacca      5220
cttctactga agcccgttca tctcctacaa cttctgaagg taccagcatg ccaaactcaa      5280
ctcctagtga aggaaccact ccattaacaa gtatacctgt cagcaccacg ccggtactca      5340
gttctgaggc tagcacccct tcagcaactc ctattgacac cagcacccct gtgaccactt      5400
ctactgaagc cacttcgtct cctacaactg ctgaaggtac cagcatacca acctcgactc      5460
ttagtgaagg aatgactcca ttaacaagca cacctgtcag ccacacgctg gtggccaatt      5520
ctgaggctag caccctttca caactcctg ttgactctaa cagtcctgtg gtcacttcta      5580
cagcagtcag ttcatctcct acacctgctg aaggtaccag catagcaacc tcaacgccta      5640
gtgaaggaag cactgcatta acaagtatac ctgtcagcac cacaacagtg gccagttctg      5700
aaaccaacac ccttttcaaca actcccgctg tcaccagcac acctgtgacc acttatgctc      5760
aagtcagttc atctcctaca actgctgacg gtagcagcat gccaacctca actcctaggg      5820
aaggaaggcc tccattaaca agtatacctg tcagcaccac aacagtggcc agttctgaaa      5880
tcaacaccct ttcaacaact cttgctgaca ccaggacacc tgtgaccact tattctcaag      5940
ccagttcatc tcctacaact gctgatggta ccagcatgcc aaccccagct tatagtgaag      6000
gaagcactcc actaacaagt atgcctctca gcaccacgct ggtggtcagt tctgaggcta      6060
gcactctttc cacaactcct gttgacacca gcactcctgc caccacttct actgaaggca      6120
gttcatctcc tacaactgca ggaggtacca gcatacaaac ctcaactcct agtgaacgga      6180
ccactccatt agcaggtatg cctgtcagca ctacgcttgt ggtcagttct gagggtaaca      6240
ccctttcaac aactcctgtt gactccaaaa ctcaggtgac caattctact gaagccagtt      6300
catctgcaac cgctgaaggt agcagcatga caatctcagc tcctagtgaa ggaagtcctc      6360
tactaacaag tatacctctc agcaccacgc cggtggccag tcctgaggct agcaccccttt      6420 caacaactcc tgttgactcc aacagtcctg tgatcacttc tactgaagtc agttcatctc      6480
ctatacctac tgaaggtacc agcatgcaaa cctcaactta tagtgacaga gaactcctt      6540 taacaagtat gcctgtcagc accacagtgg tggccagttc tgcaatcagc acctttcaa      6600 caactcctgt tgacaccagc acctgtgacc aattctact gaagcccgt tcatctccta      6660 caacttctga aggtaccagc atgccaacct caactcctag tgaaggaagc actccattca      6720
caagtatgcc tgtcagcacc atgccggtag ttacttctga ggctagcacc ctttcagcaa      6780
ctcctgttga caccagcaca cctgtgacca cttctactga agcccacttca tctcctacaa      6840 ctgctgaagg taccagcata ccaacttcaa ctcttagtga aggaacgact ccattaacaa      6900
gtatacctgt cagccacacg ctggtggcca attctgaggt tagcacccctt tcaacaactc      6960 ctgttgactc caacactcct ttcactactt ctactgaagc cagttcacct cctcccactg      7020
```

```
ctgaaggtac cagcatgcca acctcaactt ctagtgaagg aaacactcca ttaacacgta  7080
tgcctgtcag caccacaatg gtggccagtt ttgaaacaag cacactttct acaactcctg  7140
ctgacaccag cacacctgtg actacttatt ctcaagccgg ttcatctcct acaactgctg  7200
acgatactag catgccaacc tcaacttata gtgaaggaag cactccacta caagtgtgc   7260
ctgtcagcac catgccggtg gtcagttctg aggctagcac ccattccaca actcctgttg  7320
acaccagcac acctgtcacc acttctactg aagccagttc atctcctaca actgctgaag  7380
gtaccagcat accaacctca cctcctagtg aaggaaccac tccgttagca agtatgcctg  7440
tcagcaccac gccggtggtc agttctgagg ctggcaccct ttccacaact cctgttgaca  7500
ccagcacacc tatgaccact tctactgaag ccagttcatc tcctacaact gctgaagata  7560
tcgtcgtgcc aatctcaact gctagtgaag gaagtactct attaacaagt atacctgtca  7620
gcaccacgcc agtggccagt cctgaggcta gcacccttc aacaactcct gttgactcca   7680
acagtcctgt ggtcacttct actgaaatca gttcatctgc tacatccgct gaaggtacca  7740
gcatgcctac ctcaacttat agtgaaggaa gcactccatt aagaagtatg cctgtcagca  7800
ccaagccgtt ggccagttct gaggctagca ctctttcaac aactcctgtt gacaccagca  7860
tacctgtcac cacttctact gaaccagttc atctcctaca actgcaaaa gataccagca   7920
tgccaatctc aactcctagt gaagtaagta cttcattaac aagtatactt gtcagcacca  7980
tgccagtggc cagttctgag gctagcaccc tttcaacaac tcctgttgac accaggacac  8040
ttgtgaccac ttccactgga accagttcat ctcctacaac tgctgaaggt agcagcatgc  8100
caacctcaac tcctggtgaa agaagcactc cattaacaaa tatacttgtc agcaccacgc  8160
tgttggccaa ttctgaggct agcacccttt caacaactcc tgttgacacc agcacacctg  8220
tcaccacttc tgctgaagcc agttcttctc ctacaactgc tgaaggtacc agcatgcgaa  8280
tctcaactcc tagtgatgga agtactccat taacaagtat acttgtcagc ccctgccag   8340
tggccagttc tgaggctagc accgtttcaa caactgctgt tgacaccagc atacctgtca  8400
ccacttctac tgaagccagt tcctctccta caactgctga agttaccagc atgccaacct  8460
caactcctag tgaaacaagt actccattaa ctagtatgcc tgtcaaccac acgccagtgg  8520
ccagttctga ggctggcacc ctttcaacaa ctcctgttga caccagcaca cctgtgacca  8580
cttctactaa agccagttca tctcctacaa ctgctgaagg tatcgtcgtg ccaatctcaa  8640
ctgctagtga aggaagtact ctattaacaa gtatacctgt cagcaccacg ccggtggcca  8700
gttctgaggc tagcacccct tcaacaactc ctgttgatac cagcatacct gtcaccactt  8760
ctactgaagg cagttcttct cctacaactg ctgaaggtac cagcatgcca atctcaactc  8820
ctagtgaagt aagtactcca ttaacaagta acttgtcag caccgtgcca gtggccggtt   8880
ctgaggctag cacccttca acaactcctg ttgacaccag acacctgtc accacttctg    8940
ctgaagctag ttcttctcct acaactgctg aaggtaccag catgccaatc tcaactcctg  9000
gcgaaagaag aactccatta acaagtatgt ctgtcagcac catgccggtg gccagttctg  9060
aggctagcac ccttcaaga actcctgctg acaccagcac acctgtgacc acttctactg    9120
aagccagttc ctctcctaca actgctgaag gtaccggcat accaatctca actcctagtg  9180
aaggaagtac tccattaaca agtatacctg tcagcaccac gccagtggcc attcctgagg  9240
ctagcaccct ttcaacaact cctgttgact ccaacagtcc tgtggtcact tctactgaag  9300
tcagttcatc tcctacacct gctgaaggta ccagcatgcc aatctcaact tatagtgaag  9360
```

-continued

```
gaagcactcc attaacaggt gtgcctgtca gcaccacacc ggtgaccagt tctgcaatca    9420
gcacccttc  aacaactcct gttgacacca gcacacctgt gaccacttct actgaagccc    9480
attcatctcc tacaacttct gaaggtacca gcatgccaac ctcaactcct agtgaaggaa    9540
gtactccatt aacatatatg cctgtcagca ccatgctggt agtcagttct gaggatagca    9600
cccttcagc  aactcctgtt gacaccagca cacctgtgac cacttctact gaagccactt    9660
catctacaac tgctgaaggt accagcattc aacctcaac  tcctagtgaa ggaatgactc    9720
cattaactag tgtacctgtc agcaacacgc cggtggccag ttctgaggct agcatccttt    9780
caacaactcc tgttgactcc aacactcctt gaccacttc  tactgaagcc agttcatctc    9840
ctcccactgc tgaaggtacc agcatgccaa cctcaactcc tagtgaagga agcactccat    9900
taacaagtat gcctgtcagc accacaacgg tggccagttc tgaaacgagc ccctttcaa    9960
caactcctgc tgacaccagc acacctgtga ccacttattc tcaagccagt tcatctcctc   10020
caattgctga cggtactagc atgccaacct caacttatag tgaaggaagc actccactaa   10080
caaatatgtc tttcagcacc acgccagtgg tcagttctga ggctagcacc ctttccacaa   10140
ctcctgttga caccagcaca cctgtcacca cttctactga agccagttta tctcctacaa   10200
ctgctgaagg taccagcata ccaacctcaa gtcctagtga aggaaccact ccattagcaa   10260
gtatgcctgt cagcaccacg ccggtggtca gttctgaggt taacacccct tcaacaactc   10320
ctgtggactc caacactctg gtgaccactt ctactgaagc cagttcatct cctacaatcg   10380
ctgaaggtac cagcttgcca acctcaacta ctagtgaagg aagcactcca ttatcaatta   10440
tgcctctcag taccacgccg gtggccagtt ctgaggctag cacccttca  acaactcctg   10500
ttgacaccag cacacctgtg accacttctt ctccaaccaa ttcatctcct acaactgctg   10560
aagttaccag catgccaaca tcaactgctg gtgaaggaag cactccatta acaaatatgc   10620
ctgtcagcac cacaccggtg gccagttctg aggctagcac cctttcaaca actcctgttg   10680
actccaacac ttttgttacc agttctagtc aagccagttc atctccagca actcttcagg   10740
tcaccactat gcgtatgtct actccaagtg aaggaagctc ttcattaaca actatgctcc   10800
tcagcagcac atatgtgacc agttctgagg ctagcacacc ttccactcct tctgttgaca   10860
gaagcacacc tgtgaccact tctactcaga gcaattctac tcctacacct cctgaagtta   10920
tcaccctgcc aatgtcaact cctagtgaag taagcactcc attaaccatt atgcctgtca   10980
gcaccacatc ggtgaccatt tctgaggctg gcacagcttc aacacttcct gttgacacca   11040
gcacacctgt gatcacttct acccaagtca gttcatctcc tgtgactcct gaaggtacca   11100
ccatgccaat ctggacgcct agtgaaggaa gcactccatt aacaactatg cctgtcagca   11160
ccacacgtgt gaccagctct gagggtagca cccttcaac  accttctgtt gtcaccagca   11220
cacctgtgac cacttctact gaagccattt catcttctgc aactcttgac agcaccacca   11280
tgtctgtgtc aatgcccatg gaaataagca ccctgggac  cactattctt gtcagtacca   11340
cacctgttac gaggtttcct gagagtagca ccccttccat accatctgtt tacaccagca   11400
tgtctatgac cactgcctct gaaggcagtt catctcctac aactcttgaa ggcaccacca   11460
ccatgcctat gtcaactacg agtgaaagaa gcacttatt  gacaactgtc ctcatcagcc   11520
ctatatctgt gatgagtcct tctgaggcca gcacactttc aacacctcct ggtgatacca   11580
gcacaccttt gctcacctct accaaagccg gttcattctc catacctgct gaagtcacta   11640
ccatacgtat ttcaattacc agtgaaagaa gcactccatt aacaactctc cttgtcagca   11700
ccacacttcc aactagcttt cctggggcca gcatagcttc gacacctcct cttgacacaa   11760
```

```
gcacaactttt taccccttct actgacactg cctcaactcc cacaattcct gtagccacca    11820
ccatatctgt atcagtgatc acagaaggaa gcacacctgg gacaaccatt tttattccca    11880
gcactcctgt caccagttct actgctgatg tctttcctgc aacaactggt gctgtatcta    11940
cccctgtgat aacttccact gaactaaaca caccatcaac ctccagtagt agtaccacca    12000 catcttttc aactactaag gaatttacaa cacccgcaat gactactgca gctccctca     12060 catatgtgac catgtctact gccccagca cacccagaac aaccagcaga ggctgcacta    12120
cttctgcatc aacgctttct gcaaccagta cacctcacac ctctacttct gtcaccaccc   12180
gtcctgtgac cccttcatca gaatccagca ggccgtcaac aattacttct cacaccatcc   12240
cacctacatt tcctcctgct cactccagta cacctccaac aacctctgcc tcctccacga   12300
ctgtgaaccc tgaggctgtc accaccatga ccaccaggac aaaacccagc acacggacca   12360
cttccttccc cacggtgacc accacgctg tccccacgaa tactacaatt aagagcaacc    12420
ccacctcaac tcctactgtg ccaagaacca acatgcttt ggagatgggg tgccagaata    12480
cggcctctcg ctgcaagaat ggaggcacct gggatgggct caagtgccag tgtcccaacc   12540
tctattatgg ggagttgtgt gaggaggtgg tcagcagcat tgacataggg ccaccggaga   12600
ctatctctgc ccaaatggaa ctgactgtga cagtgaccag tgtgaagttc accgaagagc   12660
taaaaaacca ctcttcccag gaattccagg agttcaaaca gacattcacg gaacagatga   12720
atattgtgta ttccgggatc cctgagtatg tcgggtgaa catcacaaag ctacgtcatg    12780
atgtgtttca acaccactgg cacccaagtg caaaacatta cggtgaccca gtacgaccct   12840
gaagaggact gccggaagat ggccaaggaa tatggagact acttcgtagt ggagtaccgg   12900
gaccagaagc catactgcat cagcccctgt gagcctggct tcagtgtctc caagaactgt   12960
aacctcggca gtgccagat gtctctaagt ggacctcagt gcctctgcgt gaccacggaa    13020
actcactggt acagtgggga gacctgtaac cagggcaccc agaagagtct ggtgtacggc   13080
ctcgtggggg caggggtcgt gctgatgctg atcatcctgg tagctctcct gatgctcgtt   13140
ttccgctcca agagagaggt gaaacggcaa aagtacagat tgtctcagtt atacaagtgg   13200
caagaagagg acagtggacc agctcctggg accttccaaa acattggctt tgacatctgc   13260
caagatgatg attccatcca cctggagtcc atctatagta atttccagcc ctccttgaga   13320
cacatagacc ctgaaacaaa gatccgaatt cagaggcctc aggtaatgac gacatcattt   13380
taaggcatgg agctgagaag tctgggagtg aggagatccc agtccggcta agcttggtgg   13440
agcattttcc cattgagagc cttccatggg aactcaatgt tcccattgta agtacaggaa   13500
acaagccccg tacttaccaa ggagaaagag gagagacagc agtgctggga gattctcaaa   13560
tagaaacccg tggacgctcc aatgggcttg tcatgatatc aggctaggct ttcctgctca   13620
tttttcaaag acgctccaga tttgagggta ctctgactgt aacatctatc accccattga   13680
tcgccaggat tgatttggtt gatctggctg agcaggcggg tgtccccgtc ctccctcact   13740
gccccatatg tgtccctcct aaagctgcat gctcagttga agaggacgag aggacgacct   13800
tctctgatag aggaggacca cgcttcagtc aaaggcatac aagtatctat ctggacttcc   13860
ctgctggcac ttccaaacaa gctcagagat gttcctcccc tcatctgccc gggttcagta   13920
ccatggacag cgccctcgac ccgctgttta caaccatgac cccttggaca ctggactgca   13980
tgcactttac atatcacaaa atgctctcat aagaattatt gcataccatc ttcatgaaaa   14040
acacctgtat ttaaatatag ggcatttacc ttttggtaaa gaaaaaaaaa aaaa           14094
```

-continued

```
<210> SEQ ID NO 3
<211> LENGTH: 4493
<212> TYPE: PRT
<213> ORGANISM: Homo Sapiens
<220> FEATURE:
<221> NAME/KEY: UNSURE
<222> LOCATION: (4269)...(4269)
<223> OTHER INFORMATION: Xaa = any amino acid

<400> SEQUENCE: 3
```

Met Pro Arg Pro Gly Thr Met Ala Leu Cys Leu Leu Thr Leu Val Leu
 1               5                  10                  15

Ser Leu Leu Pro Pro Gln Ala Ala Glu Gln Gly Leu Ser Val Asn
                20                  25                  30

Arg Ala Val Trp Asp Gly Gly Cys Ile Ser Gln Gly Asp Val Leu
            35                  40                  45

Asn Arg Gln Cys Gln Gln Leu Ser Gln His Val Arg Thr Gly Ser Ala
 50                  55                  60

Thr Asn Thr Ala Thr Gly Thr Thr Ser Thr Asn Val Val Glu Pro Arg
 65                  70                  75                  80

Met Tyr Leu Ser Cys Ser Thr Asn Pro Glu Met Thr Ser Ile Glu Ser
                85                  90                  95

Ser Val Thr Ser Asp Thr Pro Gly Val Ser Ser Thr Arg Met Thr Pro
            100                 105                 110

Thr Glu Ser Arg Thr Thr Ser Glu Ser Thr Ser Asp Ser Thr Thr Leu
        115                 120                 125

Phe Pro Ser Pro Thr Glu Asp Thr Ser Ser Pro Thr Thr Pro Glu Gly
130                 135                 140

Thr Asp Val Pro Met Ser Thr Pro Ser Glu Glu Ser Ile Ser Ser Thr
145                 150                 155                 160

Met Ala Phe Val Ser Thr Ala Pro Leu Pro Ser Phe Glu Ala Tyr Thr
                165                 170                 175

Ser Leu Thr Tyr Lys Val Asp Met Ser Thr Pro Leu Thr Thr Ser Thr
            180                 185                 190

Gln Ala Ser Ser Ser Pro Thr Thr Pro Glu Ser Thr Thr Ile Pro Lys
        195                 200                 205

Ser Thr Asn Ser Glu Gly Ser Thr Pro Leu Thr Ser Met Pro Ala Ser
210                 215                 220

Thr Met Lys Val Ala Ser Ser Glu Ala Ile Thr Leu Leu Thr Pro
225                 230                 235                 240

Val Glu Ile Ser Thr Pro Val Thr Ile Ser Ala Gln Ala Ser Ser Ser
                245                 250                 255

Pro Thr Thr Ala Glu Gly Pro Ser Leu Ser Asn Ser Ala Pro Ser Gly
            260                 265                 270

Gly Ser Thr Pro Leu Thr Arg Met Pro Leu Ser Val Met Leu Val Val
        275                 280                 285

Ser Ser Glu Ala Ser Thr Leu Ser Thr Thr Pro Ala Ala Thr Asn Ile
290                 295                 300

Pro Val Ile Thr Ser Thr Glu Ala Ser Ser Ser Pro Thr Thr Ala Glu
305                 310                 315                 320

Gly Thr Ser Ile Pro Thr Ser Thr Tyr Thr Glu Gly Ser Thr Pro Leu
                325                 330                 335

Thr Ser Thr Pro Ala Ser Thr Met Pro Val Ala Thr Ser Glu Met Ser
            340                 345                 350

Thr Leu Ser Ile Thr Pro Val Asp Thr Ser Thr Leu Val Thr Thr Ser

-continued

```
            355                 360                 365
Thr Glu Pro Ser Ser Leu Pro Thr Thr Ala Glu Ala Thr Ser Met Leu
        370                 375                 380
Thr Ser Thr Leu Ser Glu Gly Ser Thr Pro Leu Thr Asn Met Pro Val
385                 390                 395                 400
Ser Thr Ile Leu Val Ala Ser Ser Glu Ala Ser Thr Thr Ser Thr Ile
                405                 410                 415
Pro Val Asp Ser Lys Thr Phe Val Thr Thr Ala Ser Glu Ala Ser Ser
            420                 425                 430
Ser Pro Thr Thr Ala Glu Asp Thr Ser Ile Ala Thr Ser Thr Pro Ser
        435                 440                 445
Glu Gly Ser Thr Pro Leu Thr Ser Met Pro Val Ser Thr Thr Pro Val
    450                 455                 460
Ala Ser Ser Glu Ala Ser Asn Leu Ser Thr Thr Pro Val Asp Ser Lys
465                 470                 475                 480
Thr Gln Val Thr Thr Ser Thr Glu Ala Ser Ser Pro Pro Thr Ala
                485                 490                 495
Glu Val Asn Ser Met Pro Thr Ser Thr Pro Ser Glu Gly Ser Thr Pro
            500                 505                 510
Leu Thr Ser Met Ser Val Ser Thr Met Pro Val Ala Ser Ser Glu Ala
        515                 520                 525
Ser Thr Leu Ser Thr Thr Pro Val Asp Thr Ser Thr Pro Val Thr Thr
    530                 535                 540
Ser Ser Glu Ala Ser Ser Ser Thr Thr Pro Glu Gly Thr Ser Ile
545                 550                 555                 560
Pro Thr Ser Thr Pro Ser Glu Gly Ser Thr Pro Leu Thr Asn Met Pro
                565                 570                 575
Val Ser Thr Arg Leu Val Val Ser Ser Glu Ala Ser Thr Thr Ser Thr
            580                 585                 590
Thr Pro Ala Asp Ser Asn Thr Phe Val Thr Thr Ser Ser Glu Ala Ser
        595                 600                 605
Ser Ser Ser Thr Thr Ala Glu Gly Thr Ser Met Pro Thr Ser Thr Tyr
    610                 615                 620
Ser Glu Arg Gly Thr Thr Ile Thr Ser Met Ser Val Ser Thr Thr Leu
625                 630                 635                 640
Val Ala Ser Ser Glu Ala Ser Thr Leu Ser Thr Thr Pro Val Asp Ser
                645                 650                 655
Asn Thr Pro Val Thr Thr Ser Thr Glu Ala Thr Ser Ser Ser Thr Thr
            660                 665                 670
Ala Glu Gly Thr Ser Met Pro Thr Ser Thr Tyr Thr Glu Gly Ser Thr
        675                 680                 685
Pro Leu Thr Ser Met Pro Val Asn Thr Thr Leu Val Ala Ser Ser Glu
    690                 695                 700
Ala Ser Thr Leu Ser Thr Thr Pro Val Asp Thr Ser Thr Pro Val Thr
705                 710                 715                 720
Thr Ser Thr Glu Ala Ser Ser Pro Thr Ala Asp Gly Ala Ser
                725                 730                 735
Met Pro Thr Ser Thr Pro Ser Glu Gly Ser Thr Pro Leu Thr Ser Met
            740                 745                 750
Pro Val Ser Lys Thr Leu Leu Thr Ser Ser Glu Ala Ser Thr Leu Ser
        755                 760                 765
Thr Thr Pro Leu Asp Thr Ser Thr His Ile Thr Thr Ser Thr Glu Ala
    770                 775                 780
```

-continued

```
Ser Cys Ser Pro Thr Thr Thr Glu Gly Thr Ser Met Pro Ile Ser Thr
785                 790                 795                 800

Pro Ser Glu Gly Ser Pro Leu Leu Thr Ser Ile Pro Val Ser Ile Thr
                805                 810                 815

Pro Val Thr Ser Pro Glu Ala Ser Thr Leu Ser Thr Thr Pro Val Asp
            820                 825                 830

Ser Asn Ser Pro Val Thr Thr Ser Thr Glu Val Ser Ser Ser Pro Thr
        835                 840                 845

Pro Ala Glu Gly Thr Ser Met Pro Thr Ser Thr Tyr Ser Glu Gly Arg
    850                 855                 860

Thr Pro Leu Thr Ser Met Pro Val Ser Thr Thr Leu Val Ala Thr Ser
865                 870                 875                 880

Ala Ile Ser Thr Leu Ser Thr Thr Pro Val Asp Thr Ser Thr Pro Val
                885                 890                 895

Thr Asn Ser Thr Glu Ala Arg Ser Ser Pro Thr Thr Ser Glu Gly Thr
                900                 905                 910

Ser Met Pro Thr Ser Thr Pro Gly Glu Gly Ser Thr Pro Leu Thr Ser
            915                 920                 925

Met Pro Asp Ser Thr Thr Pro Val Val Ser Ser Glu Ala Arg Thr Leu
930                 935                 940

Ser Ala Thr Pro Val Asp Thr Ser Thr Pro Val Thr Thr Ser Thr Glu
945                 950                 955                 960

Ala Thr Ser Ser Pro Thr Thr Ala Glu Gly Thr Ser Ile Pro Thr Ser
                965                 970                 975

Thr Pro Ser Glu Gly Thr Thr Pro Leu Thr Ser Thr Pro Val Ser His
            980                 985                 990

Thr Leu Val Ala Asn Ser Glu Ala Ser Thr Leu Ser Thr Thr Pro Val
                995                 1000                1005

Asp Ser Asn Thr Pro Leu Thr Thr Ser Thr Glu Ala Ser Ser Pro Pro
    1010                1015                1020

Pro Thr Ala Glu Gly Thr Ser Met Pro Thr Ser Thr Pro Ser Glu Gly
1025                1030                1035                1040

Ser Thr Pro Leu Thr Arg Met Pro Val Ser Thr Thr Met Val Ala Ser
                1045                1050                1055

Ser Glu Thr Ser Thr Leu Ser Thr Thr Pro Ala Asp Thr Ser Thr Pro
            1060                1065                1070

Val Thr Thr Tyr Ser Gln Ala Ser Ser Ser Thr Thr Ala Asp Gly
        1075                1080                1085

Thr Ser Met Pro Thr Ser Thr Tyr Ser Glu Gly Ser Thr Pro Leu Thr
    1090                1095                1100

Ser Val Pro Val Ser Thr Arg Leu Val Val Ser Ser Glu Ala Ser Thr
1105                1110                1115                1120

Leu Ser Thr Thr Pro Val Asp Thr Ser Ile Pro Val Thr Thr Ser Thr
                1125                1130                1135

Glu Ala Ser Ser Ser Pro Thr Thr Ala Glu Gly Thr Ser Ile Pro Thr
                1140                1145                1150

Ser Pro Pro Ser Glu Gly Thr Thr Pro Leu Ala Ser Met Pro Val Ser
            1155                1160                1165

Thr Thr Leu Val Val Ser Ser Glu Ala Asn Thr Leu Ser Thr Thr Pro
                1170                1175                1180

Val Asp Ser Lys Thr Gln Val Ala Thr Ser Thr Glu Ala Ser Ser Pro
1185                1190                1195                1200
```

-continued

```
Pro Pro Thr Ala Glu Val Thr Ser Met Pro Thr Ser Thr Pro Gly Glu
        1205                1210                1215

Arg Ser Thr Pro Leu Thr Ser Met Pro Val Arg His Thr Pro Val Ala
        1220                1225                1230

Ser Ser Glu Ala Ser Thr Leu Ser Thr Ser Pro Val Asp Thr Ser Thr
        1235                1240                1245

Pro Val Thr Thr Ser Ala Glu Thr Ser Ser Pro Thr Thr Ala Glu
        1250                1255                1260

Gly Thr Ser Leu Pro Thr Ser Thr Ser Glu Gly Ser Thr Leu Leu
1265            1270                1275                1280

Thr Ser Ile Pro Val Ser Thr Leu Val Thr Ser Pro Glu Ala Ser
                1285                1290                1295

Thr Leu Leu Thr Thr Pro Val Asp Thr Lys Gly Pro Val Val Thr Ser
        1300                1305                1310

Asn Glu Val Ser Ser Ser Pro Thr Pro Ala Glu Gly Thr Ser Met Pro
        1315                1320                1325

Thr Ser Thr Tyr Ser Glu Gly Arg Thr Pro Leu Thr Ser Ile Pro Val
        1330                1335                1340

Asn Thr Thr Leu Val Ala Ser Ser Ala Ile Ser Ile Leu Ser Thr Thr
1345            1350                1355                1360

Pro Val Asp Asn Ser Thr Pro Val Thr Thr Ser Thr Glu Ala Cys Ser
                1365                1370                1375

Ser Pro Thr Thr Ser Glu Gly Thr Ser Met Pro Asn Ser Asn Pro Ser
        1380                1385                1390

Glu Gly Thr Thr Pro Leu Thr Ser Ile Pro Val Ser Thr Thr Pro Val
        1395                1400                1405

Val Ser Ser Glu Ala Ser Thr Leu Ser Ala Thr Pro Val Asp Thr Ser
        1410                1415                1420

Thr Pro Gly Thr Thr Ser Ala Glu Ala Thr Ser Ser Pro Thr Thr Ala
1425            1430                1435                1440

Glu Gly Ile Ser Ile Pro Thr Ser Thr Pro Ser Glu Gly Lys Thr Pro
                1445                1450                1455

Leu Lys Ser Ile Pro Val Ser Asn Thr Pro Val Ala Asn Ser Glu Ala
        1460                1465                1470

Ser Thr Leu Ser Thr Thr Pro Val Asp Ser Asn Ser Pro Val Val Thr
        1475                1480                1485

Ser Thr Ala Val Ser Ser Pro Thr Pro Ala Glu Gly Thr Ser Ile
        1490                1495                1500

Ala Ile Ser Thr Pro Ser Glu Gly Ser Thr Ala Leu Thr Ser Ile Pro
1505            1510                1515                1520

Val Ser Thr Thr Val Ala Ser Ser Glu Ile Asn Ser Leu Ser Thr
        1525                1530                1535

Thr Pro Ala Val Thr Ser Thr Pro Val Thr Thr Tyr Ser Gln Ala Ser
        1540                1545                1550

Ser Ser Pro Thr Thr Ala Asp Gly Thr Ser Met Gln Thr Ser Thr Tyr
        1555                1560                1565

Ser Glu Gly Ser Thr Pro Leu Thr Ser Leu Pro Val Ser Thr Met Leu
        1570                1575                1580

Val Val Ser Ser Glu Ala Asn Thr Leu Ser Thr Thr Pro Ile Asp Ser
1585            1590                1595                1600

Lys Thr Gln Val Thr Ala Ser Thr Glu Ala Ser Ser Ser Thr Ala
                1605                1610                1615

Glu Gly Ser Ser Met Thr Ile Ser Thr Pro Ser Glu Gly Ser Pro Leu
```

-continued

```
                1620                1625                1630
Leu Thr Ser Ile Pro Val Ser Thr Thr Pro Val Ala Ser Pro Glu Ala
        1635                1640                1645

Ser Thr Leu Ser Thr Thr Pro Val Asp Ser Asn Ser Pro Val Ile Thr
    1650                1655                1660

Ser Thr Glu Val Ser Ser Pro Thr Pro Ala Glu Gly Thr Ser Met
1665                1670                1675                1680

Pro Thr Ser Thr Tyr Thr Glu Gly Arg Thr Pro Leu Thr Ser Ile Thr
                1685                1690                1695

Val Arg Thr Thr Pro Val Ala Ser Ser Ala Ile Ser Thr Leu Ser Thr
        1700                1705                1710

Thr Pro Val Asp Asn Ser Thr Pro Val Thr Thr Ser Thr Glu Ala Arg
    1715                1720                1725

Ser Ser Pro Thr Thr Ser Glu Gly Thr Ser Met Pro Asn Ser Thr Pro
    1730                1735                1740

Ser Glu Gly Thr Thr Pro Leu Thr Ser Ile Pro Val Ser Thr Thr Pro
1745                1750                1755                1760

Val Leu Ser Ser Glu Ala Ser Thr Leu Ser Ala Thr Pro Ile Asp Thr
        1765                1770                1775

Ser Thr Pro Val Thr Thr Ser Thr Glu Ala Thr Ser Ser Pro Thr Thr
        1780                1785                1790

Ala Glu Gly Thr Ser Ile Pro Thr Ser Thr Leu Ser Glu Gly Met Thr
        1795                1800                1805

Pro Leu Thr Ser Thr Pro Val Ser His Thr Leu Val Ala Asn Ser Glu
        1810                1815                1820

Ala Ser Thr Leu Ser Thr Thr Pro Val Asp Ser Asn Ser Pro Val Val
1825                1830                1835                1840

Thr Ser Thr Ala Val Ser Ser Pro Thr Pro Ala Glu Gly Thr Ser
                1845                1850                1855

Ile Ala Thr Ser Thr Pro Ser Glu Gly Ser Thr Ala Leu Thr Ser Ile
        1860                1865                1870

Pro Val Ser Thr Thr Thr Val Ala Ser Ser Glu Thr Asn Thr Leu Ser
        1875                1880                1885

Thr Thr Pro Ala Val Thr Ser Thr Pro Val Thr Thr Tyr Ala Gln Val
        1890                1895                1900

Ser Ser Ser Pro Thr Thr Ala Asp Gly Ser Ser Met Pro Thr Ser Thr
1905                1910                1915                1920

Pro Arg Glu Gly Arg Pro Leu Thr Ser Ile Pro Val Ser Thr Thr
                1925                1930                1935

Thr Val Ala Ser Ser Glu Ile Asn Thr Leu Ser Thr Thr Leu Ala Asp
        1940                1945                1950

Thr Arg Thr Pro Val Thr Thr Tyr Ser Gln Ala Ser Ser Ser Pro Thr
        1955                1960                1965

Thr Ala Asp Gly Thr Ser Met Pro Thr Pro Ala Tyr Ser Glu Gly Ser
        1970                1975                1980

Thr Pro Leu Thr Ser Met Pro Leu Ser Thr Thr Leu Val Val Ser Ser
1985                1990                1995                2000

Glu Ala Ser Thr Leu Ser Thr Thr Pro Val Asp Thr Ser Thr Pro Ala
                2005                2010                2015

Thr Thr Ser Thr Glu Gly Ser Ser Ser Pro Thr Thr Ala Gly Gly Thr
                2020                2025                2030

Ser Ile Gln Thr Ser Thr Pro Ser Glu Arg Thr Thr Pro Leu Ala Gly
        2035                2040                2045
```

-continued

```
Met Pro Val Ser Thr Thr Leu Val Val Ser Ser Glu Gly Asn Thr Leu
    2050                2055                2060

Ser Thr Thr Pro Val Asp Ser Lys Thr Gln Val Thr Asn Ser Thr Glu
2065                2070                2075                2080

Ala Ser Ser Ser Ala Thr Ala Glu Gly Ser Ser Met Thr Ile Ser Ala
                2085                2090                2095

Pro Ser Glu Gly Ser Pro Leu Leu Thr Ser Ile Pro Leu Ser Thr Thr
            2100                2105                2110

Pro Val Ala Ser Pro Glu Ala Ser Thr Leu Ser Thr Thr Pro Val Asp
        2115                2120                2125

Ser Asn Ser Pro Val Ile Thr Ser Thr Glu Val Ser Ser Ser Pro Ile
    2130                2135                2140

Pro Thr Glu Gly Thr Ser Met Gln Thr Ser Thr Tyr Ser Asp Arg Arg
2145                2150                2155                2160

Thr Pro Leu Thr Ser Met Pro Val Ser Thr Thr Val Ala Ser Ser
                2165                2170                2175

Ala Ile Ser Thr Leu Ser Thr Thr Pro Val Asp Thr Ser Thr Pro Val
            2180                2185                2190

Thr Asn Ser Thr Glu Ala Arg Ser Ser Pro Thr Thr Ser Glu Gly Thr
        2195                2200                2205

Ser Met Pro Thr Ser Thr Pro Ser Glu Gly Ser Thr Pro Phe Thr Ser
    2210                2215                2220

Met Pro Val Ser Thr Met Pro Val Val Thr Ser Glu Ala Ser Thr Leu
2225                2230                2235                2240

Ser Ala Thr Pro Val Asp Thr Ser Thr Pro Val Thr Thr Ser Thr Glu
                2245                2250                2255

Ala Thr Ser Ser Pro Thr Thr Ala Glu Gly Thr Ser Ile Pro Thr Ser
            2260                2265                2270

Thr Leu Ser Glu Gly Thr Thr Pro Leu Thr Ser Ile Pro Val Ser His
        2275                2280                2285

Thr Leu Val Ala Asn Ser Glu Val Ser Thr Leu Ser Thr Thr Pro Val
    2290                2295                2300

Asp Ser Asn Thr Pro Phe Thr Thr Ser Thr Glu Ala Ser Ser Pro Pro
2305                2310                2315                2320

Pro Thr Ala Glu Gly Thr Ser Met Pro Thr Ser Thr Ser Ser Glu Gly
                2325                2330                2335

Asn Thr Pro Leu Thr Arg Met Pro Val Ser Thr Thr Met Val Ala Ser
            2340                2345                2350

Phe Glu Thr Ser Thr Leu Ser Thr Thr Pro Ala Asp Thr Ser Thr Pro
        2355                2360                2365

Val Thr Thr Tyr Ser Gln Ala Gly Ser Ser Pro Thr Thr Ala Asp Asp
    2370                2375                2380

Thr Ser Met Pro Thr Ser Thr Tyr Ser Glu Gly Ser Thr Pro Leu Thr
2385                2390                2395                2400

Ser Val Pro Val Ser Thr Met Pro Val Val Ser Ser Glu Ala Ser Thr
                2405                2410                2415

His Ser Thr Thr Pro Val Asp Thr Ser Thr Pro Val Thr Thr Ser Thr
            2420                2425                2430

Glu Ala Ser Ser Ser Pro Thr Thr Ala Glu Gly Thr Ser Ile Pro Thr
        2435                2440                2445

Ser Pro Pro Ser Glu Gly Thr Thr Pro Leu Ala Ser Met Pro Val Ser
    2450                2455                2460
```

-continued

```
Thr Thr Pro Val Val Ser Ser Glu Ala Gly Thr Leu Ser Thr Thr Pro
2465                2470                2475                2480

Val Asp Thr Ser Thr Pro Met Thr Thr Ser Thr Glu Ala Ser Ser Ser
            2485                2490                2495

Pro Thr Thr Ala Glu Asp Ile Val Val Pro Ile Ser Thr Ala Ser Glu
        2500                2505                2510

Gly Ser Thr Leu Leu Thr Ser Ile Pro Val Ser Thr Thr Pro Val Ala
            2515                2520                2525

Ser Pro Glu Ala Ser Thr Leu Ser Thr Thr Pro Val Asp Ser Asn Ser
        2530                2535                2540

Pro Val Val Thr Ser Thr Glu Ile Ser Ser Ser Ala Thr Ser Ala Glu
2545                2550                2555                2560

Gly Thr Ser Met Pro Thr Ser Thr Tyr Ser Glu Gly Ser Thr Pro Leu
            2565                2570                2575

Arg Ser Met Pro Val Ser Thr Lys Pro Leu Ala Ser Ser Glu Ala Ser
            2580                2585                2590

Thr Leu Ser Thr Thr Pro Val Asp Thr Ser Ile Pro Val Thr Thr Ser
            2595                2600                2605

Thr Glu Thr Ser Ser Ser Pro Thr Thr Ala Lys Asp Thr Ser Met Pro
2610                2615                2620

Ile Ser Thr Pro Ser Glu Val Ser Thr Ser Leu Thr Ser Ile Leu Val
2625                2630                2635                2640

Ser Thr Met Pro Val Ala Ser Ser Glu Ala Ser Thr Leu Ser Thr Thr
            2645                2650                2655

Pro Val Asp Thr Arg Thr Leu Val Thr Thr Ser Thr Gly Thr Ser Ser
            2660                2665                2670

Ser Pro Thr Thr Ala Glu Gly Ser Ser Met Pro Thr Ser Thr Pro Gly
            2675                2680                2685

Glu Arg Ser Thr Pro Leu Thr Asn Ile Leu Val Ser Thr Thr Leu Leu
            2690                2695                2700

Ala Asn Ser Glu Ala Ser Thr Leu Ser Thr Thr Pro Val Asp Thr Ser
2705                2710                2715                2720

Thr Pro Val Thr Thr Ser Ala Glu Ala Ser Ser Ser Pro Thr Thr Ala
            2725                2730                2735

Glu Gly Thr Ser Met Arg Ile Ser Thr Pro Ser Asp Gly Ser Thr Pro
            2740                2745                2750

Leu Thr Ser Ile Leu Val Ser Thr Leu Pro Val Ala Ser Ser Glu Ala
            2755                2760                2765

Ser Thr Val Ser Thr Thr Ala Val Asp Thr Ser Ile Pro Val Thr Thr
            2770                2775                2780

Ser Thr Glu Ala Ser Ser Pro Thr Thr Ala Glu Val Thr Ser Met
2785                2790                2795                2800

Pro Thr Ser Thr Pro Ser Glu Thr Ser Thr Pro Leu Thr Ser Met Pro
            2805                2810                2815

Val Asn His Thr Pro Val Ala Ser Ser Glu Ala Gly Thr Leu Ser Thr
            2820                2825                2830

Thr Pro Val Asp Thr Ser Thr Pro Val Thr Thr Ser Thr Lys Ala Ser
            2835                2840                2845

Ser Ser Pro Thr Thr Ala Glu Gly Ile Val Val Pro Ile Ser Thr Ala
            2850                2855                2860

Ser Glu Gly Ser Thr Leu Leu Thr Ser Ile Pro Val Ser Thr Thr Pro
            2865                2870                2875                2880

Val Ala Ser Ser Glu Ala Ser Thr Leu Ser Thr Thr Pro Val Asp Thr
```

-continued

```
                        2885                2890                2895
Ser Ile Pro Val Thr Thr Ser Thr Glu Gly Ser Ser Pro Thr Thr
                2900                2905                2910
Ala Glu Gly Thr Ser Met Pro Ile Ser Thr Pro Ser Glu Val Ser Thr
                2915                2920                2925
Pro Leu Thr Ser Ile Leu Val Ser Thr Val Pro Val Ala Gly Ser Glu
                2930                2935                2940
Ala Ser Thr Leu Ser Thr Thr Pro Val Asp Thr Arg Thr Pro Val Thr
2945                2950                2955                2960
Thr Ser Ala Glu Ala Ser Ser Pro Thr Thr Ala Glu Gly Thr Ser
                2965                2970                2975
Met Pro Ile Ser Thr Pro Gly Glu Arg Arg Thr Pro Leu Thr Ser Met
                2980                2985                2990
Ser Val Ser Thr Met Pro Val Ala Ser Ser Glu Ala Ser Thr Leu Ser
                2995                3000                3005
Arg Thr Pro Ala Asp Thr Ser Thr Pro Val Thr Thr Ser Thr Glu Ala
3010                3015                3020
Ser Ser Ser Pro Thr Thr Ala Glu Gly Thr Gly Ile Pro Ile Ser Thr
3025                3030                3035                3040
Pro Ser Glu Gly Ser Thr Pro Leu Thr Ser Ile Pro Val Ser Thr Thr
                3045                3050                3055
Pro Val Ala Ile Pro Glu Ala Ser Thr Leu Ser Thr Thr Pro Val Asp
                3060                3065                3070
Ser Asn Ser Pro Val Val Thr Ser Thr Glu Val Ser Ser Ser Pro Thr
                3075                3080                3085
Pro Ala Glu Gly Thr Ser Met Pro Ile Ser Thr Tyr Ser Glu Gly Ser
                3090                3095                3100
Thr Pro Leu Thr Gly Val Pro Val Ser Thr Thr Pro Val Thr Ser Ser
3105                3110                3115                3120
Ala Ile Ser Thr Leu Ser Thr Thr Pro Val Asp Thr Ser Thr Pro Val
                3125                3130                3135
Thr Thr Ser Thr Glu Ala His Ser Ser Pro Thr Thr Ser Glu Gly Thr
                3140                3145                3150
Ser Met Pro Thr Ser Thr Pro Ser Glu Gly Ser Thr Pro Leu Thr Tyr
                3155                3160                3165
Met Pro Val Ser Thr Met Leu Val Ser Ser Glu Asp Ser Thr Leu
                3170                3175                3180
Ser Ala Thr Pro Val Asp Thr Ser Thr Pro Val Thr Thr Ser Thr Glu
3185                3190                3195                3200
Ala Thr Ser Ser Thr Thr Ala Glu Gly Thr Ser Ile Pro Thr Ser Thr
                3205                3210                3215
Pro Ser Glu Gly Met Thr Pro Leu Thr Ser Val Pro Val Ser Asn Thr
                3220                3225                3230
Pro Val Ala Ser Ser Glu Ala Ser Ile Leu Ser Thr Thr Pro Val Asp
                3235                3240                3245
Ser Asn Thr Pro Leu Thr Thr Ser Thr Glu Ala Ser Ser Ser Pro Pro
                3250                3255                3260
Thr Ala Glu Gly Thr Ser Met Pro Ser Thr Pro Ser Glu Gly Ser
3265                3270                3275                3280
Thr Pro Leu Thr Ser Met Pro Val Ser Thr Thr Val Ala Ser Ser
                3285                3290                3295
Glu Thr Ser Thr Leu Ser Thr Thr Pro Ala Asp Thr Ser Thr Pro Val
                3300                3305                3310
```

-continued

Thr Thr Tyr Ser Gln Ala Ser Ser Pro Ile Ala Asp Gly Thr
         3315             3320             3325

Ser Met Pro Thr Ser Thr Tyr Ser Glu Gly Ser Thr Pro Leu Thr Asn
         3330             3335             3340

Met Ser Phe Ser Thr Thr Pro Val Val Ser Glu Ala Ser Thr Leu
3345             3350             3355             3360

Ser Thr Thr Pro Val Asp Thr Ser Thr Pro Val Thr Ser Thr Glu
             3365             3370             3375

Ala Ser Leu Ser Pro Thr Thr Ala Glu Gly Thr Ser Ile Pro Thr Ser
             3380             3385             3390

Ser Pro Ser Glu Gly Thr Thr Pro Leu Ala Ser Met Pro Val Ser Thr
             3395             3400             3405

Thr Pro Val Val Ser Ser Glu Val Asn Thr Leu Ser Thr Thr Pro Val
         3410             3415             3420

Asp Ser Asn Thr Leu Val Thr Thr Ser Thr Glu Ala Ser Ser Pro
3425             3430             3435             3440

Thr Ile Ala Glu Gly Thr Ser Leu Pro Thr Ser Thr Thr Ser Glu Gly
             3445             3450             3455

Ser Thr Pro Leu Ser Ile Met Pro Leu Ser Thr Thr Pro Val Ala Ser
             3460             3465             3470

Ser Glu Ala Ser Thr Leu Ser Thr Thr Pro Val Asp Thr Ser Thr Pro
             3475             3480             3485

Val Thr Thr Ser Ser Pro Thr Asn Ser Ser Pro Thr Thr Ala Glu Val
         3490             3495             3500

Thr Ser Met Pro Thr Ser Thr Ala Gly Glu Gly Ser Thr Pro Leu Thr
3505             3510             3515             3520

Asn Met Pro Val Ser Thr Thr Pro Val Ala Ser Ser Glu Ala Ser Thr
             3525             3530             3535

Leu Ser Thr Thr Pro Val Asp Ser Asn Thr Phe Val Thr Ser Ser Ser
             3540             3545             3550

Gln Ala Ser Ser Ser Pro Ala Thr Leu Gln Val Thr Thr Met Arg Met
             3555             3560             3565

Ser Thr Pro Ser Glu Gly Ser Ser Ser Leu Thr Thr Met Leu Leu Ser
         3570             3575             3580

Ser Thr Tyr Val Thr Ser Ser Glu Ala Ser Thr Pro Ser Thr Pro Ser
3585             3590             3595             3600

Val Asp Arg Ser Thr Pro Val Thr Thr Ser Thr Gln Ser Asn Ser Thr
             3605             3610             3615

Pro Thr Pro Pro Glu Val Ile Thr Leu Pro Met Ser Thr Pro Ser Glu
         3620             3625             3630

Val Ser Thr Pro Leu Thr Ile Met Pro Val Ser Thr Thr Ser Val Thr
             3635             3640             3645

Ile Ser Glu Ala Gly Thr Ala Ser Thr Leu Pro Val Asp Thr Ser Thr
             3650             3655             3660

Pro Val Ile Thr Ser Thr Gln Val Ser Ser Pro Val Thr Pro Glu
3665             3670             3675             3680

Gly Thr Thr Met Pro Ile Trp Thr Pro Ser Glu Gly Ser Thr Pro Leu
             3685             3690             3695

Thr Thr Met Pro Val Ser Thr Thr Arg Val Thr Ser Ser Glu Gly Ser
         3700             3705             3710

Thr Leu Ser Thr Pro Ser Val Val Thr Ser Thr Pro Val Thr Thr Ser
         3715             3720             3725

-continued

```
Thr Glu Ala Ile Ser Ser Ser Ala Thr Leu Asp Ser Thr Thr Met Ser
    3730            3735                3740
Val Ser Met Pro Met Glu Ile Ser Thr Leu Gly Thr Thr Ile Leu Val
3745                3750            3755                3760
Ser Thr Thr Pro Val Thr Arg Phe Pro Glu Ser Ser Thr Pro Ser Ile
            3765                3770                3775
Pro Ser Val Tyr Thr Ser Met Ser Met Thr Thr Ala Ser Glu Gly Ser
            3780                3785                3790
Ser Ser Pro Thr Thr Leu Glu Gly Thr Thr Thr Met Pro Met Ser Thr
            3795                3800                3805
Thr Ser Glu Arg Ser Thr Leu Leu Thr Thr Val Leu Ile Ser Pro Ile
        3810                3815                3820
Ser Val Met Ser Pro Ser Glu Ala Ser Thr Leu Ser Thr Pro Pro Gly
3825                3830                3835                3840
Asp Thr Ser Thr Pro Leu Leu Thr Ser Thr Lys Ala Gly Ser Phe Ser
            3845                3850                3855
Ile Pro Ala Glu Val Thr Thr Ile Arg Ile Ser Ile Thr Ser Glu Arg
            3860                3865                3870
Ser Thr Pro Leu Thr Thr Leu Leu Val Ser Thr Thr Leu Pro Thr Ser
        3875                3880                3885
Phe Pro Gly Ala Ser Ile Ala Ser Thr Pro Leu Asp Thr Ser Thr
        3890                3895                3900
Thr Phe Thr Pro Ser Thr Asp Thr Ala Ser Thr Pro Thr Ile Pro Val
3905                3910                3915                3920
Ala Thr Thr Ile Ser Val Ser Val Ile Thr Glu Gly Ser Thr Pro Gly
            3925                3930                3935
Thr Thr Ile Phe Ile Pro Ser Thr Pro Val Thr Ser Ser Thr Ala Asp
        3940                3945                3950
Val Phe Pro Ala Thr Thr Gly Ala Val Ser Thr Pro Val Ile Thr Ser
            3955                3960                3965
Thr Glu Leu Asn Thr Pro Ser Thr Ser Ser Ser Thr Thr Thr Ser
        3970                3975                3980
Phe Ser Thr Thr Lys Glu Phe Thr Thr Pro Ala Met Thr Thr Ala Ala
3985                3990                3995                4000
Pro Leu Thr Tyr Val Thr Met Ser Thr Ala Pro Ser Thr Pro Arg Thr
            4005                4010                4015
Thr Ser Arg Gly Cys Thr Thr Ser Ala Ser Thr Leu Ser Ala Thr Ser
            4020                4025                4030
Thr Pro His Thr Ser Thr Ser Val Thr Thr Arg Pro Val Thr Pro Ser
        4035                4040                4045
Ser Glu Ser Ser Arg Pro Ser Thr Ile Thr Ser His Thr Ile Pro Pro
        4050                4055                4060
Thr Phe Pro Pro Ala His Ser Ser Thr Pro Thr Thr Ser Ala Ser
4065                4070                4075                4080
Ser Thr Thr Val Asn Pro Glu Ala Val Thr Thr Met Thr Thr Arg Thr
            4085                4090                4095
Lys Pro Ser Thr Arg Thr Thr Ser Phe Pro Thr Val Thr Thr Thr Ala
        4100                4105                4110
Val Pro Thr Asn Thr Thr Ile Lys Ser Asn Pro Thr Ser Thr Pro Thr
        4115                4120                4125
Val Pro Arg Thr Thr Thr Cys Phe Gly Asp Gly Cys Gln Asn Thr Ala
        4130                4135                4140
Ser Arg Cys Lys Asn Gly Gly Thr Trp Asp Gly Leu Lys Cys Gln Cys
```

-continued

```
               4145                4150                4155                4160

Pro Asn Leu Tyr Tyr Gly Glu Leu Cys Glu Glu Val Val Ser Ser Ile
                4165                4170                4175

Asp Ile Gly Pro Pro Glu Thr Ile Ser Ala Gln Met Glu Leu Thr Val
                4180                4185                4190

Thr Val Thr Ser Val Lys Phe Thr Glu Glu Leu Lys Asn His Ser Ser
                4195                4200                4205

Gln Glu Phe Gln Glu Phe Lys Gln Thr Phe Thr Glu Gln Met Asn Ile
                4210                4215                4220

Val Tyr Ser Gly Ile Pro Glu Tyr Val Gly Val Asn Ile Thr Lys Leu
4225                4230                4235                4240

Arg Leu Gly Ser Val Val Glu His Asp Val Leu Arg Thr Lys
                4245                4250                4255

Tyr Thr Pro Glu Tyr Lys Thr Val Leu Asp Asn Ala Xaa Glu Val Val
                4260                4265                4270

Lys Glu Lys Ile Thr Lys Val Thr Thr Gln Gln Ile Met Ile Asn Asp
                4275                4280                4285

Ile Cys Ser Asp Met Met Cys Phe Asn Thr Thr Gly Thr Gln Val Gln
                4290                4295                4300

Asn Ile Thr Val Thr Gln Tyr Asp Pro Glu Glu Asp Cys Arg Lys Met
4305                4310                4315                4320

Ala Lys Glu Tyr Gly Asp Tyr Phe Val Val Glu Tyr Arg Asp Gln Lys
                4325                4330                4335

Pro Tyr Cys Ile Ser Pro Cys Glu Pro Gly Phe Ser Val Ser Lys Asn
                4340                4345                4350

Cys Asn Leu Gly Lys Cys Gln Met Ser Leu Ser Gly Pro Gln Cys Leu
                4355                4360                4365

Cys Val Thr Thr Glu Thr His Trp Tyr Ser Gly Glu Thr Cys Asn Gln
                4370                4375                4380

Gly Thr Gln Lys Ser Leu Val Tyr Gly Leu Val Gly Ala Gly Val Val
4385                4390                4395                4400

Leu Met Leu Ile Ile Leu Val Ala Leu Leu Met Leu Val Phe Arg Ser
                4405                4410                4415

Lys Arg Glu Val Lys Arg Gln Lys Tyr Arg Leu Ser Gln Leu Tyr Lys
                4420                4425                4430

Trp Gln Glu Glu Asp Ser Gly Pro Ala Pro Gly Thr Phe Gln Asn Ile
                4435                4440                4445

Gly Phe Asp Ile Cys Gln Asp Asp Asp Ser Ile His Leu Glu Ser Ile
                4450                4455                4460

Tyr Ser Asn Phe Gln Pro Ser Leu Arg His Ile Asp Pro Glu Thr Lys
4465                4470                4475                4480

Ile Arg Ile Gln Arg Pro Gln Val Met Thr Thr Ser Phe
                4485                4490

<210> SEQ ID NO 4
<211> LENGTH: 4262
<212> TYPE: PRT
<213> ORGANISM: Homo Sapiens

<400> SEQUENCE: 4

Met Pro Arg Pro Gly Thr Met Ala Leu Cys Leu Leu Thr Leu Val Leu
 1               5                  10                  15

Ser Leu Leu Pro Pro Gln Ala Ala Ala Glu Gln Gly Leu Ser Val Asn
                20                  25                  30
```

-continued

```
Arg Ala Val Trp Asp Gly Gly Cys Ile Ser Gln Gly Asp Val Leu
         35              40                  45

Asn Arg Gln Cys Gln Gln Leu Ser Gln His Val Arg Thr Gly Ser Ala
 50              55                  60

Thr Asn Thr Ala Thr Gly Thr Thr Ser Thr Asn Val Val Glu Pro Arg
 65              70                  75                   80

Met Tyr Leu Ser Cys Ser Thr Asn Pro Glu Met Thr Ser Ile Glu Ser
                 85                  90                  95

Ser Val Thr Ser Asp Thr Pro Gly Val Ser Ser Thr Arg Met Thr Pro
            100                 105                 110

Thr Glu Ser Arg Thr Thr Ser Glu Ser Thr Ser Asp Ser Thr Thr Leu
            115                 120                 125

Phe Pro Ser Pro Thr Glu Asp Thr Ser Ser Pro Thr Thr Pro Glu Gly
130                 135                 140

Thr Asp Val Pro Met Ser Thr Pro Ser Glu Glu Ser Ile Ser Ser Thr
145                 150                 155                 160

Met Ala Phe Val Ser Thr Ala Pro Leu Pro Ser Phe Glu Ala Tyr Thr
                165                 170                 175

Ser Leu Thr Tyr Lys Val Asp Met Ser Thr Pro Leu Thr Thr Ser Thr
            180                 185                 190

Gln Ala Ser Ser Ser Pro Thr Thr Pro Glu Ser Thr Thr Ile Pro Lys
            195                 200                 205

Ser Thr Asn Ser Glu Gly Ser Thr Pro Leu Thr Ser Met Pro Ala Ser
210                 215                 220

Thr Met Lys Val Ala Ser Ser Glu Ala Ile Thr Leu Leu Thr Thr Pro
225                 230                 235                 240

Val Glu Ile Ser Thr Pro Val Thr Ile Ser Ala Gln Ala Ser Ser Ser
                245                 250                 255

Pro Thr Thr Ala Glu Gly Pro Ser Leu Ser Asn Ser Ala Pro Ser Gly
            260                 265                 270

Gly Ser Thr Pro Leu Thr Arg Met Pro Leu Ser Val Met Leu Val Val
            275                 280                 285

Ser Ser Glu Ala Ser Thr Leu Ser Thr Thr Pro Ala Ala Thr Asn Ile
290                 295                 300

Pro Val Ile Thr Ser Thr Glu Ala Ser Ser Ser Pro Thr Thr Ala Glu
305                 310                 315                 320

Gly Thr Ser Ile Pro Thr Ser Thr Tyr Thr Glu Gly Ser Thr Pro Leu
                325                 330                 335

Thr Ser Thr Pro Ala Ser Thr Met Pro Val Ala Thr Ser Glu Met Ser
            340                 345                 350

Thr Leu Ser Ile Thr Pro Val Asp Thr Ser Thr Leu Val Thr Thr Ser
            355                 360                 365

Thr Glu Pro Ser Ser Leu Pro Thr Thr Ala Glu Ala Thr Ser Met Leu
370                 375                 380

Thr Ser Thr Leu Ser Glu Gly Ser Thr Pro Leu Thr Asn Met Pro Val
385                 390                 395                 400

Ser Thr Ile Leu Val Ala Ser Ser Glu Ala Ser Thr Ser Thr Ile
                405                 410                 415

Pro Val Asp Ser Lys Thr Phe Val Thr Thr Ala Ser Glu Ala Ser Ser
            420                 425                 430

Ser Pro Thr Thr Ala Glu Asp Thr Ser Ile Ala Thr Ser Thr Pro Ser
            435                 440                 445

Glu Gly Ser Thr Pro Leu Thr Ser Met Pro Val Ser Thr Thr Pro Val
```

```
                450              455              460
Ala Ser Ser Glu Ala Ser Asn Leu Ser Thr Thr Pro Val Asp Ser Lys
465              470              475              480

Thr Gln Val Thr Thr Ser Thr Glu Ala Ser Ser Pro Pro Thr Ala
                485              490              495

Glu Val Asn Ser Met Pro Thr Ser Thr Pro Ser Glu Gly Ser Thr Pro
                500              505              510

Leu Thr Ser Met Ser Val Ser Thr Met Pro Val Ala Ser Ser Glu Ala
                515              520              525

Ser Thr Leu Ser Thr Thr Pro Val Asp Thr Ser Thr Pro Val Thr Thr
530              535              540

Ser Ser Glu Ala Ser Ser Ser Thr Thr Pro Glu Gly Thr Ser Ile
545              550              555              560

Pro Thr Ser Thr Pro Ser Glu Gly Ser Thr Pro Leu Thr Asn Met Pro
                565              570              575

Val Ser Thr Arg Leu Val Val Ser Ser Glu Ala Ser Thr Thr Ser Thr
                580              585              590

Thr Pro Ala Asp Ser Asn Thr Phe Val Thr Thr Ser Ser Glu Ala Ser
                595              600              605

Ser Ser Ser Thr Thr Ala Glu Gly Thr Ser Met Pro Thr Ser Thr Tyr
610              615              620

Ser Glu Arg Gly Thr Thr Ile Thr Ser Met Ser Val Ser Thr Thr Leu
625              630              635              640

Val Ala Ser Ser Glu Ala Ser Thr Leu Ser Thr Thr Pro Val Asp Ser
                645              650              655

Asn Thr Pro Val Thr Thr Ser Thr Glu Ala Thr Ser Ser Ser Thr Thr
                660              665              670

Ala Glu Gly Thr Ser Met Pro Thr Ser Thr Tyr Thr Glu Gly Ser Thr
                675              680              685

Pro Leu Thr Ser Met Pro Val Asn Thr Thr Leu Val Ala Ser Ser Glu
                690              695              700

Ala Ser Thr Leu Ser Thr Thr Pro Val Asp Thr Ser Thr Pro Val Thr
705              710              715              720

Thr Ser Thr Glu Ala Ser Ser Pro Thr Thr Ala Asp Gly Ala Ser
                725              730              735

Met Pro Thr Ser Thr Pro Ser Glu Gly Ser Thr Pro Leu Thr Ser Met
                740              745              750

Pro Val Ser Lys Thr Leu Leu Thr Ser Ser Glu Ala Ser Thr Leu Ser
                755              760              765

Thr Thr Pro Leu Asp Thr Ser Thr His Ile Thr Thr Ser Thr Glu Ala
770              775              780

Ser Cys Ser Pro Thr Thr Thr Glu Gly Thr Ser Met Pro Ile Ser Thr
785              790              795              800

Pro Ser Glu Gly Ser Pro Leu Leu Thr Ser Ile Pro Val Ser Ile Thr
                805              810              815

Pro Val Thr Ser Pro Glu Ala Ser Thr Leu Ser Thr Thr Pro Val Asp
                820              825              830

Ser Asn Ser Pro Val Thr Thr Ser Thr Glu Val Ser Ser Ser Pro Thr
                835              840              845

Pro Ala Glu Gly Thr Ser Met Pro Thr Ser Thr Tyr Ser Glu Gly Arg
                850              855              860

Thr Pro Leu Thr Ser Met Pro Val Ser Thr Thr Leu Val Ala Thr Ser
865              870              875              880
```

-continued

```
Ala Ile Ser Thr Leu Ser Thr Thr Pro Val Asp Thr Ser Thr Pro Val
            885                 890                 895

Thr Asn Ser Thr Glu Ala Arg Ser Ser Pro Thr Thr Ser Glu Gly Thr
            900                 905                 910

Ser Met Pro Thr Ser Thr Pro Gly Glu Gly Ser Thr Pro Leu Thr Ser
            915                 920                 925

Met Pro Asp Ser Thr Thr Pro Val Val Ser Ser Glu Ala Arg Thr Leu
            930                 935                 940

Ser Ala Thr Pro Val Asp Thr Ser Thr Pro Val Thr Thr Ser Thr Glu
945                 950                 955                 960

Ala Thr Ser Ser Pro Thr Thr Ala Glu Gly Thr Ser Ile Pro Thr Ser
            965                 970                 975

Thr Pro Ser Glu Gly Thr Thr Pro Leu Thr Ser Thr Pro Val Ser His
            980                 985                 990

Thr Leu Val Ala Asn Ser Glu Ala Ser Thr Leu Ser Thr Thr Pro Val
            995                 1000                1005

Asp Ser Asn Thr Pro Leu Thr Thr Ser Thr Glu Ala Ser Ser Pro Pro
            1010                1015                1020

Pro Thr Ala Glu Gly Thr Ser Met Pro Thr Ser Thr Pro Ser Glu Gly
1025                1030                1035                1040

Ser Thr Pro Leu Thr Arg Met Pro Val Ser Thr Thr Met Val Ala Ser
            1045                1050                1055

Ser Glu Thr Ser Thr Leu Ser Thr Thr Pro Ala Asp Thr Ser Thr Pro
            1060                1065                1070

Val Thr Thr Tyr Ser Gln Ala Ser Ser Ser Thr Thr Ala Asp Gly
            1075                1080                1085

Thr Ser Met Pro Thr Ser Thr Tyr Ser Glu Gly Ser Thr Pro Leu Thr
            1090                1095                1100

Ser Val Pro Val Ser Thr Arg Leu Val Val Ser Ser Glu Ala Ser Thr
1105                1110                1115                1120

Leu Ser Thr Thr Pro Val Asp Thr Ser Ile Pro Val Thr Thr Ser Thr
            1125                1130                1135

Glu Ala Ser Ser Pro Thr Thr Ala Glu Gly Thr Ser Ile Pro Thr
            1140                1145                1150

Ser Pro Pro Ser Glu Gly Thr Thr Pro Leu Ala Ser Met Pro Val Ser
            1155                1160                1165

Thr Thr Leu Val Val Ser Ser Glu Ala Asn Thr Leu Ser Thr Thr Pro
            1170                1175                1180

Val Asp Ser Lys Thr Gln Val Ala Thr Ser Thr Glu Ala Ser Ser Pro
1185                1190                1195                1200

Pro Pro Thr Ala Glu Val Ser Met Pro Thr Ser Thr Pro Gly Glu
            1205                1210                1215

Arg Ser Thr Pro Leu Thr Ser Met Pro Val Arg His Thr Pro Val Ala
            1220                1225                1230

Ser Ser Glu Ala Ser Thr Leu Ser Thr Ser Pro Val Asp Thr Ser Thr
            1235                1240                1245

Pro Val Thr Thr Ser Ala Glu Thr Ser Ser Pro Thr Thr Ala Glu
            1250                1255                1260

Gly Thr Ser Leu Pro Thr Ser Thr Ser Glu Gly Ser Thr Leu Leu
1265                1270                1275                1280

Thr Ser Ile Pro Val Ser Thr Thr Leu Val Thr Ser Pro Glu Ala Ser
            1285                1290                1295
```

```
Thr Leu Leu Thr Thr Pro Val Asp Lys Gly Pro Val Val Thr Ser
        1300                1305                1310

Asn Glu Val Ser Ser Ser Pro Thr Pro Ala Glu Gly Thr Ser Met Pro
        1315                1320                1325

Thr Ser Thr Tyr Ser Glu Gly Arg Thr Pro Leu Thr Ser Ile Pro Val
        1330                1335                1340

Asn Thr Thr Leu Val Ala Ser Ser Ala Ile Ser Ile Leu Ser Thr Thr
1345                1350                1355                1360

Pro Val Asp Asn Ser Thr Pro Val Thr Thr Ser Thr Glu Ala Cys Ser
                1365                1370                1375

Ser Pro Thr Thr Ser Glu Gly Thr Ser Met Pro Asn Ser Asn Pro Ser
                1380                1385                1390

Glu Gly Thr Thr Pro Leu Thr Ser Ile Pro Val Ser Thr Thr Pro Val
        1395                1400                1405

Val Ser Ser Glu Ala Ser Thr Leu Ser Ala Thr Pro Val Asp Thr Ser
        1410                1415                1420

Thr Pro Gly Thr Thr Ser Ala Glu Ala Thr Ser Ser Pro Thr Thr Ala
1425                1430                1435                1440

Glu Gly Ile Ser Ile Pro Thr Ser Thr Pro Ser Glu Gly Lys Thr Pro
                1445                1450                1455

Leu Lys Ser Ile Pro Val Ser Asn Thr Pro Val Ala Asn Ser Glu Ala
                1460                1465                1470

Ser Thr Leu Ser Thr Thr Pro Val Asp Ser Asn Ser Pro Val Val Thr
                1475                1480                1485

Ser Thr Ala Val Ser Ser Pro Thr Pro Ala Glu Gly Thr Ser Ile
        1490                1495                1500

Ala Ile Ser Thr Pro Ser Glu Gly Ser Thr Ala Leu Thr Ser Ile Pro
1505                1510                1515                1520

Val Ser Thr Thr Thr Val Ala Ser Ser Glu Ile Asn Ser Leu Ser Thr
                1525                1530                1535

Thr Pro Ala Val Thr Ser Thr Pro Val Thr Thr Tyr Ser Gln Ala Ser
                1540                1545                1550

Ser Ser Pro Thr Thr Ala Asp Gly Thr Ser Met Gln Thr Ser Thr Tyr
                1555                1560                1565

Ser Glu Gly Ser Thr Pro Leu Thr Ser Leu Pro Val Ser Thr Met Leu
        1570                1575                1580

Val Val Ser Ser Glu Ala Asn Thr Leu Ser Thr Thr Pro Ile Asp Ser
1585                1590                1595                1600

Lys Thr Gln Val Thr Ala Ser Thr Glu Ala Ser Ser Thr Thr Ala
                1605                1610                1615

Glu Gly Ser Ser Met Thr Ile Ser Thr Pro Ser Glu Gly Ser Pro Leu
        1620                1625                1630

Leu Thr Ser Ile Pro Val Ser Thr Thr Pro Val Ala Ser Pro Glu Ala
        1635                1640                1645

Ser Thr Leu Ser Thr Thr Pro Val Asp Ser Asn Ser Pro Val Ile Thr
        1650                1655                1660

Ser Thr Glu Val Ser Ser Ser Pro Thr Pro Ala Glu Gly Thr Ser Met
1665                1670                1675                1680

Pro Thr Ser Thr Tyr Thr Glu Gly Arg Thr Pro Leu Thr Ser Ile Thr
                1685                1690                1695

Val Arg Thr Thr Pro Val Ala Ser Ser Ala Ile Ser Thr Leu Ser Thr
                1700                1705                1710

Thr Pro Val Asp Asn Ser Thr Pro Val Thr Thr Ser Thr Glu Ala Arg
```

-continued

```
            1715                1720                1725
Ser Ser Pro Thr Thr Ser Glu Gly Thr Ser Met Pro Asn Ser Thr Pro
    1730                1735                1740
Ser Glu Gly Thr Thr Pro Leu Thr Ser Ile Pro Val Ser Thr Thr Pro
1745                1750                1755                1760
Val Leu Ser Ser Glu Ala Ser Thr Leu Ser Ala Thr Pro Ile Asp Thr
            1765                1770                1775
Ser Thr Pro Val Thr Thr Ser Thr Glu Ala Thr Ser Ser Pro Thr Thr
            1780                1785                1790
Ala Glu Gly Thr Ser Ile Pro Thr Ser Thr Leu Ser Glu Gly Met Thr
            1795                1800                1805
Pro Leu Thr Ser Thr Pro Val Ser His Thr Leu Val Ala Asn Ser Glu
            1810                1815                1820
Ala Ser Thr Leu Ser Thr Thr Pro Val Asp Ser Asn Ser Pro Val Val
            1825                1830                1835                1840
Thr Ser Thr Ala Val Ser Ser Pro Thr Pro Ala Glu Gly Thr Ser
            1845                1850                1855
Ile Ala Thr Ser Thr Pro Ser Glu Gly Ser Thr Ala Leu Thr Ser Ile
            1860                1865                1870
Pro Val Ser Thr Thr Thr Val Ala Ser Ser Glu Thr Asn Thr Leu Ser
            1875                1880                1885
Thr Thr Pro Ala Val Thr Ser Thr Pro Val Thr Thr Tyr Ala Gln Val
            1890                1895                1900
Ser Ser Ser Pro Thr Thr Ala Asp Gly Ser Ser Met Pro Thr Ser Thr
1905                1910                1915                1920
Pro Arg Glu Gly Arg Pro Pro Leu Thr Ser Ile Pro Val Ser Thr Thr
            1925                1930                1935
Thr Val Ala Ser Ser Glu Ile Asn Thr Leu Ser Thr Thr Leu Ala Asp
            1940                1945                1950
Thr Arg Thr Pro Val Thr Thr Tyr Ser Gln Ala Ser Ser Ser Pro Thr
            1955                1960                1965
Thr Ala Asp Gly Thr Ser Met Pro Thr Pro Ala Tyr Ser Glu Gly Ser
            1970                1975                1980
Thr Pro Leu Thr Ser Met Pro Leu Ser Thr Thr Leu Val Val Ser Ser
1985                1990                1995                2000
Glu Ala Ser Thr Leu Ser Thr Thr Pro Val Asp Thr Ser Thr Pro Ala
            2005                2010                2015
Thr Thr Ser Thr Glu Gly Ser Ser Ser Pro Thr Thr Ala Gly Gly Thr
            2020                2025                2030
Ser Ile Gln Thr Ser Thr Pro Ser Glu Arg Thr Thr Pro Leu Ala Gly
            2035                2040                2045
Met Pro Val Ser Thr Thr Leu Val Val Ser Ser Glu Gly Asn Thr Leu
            2050                2055                2060
Ser Thr Thr Pro Val Asp Ser Lys Thr Gln Val Thr Asn Ser Thr Glu
2065                2070                2075                2080
Ala Ser Ser Ser Ala Thr Ala Glu Gly Ser Ser Met Thr Ile Ser Ala
            2085                2090                2095
Pro Ser Glu Gly Ser Pro Leu Leu Thr Ser Ile Pro Leu Ser Thr Thr
            2100                2105                2110
Pro Val Ala Ser Pro Glu Ala Ser Thr Leu Ser Thr Thr Pro Val Asp
            2115                2120                2125
Ser Asn Ser Pro Val Ile Thr Ser Thr Glu Val Ser Ser Ser Pro Ile
            2130                2135                2140
```

```
Pro Thr Glu Gly Thr Ser Met Gln Thr Ser Thr Tyr Ser Asp Arg Arg
2145                2150                2155                2160

Thr Pro Leu Thr Ser Met Pro Val Ser Thr Thr Val Ala Ser Ser
            2165                2170                2175

Ala Ile Ser Thr Leu Ser Thr Pro Val Asp Thr Ser Thr Pro Val
            2180                2185                2190

Thr Asn Ser Thr Glu Ala Arg Ser Ser Pro Thr Thr Ser Glu Gly Thr
            2195                2200                2205

Ser Met Pro Thr Ser Thr Pro Ser Glu Gly Ser Thr Pro Phe Thr Ser
            2210                2215                2220

Met Pro Val Ser Thr Met Pro Val Val Thr Ser Glu Ala Ser Thr Leu
2225                2230                2235                2240

Ser Ala Thr Pro Val Asp Thr Ser Thr Pro Val Thr Thr Ser Thr Glu
                2245                2250                2255

Ala Thr Ser Ser Pro Thr Thr Ala Glu Gly Thr Ser Ile Pro Thr Ser
                2260                2265                2270

Thr Leu Ser Glu Gly Thr Thr Pro Leu Thr Ser Ile Pro Val Ser His
            2275                2280                2285

Thr Leu Val Ala Asn Ser Glu Val Ser Thr Leu Ser Thr Thr Pro Val
    2290                2295                2300

Asp Ser Asn Thr Pro Phe Thr Ser Thr Glu Ala Ser Ser Pro Pro
2305                2310                2315                2320

Pro Thr Ala Glu Gly Thr Ser Met Pro Thr Ser Thr Ser Ser Glu Gly
                2325                2330                2335

Asn Thr Pro Leu Thr Arg Met Pro Val Ser Thr Thr Met Val Ala Ser
            2340                2345                2350

Phe Glu Thr Ser Thr Leu Ser Thr Thr Pro Ala Asp Thr Ser Thr Pro
            2355                2360                2365

Val Thr Thr Tyr Ser Gln Ala Gly Ser Ser Pro Thr Thr Ala Asp Asp
    2370                2375                2380

Thr Ser Met Pro Thr Ser Thr Tyr Ser Glu Gly Ser Thr Pro Leu Thr
2385                2390                2395                2400

Ser Val Pro Val Ser Thr Met Pro Val Val Ser Ser Glu Ala Ser Thr
                2405                2410                2415

His Ser Thr Thr Pro Val Asp Thr Ser Thr Pro Val Thr Thr Ser Thr
                2420                2425                2430

Glu Ala Ser Ser Ser Pro Thr Thr Ala Glu Gly Thr Ser Ile Pro Thr
            2435                2440                2445

Ser Pro Pro Ser Glu Gly Thr Thr Pro Leu Ala Ser Met Pro Val Ser
    2450                2455                2460

Thr Thr Pro Val Val Ser Ser Glu Ala Gly Thr Leu Ser Thr Thr Pro
2465                2470                2475                2480

Val Asp Thr Ser Thr Pro Met Thr Thr Ser Thr Glu Ala Ser Ser Ser
                2485                2490                2495

Pro Thr Thr Ala Glu Asp Ile Val Val Pro Ile Ser Thr Ala Ser Glu
            2500                2505                2510

Gly Ser Thr Leu Leu Thr Ser Ile Pro Val Ser Thr Thr Pro Val Ala
            2515                2520                2525

Ser Pro Glu Ala Ser Thr Leu Ser Thr Thr Pro Val Asp Ser Asn Ser
            2530                2535                2540

Pro Val Val Thr Ser Thr Glu Ile Ser Ser Ser Ala Thr Ser Ala Glu
2545                2550                2555                2560
```

-continued

Gly Thr Ser Met Pro Thr Ser Thr Tyr Ser Glu Gly Ser Thr Pro Leu
            2565                2570                2575

Arg Ser Met Pro Val Ser Thr Lys Pro Leu Ala Ser Ser Glu Ala Ser
            2580                2585                2590

Thr Leu Ser Thr Thr Pro Val Asp Thr Ser Ile Pro Val Thr Thr Ser
            2595                2600                2605

Thr Glu Thr Ser Ser Ser Pro Thr Thr Ala Lys Asp Thr Ser Met Pro
            2610                2615                2620

Ile Ser Thr Pro Ser Glu Val Ser Thr Ser Leu Thr Ser Ile Leu Val
2625                2630                2635                2640

Ser Thr Met Pro Val Ala Ser Ser Glu Ala Ser Thr Leu Ser Thr Thr
            2645                2650                2655

Pro Val Asp Thr Arg Thr Leu Val Thr Thr Ser Thr Gly Thr Ser Ser
            2660                2665                2670

Ser Pro Thr Thr Ala Glu Gly Ser Ser Met Pro Thr Ser Thr Pro Gly
            2675                2680                2685

Glu Arg Ser Thr Pro Leu Thr Asn Ile Leu Val Ser Thr Thr Leu Leu
            2690                2695                2700

Ala Asn Ser Glu Ala Ser Thr Leu Ser Thr Thr Pro Val Asp Thr Ser
2705                2710                2715                2720

Thr Pro Val Thr Thr Ser Ala Glu Ala Ser Ser Ser Pro Thr Thr Ala
            2725                2730                2735

Glu Gly Thr Ser Met Arg Ile Ser Thr Pro Ser Asp Gly Ser Thr Pro
            2740                2745                2750

Leu Thr Ser Ile Leu Val Ser Thr Leu Pro Val Ala Ser Ser Glu Ala
            2755                2760                2765

Ser Thr Val Ser Thr Thr Ala Val Asp Thr Ser Ile Pro Val Thr Thr
            2770                2775                2780

Ser Thr Glu Ala Ser Ser Ser Pro Thr Thr Ala Glu Val Thr Ser Met
2785                2790                2795                2800

Pro Thr Ser Thr Pro Ser Glu Thr Ser Thr Pro Leu Thr Ser Met Pro
            2805                2810                2815

Val Asn His Thr Pro Val Ala Ser Ser Glu Ala Gly Thr Leu Ser Thr
            2820                2825                2830

Thr Pro Val Asp Thr Ser Thr Pro Val Thr Thr Ser Thr Lys Ala Ser
            2835                2840                2845

Ser Ser Pro Thr Thr Ala Glu Gly Ile Val Val Pro Ile Ser Thr Ala
            2850                2855                2860

Ser Glu Gly Ser Thr Leu Leu Thr Ser Ile Pro Val Ser Thr Thr Pro
2865                2870                2875                2880

Val Ala Ser Ser Glu Ala Ser Thr Leu Ser Thr Thr Pro Val Asp Thr
            2885                2890                2895

Ser Ile Pro Val Thr Thr Ser Thr Glu Gly Ser Ser Ser Pro Thr Thr
            2900                2905                2910

Ala Glu Gly Thr Ser Met Pro Ile Ser Thr Pro Ser Glu Val Ser Thr
            2915                2920                2925

Pro Leu Thr Ser Ile Leu Val Ser Thr Val Pro Val Ala Gly Ser Glu
            2930                2935                2940

Ala Ser Thr Leu Ser Thr Thr Pro Val Asp Thr Arg Thr Pro Val Thr
2945                2950                2955                2960

Thr Ser Ala Glu Ala Ser Ser Ser Pro Thr Thr Ala Glu Gly Thr Ser
            2965                2970                2975

Met Pro Ile Ser Thr Pro Gly Glu Arg Arg Thr Pro Leu Thr Ser Met

-continued

```
            2980            2985            2990
Ser Val Ser Thr Met Pro Val Ala Ser Ser Glu Ala Ser Thr Leu Ser
        2995            3000            3005
Arg Thr Pro Ala Asp Thr Ser Thr Pro Val Thr Thr Ser Thr Glu Ala
        3010            3015            3020
Ser Ser Ser Pro Thr Thr Ala Glu Gly Thr Gly Ile Pro Ile Ser Thr
3025            3030            3035            3040
Pro Ser Glu Gly Ser Thr Pro Leu Thr Ser Ile Pro Val Ser Thr Thr
            3045            3050            3055
Pro Val Ala Ile Pro Glu Ala Ser Thr Leu Ser Thr Thr Pro Val Asp
        3060            3065            3070
Ser Asn Ser Pro Val Val Thr Ser Thr Glu Val Ser Ser Pro Thr
        3075            3080            3085
Pro Ala Glu Gly Thr Ser Met Pro Ile Ser Thr Tyr Ser Glu Gly Ser
        3090            3095            3100
Thr Pro Leu Thr Gly Val Pro Val Ser Thr Thr Pro Val Thr Ser Ser
3105            3110            3115            3120
Ala Ile Ser Thr Leu Ser Thr Thr Pro Val Asp Thr Ser Thr Pro Val
            3125            3130            3135
Thr Thr Ser Thr Glu Ala His Ser Ser Pro Thr Thr Ser Glu Gly Thr
        3140            3145            3150
Ser Met Pro Thr Ser Thr Pro Ser Glu Gly Ser Thr Pro Leu Thr Tyr
        3155            3160            3165
Met Pro Val Ser Thr Met Leu Val Val Ser Ser Glu Asp Ser Thr Leu
        3170            3175            3180
Ser Ala Thr Pro Val Asp Thr Ser Thr Pro Val Thr Thr Ser Thr Glu
3185            3190            3195            3200
Ala Thr Ser Ser Thr Thr Ala Glu Gly Thr Ser Ile Pro Thr Ser Thr
            3205            3210            3215
Pro Ser Glu Gly Met Thr Pro Leu Thr Ser Val Pro Val Ser Asn Thr
        3220            3225            3230
Pro Val Ala Ser Ser Glu Ala Ser Ile Leu Ser Thr Thr Pro Val Asp
        3235            3240            3245
Ser Asn Thr Pro Leu Thr Thr Ser Thr Glu Ala Ser Ser Ser Pro Pro
        3250            3255            3260
Thr Ala Glu Gly Thr Ser Met Pro Thr Ser Thr Pro Ser Glu Gly Ser
3265            3270            3275            3280
Thr Pro Leu Thr Ser Met Pro Val Ser Thr Thr Val Ala Ser Ser
            3285            3290            3295
Glu Thr Ser Thr Leu Ser Thr Thr Pro Ala Asp Thr Ser Thr Pro Val
        3300            3305            3310
Thr Thr Tyr Ser Gln Ala Ser Ser Pro Pro Ile Ala Asp Gly Thr
        3315            3320            3325
Ser Met Pro Thr Ser Thr Tyr Ser Glu Gly Ser Thr Pro Leu Thr Asn
        3330            3335            3340
Met Ser Phe Ser Thr Thr Pro Val Val Ser Ser Glu Ala Ser Thr Leu
3345            3350            3355            3360
Ser Thr Thr Pro Val Asp Thr Ser Thr Pro Val Thr Ser Thr Glu
            3365            3370            3375
Ala Ser Leu Ser Pro Thr Thr Ala Glu Gly Thr Ser Ile Pro Thr Ser
        3380            3385            3390
Ser Pro Ser Glu Gly Thr Thr Pro Leu Ala Ser Met Pro Val Ser Thr
        3395            3400            3405
```

```
Thr Pro Val Val Ser Ser Glu Val Asn Thr Leu Ser Thr Thr Pro Val
    3410                3415                3420

Asp Ser Asn Thr Leu Val Thr Thr Ser Thr Glu Ala Ser Ser Pro
3425                3430                3435                3440

Thr Ile Ala Glu Gly Thr Ser Leu Pro Thr Ser Thr Ser Glu Gly
            3445                3450                3455

Ser Thr Pro Leu Ser Ile Met Pro Leu Ser Thr Thr Pro Val Ala Ser
                3460                3465                3470

Ser Glu Ala Ser Thr Leu Ser Thr Thr Pro Val Asp Thr Ser Thr Pro
    3475                3480                3485

Val Thr Thr Ser Ser Pro Thr Asn Ser Ser Pro Thr Thr Ala Glu Val
    3490                3495                3500

Thr Ser Met Pro Thr Ser Thr Ala Gly Glu Gly Ser Thr Pro Leu Thr
3505                3510                3515                3520

Asn Met Pro Val Ser Thr Thr Pro Val Ala Ser Ser Glu Ala Ser Thr
                3525                3530                3535

Leu Ser Thr Thr Pro Val Asp Ser Asn Thr Phe Val Thr Ser Ser Ser
                3540                3545                3550

Gln Ala Ser Ser Ser Pro Ala Thr Leu Gln Val Thr Thr Met Arg Met
                3555                3560                3565

Ser Thr Pro Ser Glu Gly Ser Ser Ser Leu Thr Thr Met Leu Leu Ser
    3570                3575                3580

Ser Thr Tyr Val Thr Ser Ser Glu Ala Ser Thr Pro Ser Thr Pro Ser
3585                3590                3595                3600

Val Asp Arg Ser Thr Pro Val Thr Thr Ser Thr Gln Ser Asn Ser Thr
                3605                3610                3615

Pro Thr Pro Pro Glu Val Ile Thr Leu Pro Met Ser Thr Pro Ser Glu
                3620                3625                3630

Val Ser Thr Pro Leu Thr Ile Met Pro Val Ser Thr Thr Ser Val Thr
                3635                3640                3645

Ile Ser Glu Ala Gly Thr Ala Ser Thr Leu Pro Val Asp Thr Ser Thr
                3650                3655                3660

Pro Val Ile Thr Ser Thr Gln Val Ser Ser Pro Val Thr Pro Glu
3665                3670                3675                3680

Gly Thr Thr Met Pro Ile Trp Thr Pro Ser Glu Gly Ser Thr Pro Leu
                3685                3690                3695

Thr Thr Met Pro Val Ser Thr Thr Arg Val Thr Ser Ser Glu Gly Ser
                3700                3705                3710

Thr Leu Ser Thr Pro Ser Val Val Thr Ser Thr Pro Val Thr Thr Ser
                3715                3720                3725

Thr Glu Ala Ile Ser Ser Ser Ala Thr Leu Asp Ser Thr Thr Met Ser
    3730                3735                3740

Val Ser Met Pro Met Glu Ile Ser Thr Leu Gly Thr Thr Ile Leu Val
3745                3750                3755                3760

Ser Thr Thr Pro Val Thr Arg Phe Pro Glu Ser Ser Thr Pro Ser Ile
                3765                3770                3775

Pro Ser Val Tyr Thr Ser Met Ser Met Thr Thr Ala Ser Glu Gly Ser
                3780                3785                3790

Ser Ser Pro Thr Thr Leu Glu Gly Thr Thr Thr Met Pro Met Ser Thr
                3795                3800                3805

Thr Ser Glu Arg Ser Thr Leu Leu Thr Thr Val Leu Ile Ser Pro Ile
    3810                3815                3820
```

-continued

Ser Val Met Ser Pro Ser Glu Ala Ser Thr Leu Ser Thr Pro Pro Gly
3825                3830                3835                3840

Asp Thr Ser Thr Pro Leu Leu Thr Ser Thr Lys Ala Gly Ser Phe Ser
                3845                3850                3855

Ile Pro Ala Glu Val Thr Thr Ile Arg Ile Ser Ile Thr Ser Glu Arg
            3860                3865                3870

Ser Thr Pro Leu Thr Thr Leu Leu Val Ser Thr Thr Leu Pro Thr Ser
        3875                3880                3885

Phe Pro Gly Ala Ser Ile Ala Ser Thr Pro Leu Asp Thr Ser Thr
    3890                3895                3900

Thr Phe Thr Pro Ser Thr Asp Thr Ala Ser Thr Pro Thr Ile Pro Val
3905                3910                3915                3920

Ala Thr Thr Ile Ser Val Ser Val Ile Thr Glu Gly Ser Thr Pro Gly
            3925                3930                3935

Thr Thr Ile Phe Ile Pro Ser Thr Pro Val Thr Ser Ser Thr Ala Asp
        3940                3945                3950

Val Phe Pro Ala Thr Thr Gly Ala Val Ser Thr Pro Val Ile Thr Ser
    3955                3960                3965

Thr Glu Leu Asn Thr Pro Ser Thr Ser Ser Ser Ser Thr Thr Thr Ser
    3970                3975                3980

Phe Ser Thr Thr Lys Glu Phe Thr Thr Pro Ala Met Thr Thr Ala Ala
3985                3990                3995                4000

Pro Leu Thr Tyr Val Thr Met Ser Thr Ala Pro Ser Thr Pro Arg Thr
            4005                4010                4015

Thr Ser Arg Gly Cys Thr Thr Ser Ala Ser Thr Leu Ser Ala Thr Ser
        4020                4025                4030

Thr Pro His Thr Ser Thr Ser Val Thr Thr Arg Pro Val Thr Pro Ser
        4035                4040                4045

Ser Glu Ser Ser Arg Pro Ser Thr Ile Thr Ser His Thr Ile Pro Pro
    4050                4055                4060

Thr Phe Pro Pro Ala His Ser Ser Thr Pro Pro Thr Thr Ser Ala Ser
4065                4070                4075                4080

Ser Thr Thr Val Asn Pro Glu Ala Val Thr Thr Met Thr Thr Arg Thr
            4085                4090                4095

Lys Pro Ser Thr Arg Thr Thr Ser Phe Pro Thr Val Thr Thr Thr Ala
        4100                4105                4110

Val Pro Thr Asn Thr Thr Ile Lys Ser Asn Pro Thr Ser Thr Pro Thr
        4115                4120                4125

Val Pro Arg Thr Thr Thr Cys Phe Gly Asp Gly Cys Gln Asn Thr Ala
    4130                4135                4140

Ser Arg Cys Lys Asn Gly Gly Thr Trp Asp Gly Leu Lys Cys Gln Cys
4145                4150                4155                4160

Pro Asn Leu Tyr Tyr Gly Glu Leu Cys Glu Glu Val Val Ser Ser Ile
            4165                4170                4175

Asp Ile Gly Pro Pro Glu Thr Ile Ser Ala Gln Met Glu Leu Thr Val
        4180                4185                4190

Thr Val Thr Ser Val Lys Phe Thr Glu Glu Leu Lys Asn His Ser Ser
        4195                4200                4205

Gln Glu Phe Gln Glu Phe Lys Gln Thr Phe Thr Glu Gln Met Asn Ile
    4210                4215                4220

Val Tyr Ser Gly Ile Pro Glu Tyr Val Gly Val Asn Ile Thr Lys Leu
4225                4230                4235                4240

Arg His Asp Val Phe Gln His His Trp His Pro Ser Ala Lys His Tyr

```
                    4245          4250          4255
Gly Asp Pro Val Arg Pro
        4260

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gcacatgtca gctgcaacgc a                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ggctctgtgt ttgcagctct c                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aactgctagc accacagcaa                                                20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ctcagtcaca gtcttctcat t                                              21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cagtcaacta catgacacat t                                              21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
actctgtcta ctctccgagc c                                              21

<210> SEQ ID NO 11
```

```
<211> LENGTH: 21
<212> TYPE: DNA
<213> ORGANISM: Artificial Sequence
<220> FEATURE:
<223> OTHER INFORMATION: Primer

<400> SEQUENCE: 11
gaccagaagc catactgcat c                                              21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ctcctcactc ccagacttct c                                              21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gtgatagcct ctgaactggc c                                              21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
catggtgctg gcaggcatac t                                              21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gtaggagatg aacttgcctg a                                              21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ctgtgccaag aaccacaaca t                                              21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
```

```
ctcctcactc ccagacttct c                                                    21

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gccagctcct ctggggtgac                                                      20

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gatatgagca cacctctgac c                                                    21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
atgttgtggt tcttggcaca g                                                    21

<210> SEQ ID NO 21
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 21
agagctccga tg                                                              12

<210> SEQ ID NO 22
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 22
acaagggtga gtgacc                                                          16

<210> SEQ ID NO 23
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 23
ggacaggtaa ggcaac                                                          16
```

```
<210> SEQ ID NO 24
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 24
caacatgtaa gtgatt                                                    16

<210> SEQ ID NO 25
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 25
acataggtga gtgcaa                                                    16

<210> SEQ ID NO 26
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 26
gaacaggtaa gtctgg                                                    16

<210> SEQ ID NO 27
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 27
gctacggtaa gtgtct                                                    16

<210> SEQ ID NO 28
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 28
gctcaggtga actctg                                                    16

<210> SEQ ID NO 29
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site
```

```
<400> SEQUENCE: 29
ctgaaggtag gtgata                                                      16

<210> SEQ ID NO 30
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 30
gtgcctgtga gtgctc                                                      16

<210> SEQ ID NO 31
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 31
gaaacggtga gcgagc                                                      16

<210> SEQ ID NO 32
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 32
gccaaggtat tggcct                                                      16

<210> SEQ ID NO 33
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 33
acaaaggtaa gaaggg                                                      16

<210> SEQ ID NO 34
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 34
tctctttcag acctca                                                      16

<210> SEQ ID NO 35
<211> LENGTH: 16
<212> TYPE: DNA
```

```
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 35
tcttaaacag gttctg                                                 16

<210> SEQ ID NO 36
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 36
ttccacagag gctttg                                                 16

<210> SEQ ID NO 37
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 37
cccgcctcag ggccac                                                 16

<210> SEQ ID NO 38
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 38
tgcctttcag atgaat                                                 16

<210> SEQ ID NO 39
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 39
ccctcttcag tcttgg                                                 16

<210> SEQ ID NO 40
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 40
tctttcacag acatga                                                 16
```

```
<210> SEQ ID NO 41
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 41
cccccaccag aggact                                              16

<210> SEQ ID NO 42
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 42
cccatctcag ctgcgt                                              16

<210> SEQ ID NO 43
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 43
ccatcactag gcaaaa                                              16

<210> SEQ ID NO 44
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 44
cctccacaag atgatg                                              16

<210> SEQ ID NO 45
<211> LENGTH: 16
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: Splice Site

<400> SEQUENCE: 45
ctcttttcag atccga                                              16
```